(12) United States Patent
Van Epps et al.

(10) Patent No.: US 8,883,139 B2
(45) Date of Patent: *Nov. 11, 2014

(54) COMPOSITIONS AND SOFT TISSUE REPLACEMENT METHODS

(75) Inventors: Dennis E. Van Epps, Goleta, CA (US); Guang-Liang Jiang, Irvine, CA (US); Wha Bin Im, Irvine, CA (US)

(73) Assignee: Allergan Inc., Irvine, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 13/398,783

(22) Filed: Feb. 16, 2012

(65) Prior Publication Data

US 2012/0189708 A1 Jul. 26, 2012

Related U.S. Application Data

(63) Continuation-in-part of application No. 13/193,744, filed on Jul. 29, 2011, now Pat. No. 8,697,056.

(60) Provisional application No. 61/444,078, filed on Feb. 17, 2011, provisional application No. 61/375,144, filed on Aug. 19, 2010.

(51) Int. Cl.
| | | |
|---|---|---|
| *A01N 63/00* | (2006.01) | |
| *A61F 2/20* | (2006.01) | |
| *A61K 31/195* | (2006.01) | |
| *A61K 8/73* | (2006.01) | |
| *A61K 8/36* | (2006.01) | |
| *A61K 8/49* | (2006.01) | |
| *A61L 27/54* | (2006.01) | |
| *A61K 8/42* | (2006.01) | |
| *A61K 8/69* | (2006.01) | |
| *A61L 27/40* | (2006.01) | |
| *A61K 31/728* | (2006.01) | |
| *A61K 8/98* | (2006.01) | |
| *A61K 8/37* | (2006.01) | |
| *A61K 8/46* | (2006.01) | |
| *A61L 27/36* | (2006.01) | |
| *A61Q 19/08* | (2006.01) | |

(52) U.S. Cl.
CPC .............. *A61K 31/195* (2013.01); *A61K 8/735* (2013.01); *A61K 8/361* (2013.01); *A61L 2400/06* (2013.01); *A61K 8/4926* (2013.01); *A61L 2300/412* (2013.01); *A61L 2430/04* (2013.01); *A61L 27/54* (2013.01); *A61K 8/42* (2013.01); *A61K 8/69* (2013.01); *A61K 2800/91* (2013.01); *A61L 2430/34* (2013.01); *A61L 27/40* (2013.01); *A61K 8/4913* (2013.01); *A61K 31/728* (2013.01); *A61K 8/981* (2013.01); *A61K 8/37* (2013.01); *A61K 8/4986* (2013.01); *A61K 8/46* (2013.01); *A61L 27/3604* (2013.01); *A61K 8/49* (2013.01); *A61Q 19/08* (2013.01)
USPC .................. 424/93.7; 514/476; 623/8; 623/9; 623/10

(58) Field of Classification Search
USPC ..................... 424/93.7; 623/8, 9, 10; 514/476
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,282,954 A | 8/1981 | Hill |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Malson et al. |
| 4,772,419 A | 9/1988 | Malson et al. |

(Continued)

FOREIGN PATENT DOCUMENTS

| | | |
|---|---|---|
| CA | 949965 | 6/1974 |
| EP | 0273823 | 7/1988 |

(Continued)

OTHER PUBLICATIONS

Moller et al. Biomolecular Engineering (2007) 24: 496-504.*

(Continued)

*Primary Examiner* — Susan Hanley
(74) *Attorney, Agent, or Firm* — Linda Allyson Fox

(57) ABSTRACT

The invention relates to compositions comprising a hydrogel material that comprises a glycosaminoglycan polymer, adipose tissue and a compound of the structure The composition is administered to a site of a soft tissue condition including those of breast tissue. The hydrogel material can be porous or of solid particles. The glycosaminoglycan polymer can be a hyaluronan polymer.

18 Claims, 7 Drawing Sheets

(56) References Cited

U.S. PATENT DOCUMENTS

| | | |
|---|---|---|
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,716,404 A | 2/1998 | Vacanti |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,972,385 A | 10/1999 | Liu et al. |
| 5,980,930 A | 11/1999 | Fenton et al. |
| 6,013,679 A | 1/2000 | Kuo et al. |
| 6,066,325 A | 5/2000 | Wallace et al. |
| 6,129,761 A | 10/2000 | Hubbell |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,316,822 B2 | 1/2008 | Binette |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette |
| 7,902,171 B2 | 3/2011 | Reinmuller et al. |
| 8,052,990 B2 | 11/2011 | Hermitte et al. |
| 8,053,423 B2 | 11/2011 | Lamberti et al. |
| 8,124,120 B2 | 2/2012 | Sadozai |
| 8,137,702 B2 | 3/2012 | Binette et al. |
| 8,153,591 B2 | 4/2012 | Masters et al. |
| 8,246,947 B2 | 8/2012 | Hedrick et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,455,465 B2 | 6/2013 | Molliard |
| 8,524,213 B2 | 9/2013 | Leshchiner et al. |
| 8,575,129 B2 | 11/2013 | Bellini |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0224406 A1* | 11/2004 | Altman et al. .............. 435/395 |
| 2004/0265389 A1 | 12/2004 | Yui et al. |
| 2004/0266992 A1* | 12/2004 | Migliaresi et al. .......... 530/353 |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0104692 A1 | 5/2007 | Quijano et al. |
| 2007/0104693 A1 | 5/2007 | Quijano et al. |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet |
| 2009/0022808 A1 | 1/2009 | Champion |
| 2009/0028817 A1 | 1/2009 | Niklason et al. |
| 2009/0036403 A1 | 2/2009 | Stroumpoulis |
| 2009/0042834 A1 | 2/2009 | Karageozian et al. |
| 2009/0093755 A1 | 4/2009 | Schroeder et al. |

(56) References Cited

U.S. PATENT DOCUMENTS

| | | |
|---|---|---|
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel |
| 2009/0155362 A1 | 6/2009 | Longin |
| 2009/0162415 A1 | 6/2009 | Huang et al. |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0247651 A1 | 9/2010 | Kestler |
| 2010/0255068 A1 | 10/2010 | Stroumpoulis et al. |
| 2010/0316683 A1 | 12/2010 | Piron |
| 2011/0034684 A1 | 2/2011 | Yokokawa |
| 2011/0070281 A1 | 3/2011 | Altman |
| 2011/0077737 A1 | 3/2011 | Stroumpoulis et al. |
| 2011/0097381 A1 | 4/2011 | Binette |
| 2011/0104800 A1 | 5/2011 | Kensy et al. |
| 2011/0118206 A1 | 5/2011 | Lebreton |
| 2011/0150823 A1 | 6/2011 | Huang |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0183001 A1 | 7/2011 | Rosson et al. |
| 2011/0183406 A1 | 7/2011 | Kensy |
| 2011/0194945 A1 | 8/2011 | Kensy et al. |
| 2011/0224164 A1 | 9/2011 | Lebreton |
| 2011/0229574 A1 | 9/2011 | Guillen et al. |
| 2011/0295238 A1 | 12/2011 | Kensy et al. |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen |
| 2012/0100217 A1 | 4/2012 | Green |
| 2012/0100611 A1 | 4/2012 | Kensy et al. |
| 2012/0136011 A1* | 5/2012 | Jiang et al. ................. 514/260.1 |
| 2012/0142684 A1* | 6/2012 | Burk et al. ................. 514/234.2 |
| 2012/0156265 A1 | 6/2012 | Binette et al. |
| 2012/0164098 A1 | 6/2012 | Schroeder et al. |
| 2012/0172328 A1 | 7/2012 | Lebreton |
| 2012/0190644 A1 | 7/2012 | D'Este |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0101547 A1 | 4/2013 | Whitcup et al. |
| 2013/0116188 A1 | 5/2013 | Pollock et al. |
| 2013/0116411 A1 | 5/2013 | Pollock et al. |
| 2013/0123210 A1 | 5/2013 | Liu |
| 2013/0237615 A1 | 9/2013 | Meunier |
| 2013/0274222 A1 | 10/2013 | Home |

FOREIGN PATENT DOCUMENTS

| | | |
|---|---|---|
| EP | 0416250 | 3/1991 |
| EP | 0416846 | 3/1991 |
| EP | 1247522 | 10/2002 |
| EP | 1419792 | 4/2003 |
| EP | 1398131 | 3/2004 |
| EP | 1532991 | 5/2005 |
| EP | 1726299 | 11/2006 |
| EP | 2236523 | 10/2010 |
| FR | 2733427 | 10/1996 |
| FR | 2920000 | 2/2009 |
| FR | 2924615 | 6/2009 |
| JP | 55-153711 | 11/1980 |
| JP | 2007063177 | 3/2007 |
| JP | 20021080501 | 10/2013 |
| WO | WO 86/00079 | 1/1986 |
| WO | WO 86/00912 | 2/1986 |
| WO | WO 92/00105 | 1/1992 |
| WO | WO 92/20349 | 11/1992 |
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/79342 | 10/2001 |
| WO | WO 02/05753 | 1/2002 |
| WO | WO 02/06350 | 1/2002 |
| WO | WO 02/09792 | 2/2002 |
| WO | WO 02/17713 | 3/2002 |
| WO | WO 03/007782 | 1/2003 |
| WO | WO 2004/020473 | 3/2004 |
| WO | WO 2004/022603 | 3/2004 |
| WO | WO 2004/073759 | 9/2004 |
| WO | WO 2004/092223 | 10/2004 |
| WO | WO 2005/040224 | 5/2005 |
| WO | WO 2005/067944 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | 2007136738 | 11/2007 |
| WO | WO 2007/128923 | 11/2007 |
| WO | WO 2008/034176 | 3/2008 |
| WO | 2008063569 | 5/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | 2008148071 | 12/2008 |
| WO | 2009003135 | 12/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | 2011072399 | 6/2011 |
| WO | 2012077055 | 6/2012 |

(56) References Cited

FOREIGN PATENT DOCUMENTS

OTHER PUBLICATIONS

Wei Wang J. Mater. Sci. (2006) 17: 1259-1265.*
Buck et al, "Injectable Fillers for our Facial Rejuvenation: a Review", Journal of Plastic, Reconstructive and Aesthetic Surgery, (2009), 62:11-18, XP002668828.
Helary et al., "Concentrated collagen hydrogels as dermal substitutes", Biomaterials 31 (2010) 481-490.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.
Altman et al., "Adhesion, migration and mechanics of human adipose-tissue-derived stem cells on silk fibroin-chitosan matrix", Acta Biomaterialia 6 (2010) 1388-1397.
Taguchi et al., "An improved method to prepare hyaluronic acid and type II collagen composite matrices", Journal of Biomedical Materials Research (2002), 61(2), 330-336.
Greco et al., "Hyaluronic Acid Stimulates Human Fibroblast Proliferation Within a Collagen Matrix", J. Cell. Physiol. 177 (3):465-473, 1998.
Calderon et al., "Type II Collagen-Hyaluronan Hydrogel—A Step Towards a Scaffold for Intervertebral Disc Tissue Engineering", European Cells and Materials, vol. 20, pp. 134-148, 2010.
Doillon et al., "Fibroblast growth on a porous collagen sponge containing hyaluronic acid and fibronectin", Biomaterials 8 (1087) 195-200.
Davidenko et al., "Xollagen-hyaluronic acid scaffolds for adipose tissue engineering", Acta Biomaterialia 6 (2010) 3957-3968.
Millay et al.; "Vasoconstrictors in Facial Plastic Surgery"; Archives of Otolaryngology—Head & Neck Surgery; vol. 117; pp. 160-163; Feb. 1991.
Wahl, "European Evaluation of a New Hyaluronic Acid Filler Incorporating Lidocaine", Journal of Cosmetic Dermatology; vol. 7; pp. 298-303; 2008.
*Aesthetic Buyers Guide*, "Juvéderm Raises Standards"; Jan./Feb. 2007 (5 pp.), www.miinews.com.
Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.
Albano et al.; "Hyroxyethyl Radicals in Ethanol Hepatotoxicity"; Frontiers in Bioscience; vol. 4; pp. 533-540; 1999.
Allemann et al.; "Hyaluronic acid gel (JUVADERM) preparations in the treatment of facial wrinkles and folds"; Clinical Interventions in Aging; vol. 3, No. 4; pp. 629-634; 2008.
Antunes et al.; "Efficacy of Intrarectal Lidocaine Hydrochloride Gel for Pain control in Patients Undergoing Transrectal Prostate Biopsy"; International Braz J Urol; vol. 30, No. 5; pp. 380-383; Sep.-Oct. 2004.
Atanassoff et al.; "The Effect of Intradermal Administration of Lidocaine and Morphine on the Response to Thermal Stimulation"; Anesth Analg; vol. 84; pp. 1340-1343; 1997.
Baumann et al.; "Comparison of smooth-gel hyaluronic acid dermal fillers with cross-linked bovine collagen: a multicenter, double-masked, randomized, within-subject study"; Dermatol. Surg.; vol. 33(Suppl 2); pp. S128-S135 2007.
Beasley et al.; "Hyaluronic acid fillers: a comprehensive review"; Facial Plast. Surg.; vol. 25, No. 2; pp. 86-94; 2009.
Beer; "Dermal fillers and combinations of fillers for facial rejuvenation"; Dermatol. Clin.; vol. 27, No. 4; pp. 427-432; 2009.
Belda et al.; "Hyaluronic acid combined with mannitol to improve protection against free-radical endothelial damage: Experimental Model"; J.Cataract Refract Surg; Vo. 31; pp. 1213-1218; 2005.
Bircher, et al.; "Delayed-Type Hypersensitivity to Subcutaneous Lidocaine With Tolerance to Articaine: Confirmation by In Vivo and In Vitro Tests"; Contact Dermatitis; vol. 34; pp. 387-389; 1996.
Bluel et al.; "Evaluation of Reconstituted Collagen Tape as a Model for Chemically Modified Soft Tissues", Biomat. Med. Dev. Art. Org.; vol. 9(1); pp. 37-46; 1981.
Capozzi et al., "Distant Migration of Silicone Gel From a Ruptured Breast Implant", Plastic and Reconstructive Surgery; vol. 62; pp. 302-303; 1978.
Carlin et al., "Effect of anti-inflammatory drugs on xanthine oxidase and xanthine oxidase induced depolymerization of hyaluronic acid"; Agents and Actions; vol. 16 (5); pp. 377-384; 1985.
Carruthers et al.; "The science and art of dermal fillers for soft-tissue augmentation"; J. Drugs Dermatol; vol. 8(4); pp. 335-350; 2009.
Champion et al., "Role of Target Geometry in Phagocytosis"; S. Proc. Nat. Acad. Sci.; vol. 103; No. 13; pp. 4930-4934; Mar. 28, 2006.
Chin et al., "Allergic Hypersensitivity to Lidocaine Hydrochloride", International journal of Dermatology, vol. 19; pp. 147-148; Apr. 1980.
Chvapil, "Collagen Sponge: Theory and Practice of Medical Applications", J. Biomed Mater. Res., vol. II, pp. 721-741; 1977.
Clark et al., "The Influence of Triamcinolone Acetonide on Joint Stiffness in the Rat", J Bone Joint Surg; vol. 53-A; pp. 1409-1414; Oct. 1971.
Cohen et al., "Organization and Adhesive Properties of the Hyaluronan Pericellular Coat of Chrondrocytes and Epithelial Cells", Biophys J.; vol. 85; pp. 1996-2005; Sep. 2003.
Deland, "Intrathecal Toxicity Studies with Benzyl Alcohol", Toxicol Appl Pharmacol; vol. 25; pp. 153-156; 1973.
Desai et al., J Pharm Sci Abstract only; 84 (2): 212-215; Feb. 1995.
Eyre et al., Top Curr. Chem., vol. 247, pp. 207-229; 2005.
Falcone et al.; "Crosslinked hyaluronic acid dermal fillers: a comparison of rheological properties." J Biomed Mater Res; vol. 87(1); pp. 264-271; 2008.
Falcone et al.; "Temporary polysaccharide dermal fillers: a model for persistence based on physical properties." Dermatol Surg.; vol. 35(8); pp. 1238-1243; 2009.
Farley et al., "Diluting Lidocaine and Mepivacaine in Balanced Salt Solution Reduces the Pain of Intradermal Injection", Regional Anesthesia; vol. 19(1); pp. 48-51; 1994.
Frati et al., "Degradation of hyaluronic acid by photosensitized riboflavin in vitro. Modulation of the effect by transition metals, radical quenchers, and metal chelators"; Free Radical Biology Medicine; vol. 22 (7); pp. 1139-1144 1997.
Fujinaga et al., "Reproductive and Teratogenic Effects of Lidocaine in Sprague-Dawley Rats"; Anesthesiology vol. 65; pp. 626-632; 1986.
Gammaitoni et al., "Pharmacokinetics and safety of continuously applied lidocaine patches 5%", Am J Health Syst Pharm; vol. 59; pp. 2215-2220; Nov. 15, 2002.
GinShiCel MH Hydroxy Propyl methyl Cellulose, Web Page http://www.ginshicel.cn/MHPC.html, Nov. 12, 2008.
Gold; "Use of Hyaluronic acid fillers for the treatment of the aging face"; Clin. Interventions Aging; vol. 2(3); pp. 369-376; 2007.
Goldberg; "Breakthroughs in US dermal fillers for facial soft-tissue augmentation"; J Cosmet Laser Ther; vol. 11; pp. 240-247; 2009.
Graefe et al., "Sensitive and specific photometric determination of mannitol in human serum"; Clin Chem Lab Med; vol. 41, No. 8; pp. 1049-1055; 2003.
Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.
Grillo et al., "Thermal Reconstitution of Collagen from Solution and the Response to Its Heterologous Implantation", JSR; vol. II, No. 1, pp. 69-82; Jan., 1962.
Hassan et al., "Effects of Adjuvants to local anaesthetics on their duration. III. Experimental studies of hyaluronic acid"; Abstract Pub Med Acta Anesthesiol Scand; vol. 29(4); pp. 384-388; May 1985.
Hayashibara, "AA2G"; Sep. 23, 2007, http://web.archive.org/web/20079230720l0/http://www.hayashibara-intl.com/cosmetics/aa2g.html.
Helliwell, "Use of an Objective Measure of Articular Stiffness to Record Changes in Finger Joints After Intra-Articular Injection of Corticosteroid", An Theum Dis; vol. 56; pp. 71-73; 1997.

(56) References Cited

OTHER PUBLICATIONS

Hertzberger-Ten Cate et al., "Intra-Articular Steroids in Pauciarticular Juvenile Chronic Arthritis", Type I, Eur J Pediatr; vol. 150; pp. 170-172; 1991.
Hetherington, "Potential for Patient Harm From Intrathecal Administration of Preserved Solutions", Abstract only Med J; vol. 173(3); p. 141; Aug. 2000.
Hurst, "Adhesive Arachnoiditis and Vascular Blockage Caused by Detergents and Other Chemical Irritants: an Experimental Study", J Path Bact, vol. LXX, No. 70; pp. 167-177; 1955.
Intramed Mannitol 20% m/v Infusion, package insert, pp. 1-2 (2010) http://home.intekom.com/pharm/intramed/manitl20.html.
Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.
Kablik et al. "Comparative physical properties of hyaluronic acid dermal fillers." Dermatol. Surg.; vol. 35(Suppl. 1); pp. 302-312; 2009.
Klein, "Skin Filling Collagen and Other Injectables of the Skin", Dermatologic Clinics; vol. 19, No. 3, pp. 491-588; Jul. 2001.
Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.
Kulicke et al., "Visco-Elastic Properties of Sodium Hyaluronate Solutions," American Institue of Physics; 3 pages; 2008.
Laeschke, "Biocompatibility of Microparticles into Soft Tissue Fillers", Semin. Cutan. Med. Surg., vol. 23; pp. 214-217; 2004.
Lamar et al., "Antifibrosis Effect of Novel Gels in Anterior Ciliary Slerotomy (ACS)," ARVO 2002 abstract only.
Levy et al., "Lidocaine hypersensitivity after subconjunctival injection", Can J Ophthalmol 2006; vol. 41, No. 2; pp. 204-206.
Lupo; "Hyaluronic acid fillers in facial rejuvenation." Semin. Cutan. Med. Surg.; vol. 25; pp. 122-126; 2006.
Mackley et al., "Delayed-Type Hypersensitivity to Lidocaine", Arch Dermatol, vol. 139; pp. 343-346; Mar. 2003.
Mancinelli et al., "Intramuscular High-Dose Triamcinolone Acetonide in the Treatment of Severe Chronic Asthma", West J. Med; vol. 167(5); pp. 322-329; Nov. 1997.
Matsumoto et al., "Reducing the Discomfort of Lidocaine Administration through pH Buffering," Journal of Vascular and Interventional Radiology; vol. 5, No. 1; pp. 171-175; Nov. 1997.
McCarty et al., "Inflammatory Reaction After Intrasynovial Injection of Microcrystalline Adrenocorticosteroid Esters", Arthritis and Rheuymatism; vol. 7(4); pp. 359-367; 1964.
McCleland et al.; "Evlaution of Artecoll Polymethacrylate Implant for Soft-Tissue Augmentation: Biocompatibility and Chemical Chartacterization"; Plastric Reconstructive Surgery; vol. 100(6); pp. 1466-1474; Nov. 1997.
McPherson et al; "Development and Biochemical Characterization of Injectable Collagen," J. Dermatol Surg Oncol; vol. 14 (Suppl1); pp. 13-20; Jul. 7, 1988.
Orvisky et al., "High-molecular-weight hyaluronan—a valuable tool in testing the antioxidative activity of amphiphilic drugs stobadine and vinpocetine"; J. Pharm. Biomed. Anal.; vol. 16; pp. 419-424; 1997.
Osmitrol (generic name Mannitol),Official FDA Information, side effects and uses, pp. 1-10 (2010) http://www.drugs.com/pro/osmitrol.html.
Prestwich; "Evaluating drug efficacy and toxicology in three dimensions: using synthetic extracellular matrices in drug discovery"; Accounts of Chemical Research; vol. 41, No. 1; pp. 139-148; Jan., 2008.
Rehakova et al.; "Properties of collagen and hyaluronic acid composite materials and their modifications by chemical crosslinking," Journal of Biomedical Materials Research; vol. 30; pp. 369-372; 1996.
Remington's Pharmaceutical Science Mac Publishing Company, Easton, PA 16th Edition 1980; 1- page.

Rosenblatt et al., "The Effect of Collagen Fiber Size Distribution on the Release Rate of Proteins from Collagen Matrices by Diffusion", J. Controlled Rel., vol. 9; pp. 195-203; 1989.
Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.
Sannino et al., "Crosslinking of Cellulose Derivatives and Hyaluronic Acid with Water-Soluble Carbodiimide," Polymer; vol. 46; pp. 11206-11212 ; 2005.
Sculptra® Aesthetic (injectable poly-L-lactic acid) Directions for Use, Dermik Laboratories product insert (Jul. 2009), sanofi-aventis U.S. LLC; 10 pages.
Segura et al. "Crosslinked hyaluronic acid hydrogels: a strategy to functionalize and pattern." Biomaterials; vol. 26; pp. 359-371; 2005.
Selvi et al, "Arthritis Induced by Corticosteroid Crystals", J. Rheumatology; vol. 34:3; 1 page; 2004.
Serban et al., "Modular Extracellular Matrices: Solutions for the Puzzle"; Methods; vol. 45(1)pp. 93-98; 2008.
Shu et al., "Synthesis and evaluation of injectable, in situ crosslinkable synthetic extracellular matrices for tissue engineering"; J. Biomed. Mater. Res. A.; vol. 79(4); pp. 902-912; 2006.
Silver et al., "Physical Properties of Hyaluronic Acid and Hydroxypropylmethylcellulose in Solution: Evaluation of Coating Ability"; Journal of Applied Biomaterials; vol. 5; pp. 89-98; 1994.
Smith et al., "Five Percent Lidocaine Cream Applied Simultaneously to Skin and Mucosa of the Lips Creates Excellent Anesthesia for Filler Injections", Dermatol Surg; vol. 31; pp. 1635-1637; 2005.
Tezel et al.,, "The science of hyaluronic acid dermal fillers", J. Cosmet. Laser Ther.; vol. 10; pp. 35-42; 2008.
TRB Chemedica Ophthalmic Line, VISIOL, product info., pp. 1-2; No date.
VISIOL, Viscoelstic gel for use in ocular surgery, (2010) p. 1, htt://www.trbchemedica.com/index.php/option=com_content&tas.
Waraszkiewicz et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, pp. 1215-1218, Nov. 1981.
Xia et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al., "Effect of Cross-Linking Reagents for Hyaluronic Acid Hydrogel Dermal Fillers on Tissue Augmentation and Regeneration", Bioconjugate Chem., vol. 21; pp. 240-247; 2010.
Yui, et al., "Inflammation responsive degradation of crosslinked hyaluronic acid gels," Journal of Controlled Release, vol. 22; pp. 105-116; 1992.
Yui et al., "Photo-responsive degradation of heterogeneous hydrogels comprising crosslinked hyaluronic acid and lipid microspheres for temporal drug delivery," Journal of Controlled Release; vol. 26; pp. 141-145; 1993.
Yun et al., "Hyaluronan Microspheres for Sustained Gene Delivery and Site-Specific Targeting", Biomaterials, vol. 25, pp. 147-157, 2004.
Zheng Shu et al., "In situ crosslinkable hyaluronan hydrogels for tissue engineering." Biomaterials; vol. 25; pp. 1339-1348; 2004.
Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Cui et al; "The Comparison of Physicochemical Properties of Four Cross-Linked Sodium Hyaluronate Gels with Different Cross-Linking Agents"; Advanced Material Research; Vols. 396-398; pp. 1506-1512; 2012.
Lindvall et al.; "Influence of Various Compounds on the Degradation of Hyaluronic Acid by a Myeloperoxidase System"; Chemcio-Biological Interactions; vol. 90; pp. 1-12; 1994.

(56) References Cited

OTHER PUBLICATIONS

Weidmann; "New Hyaluronic Acid Filler for Subdermal and Long-Lasting Volume Restoration of the Face"; European Dermatology; pp. 65-68; 2009.

Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.

Crosslinking Technical Handbook, Thermo Scientific, pp. 1-48, published Apr. 2009.

Park et al., "In vireio evaluation of conjugated Hyalruonic acid with Ascorbic Acid", Journal of Bone & Joint Surgery, British vol. 92-B, XP-002706399, 2010.

Van Der Rest et al., "Collagen family of proteins", The FASEB Journal, vol. 5, Oct. 1991, pp. 2814-2823.

International Pharmacopoeia Fourth Edition, Methods of Analysis: 5. Pharmaceutical technical procedures: 5.8 Methods of sterilization, http://apps.who.int/phint/en/d/Jb/7.5.9.html, Sep. 25, 2013.

Sterilization-microbiology, http://www.ask.com/wiki/Sterilization_(microbiology), pp. 1-9, Sep. 25, 2013.

Kreisel et al., "Cell-delivery therapeutics for adipose tissue regeneration", Advanced Drug Delivery Reviews 62 (2010) 798-813.

\* cited by examiner (a) KOH, I-$R^2$, dioxane/$H_2O$; (b) KOH, I-$R^3$, dioxane/$H_2O$; (c) KOH, 1,2-dibromoethane, dioxane/$H_2O$; (d) KOH, dioxane/$H_2O$.

(a) KOH, MeI, dioxane/H$_2$O; (b) Baker's Yeast, D-glucose, H$_2$O; (c) TBSOTf, 2,6-lutidine, CH$_2$Cl$_2$; (d) LDA, THF; PhSeCl; (e) 30% H$_2$O$_2$, CH$_2$Cl$_2$.

(a) TBSCl, etc.; (b) n-BuLi; $(CH_2O)_n$ = paraformaldehyde; (c) $Ac_2O$, pyridine; (d) Jones oxidation; (e) MeOH, AcCl; (f) $PPh_3$, $I_2$, imidazole, $CH_2Cl_2$.

(a) Cp$_2$ZrHCl, NIS; (b) t-BuLi, THF -78 °C; (c) Me$_2$Zn; (d) HF-pyridine, CH$_3$CN; separate diastereomers; (e) rabbit liver esterase, pH 7.2 phosphate buffer, CH$_3$CN; (f) NiCl$_2$, NaBH$_4$, ethylenediamine, H$_2$, THF.

(a) n-BuLi; ethylene oxide; (b) Dess-Martin [O]; (c) ethynylmagnesium bromide;
(d) TBSCl, DMAP, Et₃N; (e) Cp₂ZrHCl; NIS.

(a) ClCO$_2$CH$_2$CH$_3$, Et$_3$N, CH$_2$Cl$_2$; NH$_4$OH $_{(aq)}$;
(b) EDCl, N-hydroxysuccinimide, H$_2$NCH$_2$CH$_2$OH, DMF.

COMPOSITIONS AND SOFT TISSUE REPLACEMENT METHODS

CROSS REFERENCE

This application claims priority pursuant to 35 U.S.C. §119 (e) to U.S. Provisional Patent Application No. 61/444,078, filed Feb. 17, 2011, and is a continuation-in-part pursuant to 35 U.S.C. §120 to U.S. Non-Provisional patent application Ser. No. 13/193,744, now U.S. Pat. No. 8,697,056 filed on Jul. 29, 2011, which claims priority to U.S. Provisional Patent Application 61/375,144, filed on Aug. 19, 2010, each of which is hereby incorporated by reference in its entirety.

BACKGROUND

Soft tissue replacement methods are commonly used for a wide variety of clinical and cosmetic purposes. One use involves reconstructive applications that rebuild and restore a body part or structure to correct deformities from congenital anomalies, trauma, cancer, infections, disease, or medication side effects. The replacement tissue serves to support surrounding tissue and to maintain the normal appearance of the body. The restoration of this normal appearance has an extremely beneficial psychological effect on post-operative patients, alleviating much of the shock and depression that often follows extensive surgical procedures. Another use involves augmentation applications that alter a body part or structure usually to improve its cosmetic or aesthetic appearance. Augmentation of the appearance also has beneficial psychological effects that improve self-esteem, well-being, and confidence of an individual. A third use involves structural applications that provide support to a body part or structure to improve its function, thereby alleviating a symptom associated with a disorder involving soft tissue loss. Examples of such disorders include, without limitation, stress urinary incontinence, fecal incontinence, vocal cord paralysis, vocal atrophy, vocal implantation, intubation trauma, post-hemilaryngectomy defects, irradiation damage, lumbar disc repair, and plantar footpad repair.

Soft tissue replacement methods currently rely on two general approaches: 1) implantation of artificial or alloplastic fillers like soft tissue implants, and injectable polymers and hydrogels; and 2) transplantation of tissue like tissue flaps and autologous tissue transfers. A drawback to the use of artificial or alloplastic fillers it that these inorganic materials lack any metabolic activity, do not become physiologically incorporated into the body, and as such, surrounding tissue and blood supply does not develop within the implanted material. In addition, artificial or alloplastic fillers risk migration and/or extrusion from the implant site. Furthermore, many of these fillers produce only temporary effects because the body rapidly reabsorbs them. Fillers providing long-term effects frequently induce a foreign body response resulting in formation of an avascular, fibrous capsule around the filler, which limits performance, distorts the aesthetic appearance of the surrounding area, and can cause pain to the individual. Furthermore, long-term fillers, like soft tissue implants, do not remodel with the aging tissue resulting in a material that may not be aesthetically acceptable as the patient's tissues undergo the normal physiologic changes associated with aging.

Although the use of transplanted tissue avoids the problems associated with artificial or alloplastic fillers, drawbacks are also associated with these procedures. In these procedures, loss of transplanted tissue volume over time as a result of its resorption by the body is a major problem. For example, transplantation of adipose tissue generally results in a loss of 20% to 90% of its volume within the first year. This tissue loss is unpredictable and is a result of poor survival and/or regeneration from progenitor cells in the transplanted tissue due to necrosis and a lack of vascular formation. With respect to adipose tissue, tissue breakdown is associated with traumatic rupture of the cells, avascular necrosis, apoptosis of the adipocytes, inflammation secondary to apoptosis, fibrosis and contraction of the graft, and/or delipidation of the adipocytes with subsequent volume loss. Failed tissue grafts sometime produce stellate and irregular nodules with calcifications. As such, transplanted tissue methods are usually performed two or three times to obtain the desired effect, resulting in massive time and cost.

One of the major underlying causes for tissue breakdown seen in transplanted tissue methods is the lack of a blood supply sufficient to support the transplanted tissue. For example, alleviation of tissue ischemia is critically dependent upon formation of new blood vessels. The growth of new blood vessels and associated vasculature or repair or remodeling of existing blood vessels and associated vasculature provides collateral circulation in and around an ischemic area, improves blood flow, and alleviates the symptoms caused by the ischemia. Thus, compositions and methods that promote new blood vessel formation within a transplanted tissue are needed as this will improve the survival rate of such tissues, thereby achieving reliable long-term survival of grafted tissues.

The present specification provides novel compositions and soft tissue replacement methods using compositions that reduce tissue volume loss by increasing the survival rate of the transplanted tissue. This improved survival rate is achieved by administering a compound that promotes new blood vessel formation, thereby ensuring that a blood supply adequate to support the transplanted tissue is established.

BRIEF SUMMARY

Thus, aspects of the present specification disclose a composition comprising adipose tissue, a hydrogel material, and a compound having the structure of formula I, a pharmaceutically acceptable salt thereof, or a pharmaceutically acceptable amine salt thereof,

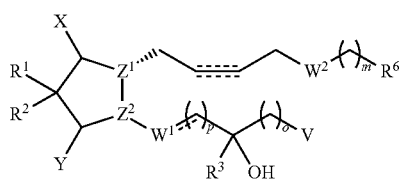

wherein each dashed line represents the presence or absence of a bond; $R^1$, $R^2$ and $R^3$ are each independently selected from H or $C_1$-$C_6$ alkyl; $R^6$ is $CO_2H$, $CO_2R^7$, $CON(R^7)_2$, $CONHCH_2CH_2OH$, $CON(CH_2CH_2OH)_2$, $CH_2OR^7$, $P(O)(OR^7)_2$, or

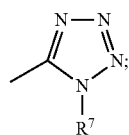

$R^7$ is H or $C_{1-6}$ hydrocarbyl; X and Y are each independently selected from H, OH, =O, Cl, Br, I, or $CF_3$; $Z^1$ and $Z^2$ are each independently selected from CH or N; $W^1$ and $W^2$ are each independently selected from CH, $CH_2$, optionally substituted aryl, or optionally substituted heteroaryl; m is 0, 1, 2, 3, 4, 5, or 6; o is 0, 1, 2, 3, 4; p is 0 or 1; and V is $C_{1-6}$ alkyl, optionally substituted aryl, or optionally substituted heteroaryl.

Other aspects of the present specification disclose a composition comprising adipose tissue, a hydrogel material, and a compound having the structure of formula VI, a pharmaceutically acceptable salt thereof, or a pharmaceutically acceptable amine salt thereof

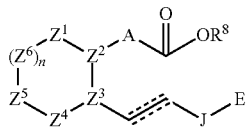

VI wherein each dashed line represents the presence or absence of a bond; $Z^2$ and $Z^3$ are independently CH or N; $Z^1$, $Z^4$, $Z^5$, and $Z^6$ are each independently $CR^9$, $CHR^9$, NH, O, or S; A is —$(CH_2)_6$—, or cis —$CH_2CH=CH—(CH_2)_3$—, wherein 1 or 2 carbons may be substituted with S or O; or A is —$(CH_2)_m$—Ar—$(CH_2)_o$— wherein Ar is optionally substituted aryl or optionally substituted heteroaryl, the sum of m and o is from 1, 2, 3, or 4, and wherein one $CH_2$ may be substituted with S or O; $R^8$ is H, hydrocarbyl, or hydrocarbyl-OH; $R^9$ is independently H, $C_{1-6}$ alkyl, OH, F, Cl, Br, I, or O; J is $C_{1-6}$ alkyl, $C_{1-6}$—O-alkyl, C=O, or CHOH; E is $C_{1-12}$ alkyl, $R^{10}$, or —Y—$R^{10}$ wherein Y is $CH_2$, S, or O, and $R^{10}$ is optionally substituted aryl or optionally substituted heteroaryl; and n is 0 or 1.

Other aspects of the present specification disclose a composition comprising adipose tissue, a hydrogel material, and a compound having the structure of formula IX

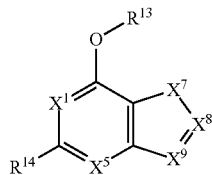

IX wherein $X^1$ and $X^5$ are independently CH or N; $X^7$ is NH, O, or S; $X^8$ and $X^9$ are independently CH or N; $R^{13}$ is optionally substituted aryl or optionally substituted heteroaryl; and $R^{14}$ is $C_{1-6}$ alkyl, optionally substituted aryl, or optionally substituted heteroaryl.

Other aspects of the present specification disclose a composition comprising adipose tissue, a hydrogel material, and a compound having the structure of compound 24, a pharmaceutically acceptable salt thereof, or a pharmaceutically acceptable amine salt thereof.

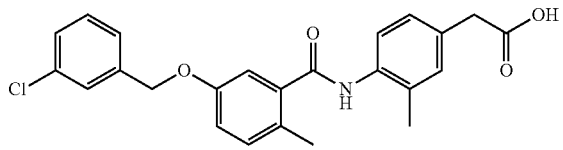 [SMILES: Cc1cc(CC(=O)O)ccc1NC(=O)c1cc(OCc2cccc(Cl)c2)ccc1C]

Compound 24

Yet other aspects of the present specification disclose a method of treating a soft tissue condition of an individual, the method comprising the step of administering a composition disclosed herein to a site of the soft tissue condition, wherein administration of the composition promotes formation of a blood supply sufficient to support the transplanted tissue, thereby treating the soft tissue site. Non-limiting examples of a soft tissue condition include breast imperfection, defect, disease and/or disorder, such as, e.g., a breast augmentation, a breast reconstruction micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken cheeks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

Still other aspects of the present specification disclose a method of treating a soft tissue condition of an individual, the method comprising the steps of a) administering the adipose tissue to a site of the soft tissue condition; b) administering a composition comprising a compound as disclosed herein to the site of the soft tissue condition; and c) administering a hydrogel material to the site of the soft tissue condition, wherein administration of the compound promotes formation of a blood supply sufficient to support the transplanted tissue, thereby treating the soft tissue site. Non-limiting examples of a soft tissue condition include those described above.

DETAILED DESCRIPTION

Figure 1:
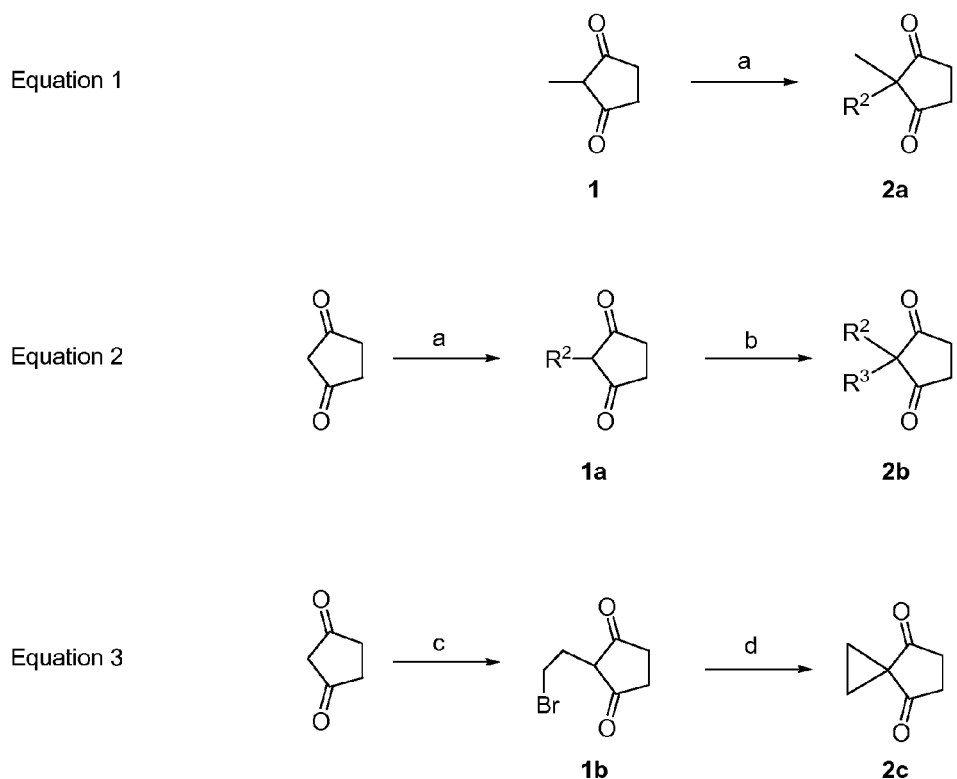
FIGS. 1-7 illustrate possible ways to prepare compounds disclosed herein.

Insufficient blood vessel formation in a repairing or otherwise metabolically active tissue results in inadequate delivery of oxygen, nutrients, and other substances necessary to establish essential physiological functions to the area and promote wound healing. The formation of blood vessels within a tissue may occur by angiogenesis and/or vasculogenesis. As used herein, the term "angiogenesis" refers to a physiological process involving the growth of new blood vessels from pre-existing vessels and includes sprouting angiogenesis, the formation of new blood vessel by sprouting off existing ones, and splitting angiogenesis (intussusception), the formation of new blood vessel by splitting off existing ones. As used herein, the term "vasculogenesis" refers to a physiological process involving the de novo production of new blood-vessels by proliferating endothelial stem cells, and as such, the formation of new blood vessels when there were no pre-existing ones.

Blood vessel formation, whether angiogenesis or vasculogenesis, requires signals from growth factors and other proteins that direct and control the process, such as, e.g., fibroblast growth factors (like FGF-1 and FGF-2), vascular endothelial growth factors (like VEGF-A and VEGF-C), angiopoietins (like Ang-1 and Ang-2), platelet derived growth factor (PDGF), monocyte chemotactic protein-1 (MCP-1) (also known as chemokine (C—C motif) ligand 2 (CCL-2)), transformation growth factor betas (TGF-β1, TGF-β2, TGF-β3, and TGF-β4), vascular cell adhesion molecules (like VCAM-1), matrix metalloproteinases (like MMP-2 and MPP-9), integrins, cadherins, plasminogen activators, plasminogen activator inhibitors, and ephrin.

Of the factors listed above, two of the more critical factors for new blood vessel formation are FGF-2 and VEGF. One of the most important functions of FGF-2 (or bFGF) is the promotion of endothelial cell proliferation and the physical organization of endothelial cells into tube-like structures, thus promoting angiogenesis and vasculogenesis. FGF-2 is a more potent factor in new blood vessel formation than VEGF or PDGF. As well as stimulating blood vessel growth, FGF-2 is an important factor in wound healing. This factor stimulates proliferation of fibroblasts and endothelial cells that give rise to new vessel formation and developing granulation tissue; both increase blood supply and fill up a wound space/cavity early in the wound-healing process.

VEGF is another major contributor to new blood vessel formation. VEGF causes a massive signaling cascade in endothelial cells resulting in the release of many other factors known to be responsible for new blood vessel formation. For example, binding to VEGF receptor-2 (VEGFR-2) starts a tyrosine kinase signaling cascade that stimulates the production of factors that variously stimulate vessel permeability (eNOS, producing NO), proliferation/survival (FGF-2), migration (ICAMs/VCAMs/MMPs) and finally differentiation into mature blood vessels. In addition, in vitro studies demonstrated that upon stimulation by VEGF and FGF-2, endothelial cells would proliferate, migrate, and eventually form tube structures resembling capillaries.

The compounds disclosed herein, and compositions comprising such compounds, upregulate both FGF-2 and VEGF (see Example 2). In addition, both incisional and ulcer wound models demonstrate that the upregulation of FGF-2 and VEGF results in an improved wound healing response (see Example 2).

Without wishing to be bound by any particular theory, the compounds, compositions and methods disclosed herein increase the survival rate of transplanted tissue by promoting new blood vessel formation within the transplanted tissue. Administration of a compound, either as a composition with the transplanted tissue or as a prior or subsequent administration to the transplantation procedure, upregulate factors essential to new blood vessel formation, like FGF-2 and VEGF. This upregulation initiates the signaling cascade in endothelial cells responsible for the formation of new blood vessel. This initiation results in the formation of new blood vessels that, in turn, provide oxygen, nutrients, and other substances necessary to establish essential physiological functions to the transplanted tissue. This adequate blood supply supports the establishment, growth and survival of the transplanted tissue. Thus, the compounds, compositions and methods disclosed herein ameliorate or prevent one of the major underlying causes for the tissue breakdown of transplanted tissue, namely the lack of a blood supply sufficient to support the transplanted tissue. In addition, the compounds and compositions disclosed herein are superior to the mere addition of factors critical to new blood vessel formation, like FGF-2 and VEGF, because these small molecules are more stable and less costly then these protein-based therapies. Furthermore, formation of new blood vessels can soften scar tissue, capsular contracture by facilitating the remolding of fibrous tissue into normal soft tissue typical of the affected region.

Aspects of the present specification provide, in part, a composition comprising adipose tissue. As used herein, the term "adipose tissue" is synonymous with "fat" or "fatty tissue" and refers to a loose fibrous connective tissue comprising fat cells (adipocytes) and multiple types of regenerative cells. Adipose tissue may comprise brown and/or white adipose tissue taken from any body site, such as, e.g., subcutaneous, omental/visceral, interscapular, or mediastinal. It may be obtained from any organism having adipose tissue, or the adipose tissue used may be from a primary cell culture or an immortalized cell line.

Adipose tissue may be collected from the same individual who is undergoing the soft tissue replacement procedure (autograft), from a donor individual who is not the same individual as the one undergoing the soft tissue replacement procedure (allograft), or from an animal source (xenograft). As used herein, the term "autotransplantation" refers to the transplantation of organs, tissues, or cells from one part of the body to another part in the same individual, i.e., the donor and recipient are the same individual. Tissue transplanted by such "autologous" procedures is referred to as an autograft or autotransplant. As used herein, the term "allotransplantation" refers to the transplantation of organs, tissues, or cells from a donor to a recipient, where the donor and recipient are different individuals, but of the same species. Tissue transplanted by such "allologous" procedures is referred to as an allograft or allotransplant. As used herein, the term "xenotransplantation" refers to the transplantation of organs, tissues, or cells from a donor to a recipient, where the donor is of a different species as the recipient. Tissue transplanted by such "xenologous" procedures is referred to as a xenoograft or xenotransplant.

Adipose tissue can be collected by any procedure that can harvest adipose tissue useful for the compositions and methods disclosed herein, including, without limitation a liposuction (lipoplasty) procedure or a lipectomy procedure. Procedures useful for collecting adipose tissue should minimize the trauma and manipulation associated with adipose tissue removed. Adipose tissue may be harvested from any suitable region, including, without limitation, a mammary region, an abdominal region, a thigh region, a flank region, a gluteal region, a trochanter region, or a gonadal region. Procedures useful for collecting adipose tissue are well known to a person of ordinary skill in the art. The selected procedures may be performed concomitantly with liposculpture.

A liposuction procedure harvests adipose tissue by aspirating the tissue using a cannula. The cannula may be connected to a syringe for manual aspiration or to a power assisted suction device, like an aspirator, adapted to collect the adipose tissue into a vacuum bottle. A liposuction procedure does not maintain an intact blood supply of the harvested tissue. The syringe may be a 10, 20 or 60 mL syringe fitted with a 12 or 14 gauge cannula. Non-limiting examples of liposuction procedures include suction-assisted liposuction (SAL), ultrasound-assisted liposuction (UAL), power-assisted liposuction (PAL), twin-cannula (assisted) liposuction (TCAL or TCL), or external ultrasound-assisted liposuction (XUAL or EUAL), or water-assisted liposuction (WAL). In addition, the liposuction procedures listed above can be used with any of the following procedures that vary the amount of fluid injected during the procedure, such as, e.g., dry liposuction, wet liposuction, super-wet liposuction, tumescent liposuction, or laser-assisted liposuction. An autologous soft tissue transfer procedure typically uses adipose tissue collected from a liposuction procedure.

Although the harvested tissue may be used directly to make the disclosed compositions, it is more typically processed to purify and/or enrich for healthy adipocytes and regenerative cells. For example, the harvested adipose tissue may be separated from any debris and/or contaminants such as, e.g., blood, serum, proteases, lipases, lipids and other oils, and/or other bodily fluids; tumescent fluid and/or other materials used in the liposuction procedure; and/or other impurities suctioned during the procedure. Methods useful in separating debris and/or contaminants from adipose tissue useful to make the disclosed compositions, including, without limitation, centrifugation, sedimentation, filtration, and/or absorption. In addition, or alternatively, the harvested adipose tissue may be processed by washing in a physiological buffer like saline to remove any debris and/or contaminants.

A lipectomy procedure harvests adipose tissue by surgical excision from a donor site in a manner that minimizes damage to the blood supply of the tissue using standard surgical operative procedures. This harvested tissue is then implanted into the region needing the soft tissue replacement. A tissue flap or tissue graft procedure typically uses adipose tissue collected from a lipectomy procedure. A tissue flap is a section of living tissue that maintained its blood supply as the tissue is moved from one area of the body to another.

A local flap uses a piece of skin and underlying tissue that lie adjacent to the wound, including adipose tissue. The flap remains attached at one end so that it continues to be nourished by its original blood supply, and is repositioned over the wounded area. A regional flap uses a section of tissue that is attached by a specific blood vessel. When the flap is lifted, it needs only a very narrow attachment to the original site to receive its nourishing blood supply from the tethered artery and vein. A musculocutaneous flap, also called a muscle and skin flap, is used when the area to be covered needs more bulk and a more robust blood supply. Musculocutaneous flaps are often used in breast reconstruction to rebuild a breast after mastectomy. As an example, the transverse rectus abdominus myocutaneous flap (TRAM flap) is a tissue flap procedure that uses muscle, fat and skin from an abdomen to create a new breast mound after a mastectomy. This type of flap remains "tethered" to its original blood supply. In a bone/soft tissue flap, bone, along with the overlying skin, is transferred to the wounded area, carrying its own blood supply.

Typically, a wound that is wide and difficult or impossible to close directly may be treated with a skin graft. A skin graft is a patch of healthy skin that is taken from one area of the body, called the "donor site," and used to cover another area where skin is missing or damaged. There are three basic types of skin grafts. A split-thickness skin graft, commonly used to treat burn wounds, uses only the layers of skin closest to the surface. A full-thickness skin graft might be used to treat a burn wound that is deep and large, or to cover jointed areas where maximum skin elasticity and movement are needed. As its name implies, a full-thickness (all layers) section of skin from the donor site are lifted. A composite graft is used when the wound to be covered needs more underlying support, as with skin cancer on the nose. A composite graft requires lifting all the layers of skin, adipose tissue, and sometimes the underlying cartilage from the donor site.

The amount of adipose tissue collected will typically vary from individual to individual and can depend on a number of factors including, but not limited to, amount of adipose tissue required for the soft tissue replacement method, aesthetic expectations, age, body habitus, coagulation profile, hemodynamic stability, co-morbidities, and physician preference. A liposuction procedure may harvest from about 1 mL to about 1500 mL of adipose tissue. A lipectomy procedure typically harvests about 1 g to about 5,000 g.

Adipose tissue comprises multiple regenerative cells. As used herein, the term "regenerative cell" refers to any cells that cause or contribute to complete or partial regeneration, restoration, or substitution of structure or function of an organ, tissue, or physiologic unit or system to thereby provide a therapeutic, structural or cosmetic benefit. Examples of regenerative cells include stem cells, progenitor cells, and precursor cells. As used herein, the term "stem cell" refers to a multipotent regenerative cell with the potential to differentiate into a variety of other cell types that perform one or more specific functions and has the ability to self-renew. Some of the stem cells disclosed herein may be pluripotent. Exemplary examples of stem cells include, without limitation, adipose-derived stem cells (ASCs; adipose-derived stromal cells), endothelial-derived stem cells (ESCs), hemopoietic stem cells (HSGs), and mesenchyma stem cells (MSCs). As used herein, the term "progenitor cell" refers to an oligopotent regenerative cell with the potential to differentiate into more than one cell type, or a unipotent regenerative cell with the potential to differentiate into only a single cell type, that performs one or more specific functions and has limited or no ability to self-renew. Exemplary examples of progenitor cells include, without limitation, endothelial progenitor cells, keratinocytes, monoblasts, myoblasts, and pericytes. As used herein, the term "precursor cell" refers to a unipotent regenerative cell with the potential to differentiate into one cell type that performs one or more specific functions and may retain extensive proliferative capacity that enables the cells to proliferate under appropriate conditions. Exemplary examples of precursor cells include, without limitation, adipoblast (lipoblast or preadipocytes), de-differentiated adipocytes, angioblasts, endothelial precursor cells, fibroblasts, lymphoblasts, and macrophages.

Harvested adipose tissue can be supplemented with regenerative cells such as, e.g., stem cells, progenitor cells, and precursor cells. Regenerative cells may promote new blood vessel formation, diminish necrosis, and/or promote a supportive microenvironment in the transplanted tissue, thereby improving survivability of the transplanted tissue. Regenerative cells can be obtained form a variety of sources. For example, adipose tissue is rich in regenerative cells that have the ability to restore and reconstruct various soft tissue defects in response to local differentiation clues from the recipient site. As such, a portion of the collected adipose tissue may be further processed in order to purify regenerative cells that can then be added back to the remainder of the harvested adipose tissue in order to enrich this material for these cells. Exemplary methods describing such cell enrichment procedures can be found in, e.g., U.S. Patent Publication 2005/0025755, Yoshimura, et al., Characterization of Freshly Isolated and Cultured Cells Derived form the Fatty and Fluid Portions of liposuction Aspirates, *J. Cell. Physiol.* 208: 1011-1041 (2006); Yoshimura, et al., Cell-Assisted Lipotransfer for Facial Lipoatrophy: Effects of Clinical Use of Adipose-Derived Stem Cells, *Dermatol. Surg.* 34: 1178-1185 (2008); Yoshimura, et al., Cell-Assisted Lipotransfer for Cosmetic Breast Augmentation: Supportive Use of Adipose-Derived Stem/Stromal Cells, *Aesth. Plast. Surg.* 32: 48-55 (2008); each of which is hereby incorporated by reference in its entirety.

In addition, harvested adipose tissue can be supplemented with regenerative cells obtained from cell cultures, such as, e.g., primary cell cultures and established cell cultures. For example, a portion of harvested adipose tissue from an individual can be cultured in a manner to produce primary cell cultures enriched for regenerative cells. Alternatively, established cell lines derived from regenerative cells from adipose tissue, or another tissue source, can be cultured, harvested, and added to adipose tissue collected from an individual. Exemplary methods describing such cell culture compositions and procedures can be found in, e.g., U.S. Patent Publication 2009/0246182; U.S. Patent Publication 2009/0317367; U.S. Patent Publication 2008/0299213; Rehman, et al., Secretion of Angiogenic and Antiapoptotic Factors by Human Adipose Stromal Cells, *Circulation*, 109: r52-r58 (2004); Kilroy, et al., Cytokine Profile of Human Adipose-Derived Stem Cells: Expression of Angiogenic, Hematopoietic, and Pro-Inflammatory Factors, *J. Cell. Physiol.,* 212: 702-709 (2007); each of which is hereby incorporated by reference in its entirety.

Harvested adipose tissue may be immediately used to make the compositions disclosed herein. Alternatively, harvested adipose tissue, whether unprocessed or processed, may be stored for use at some future date. Harvested tissue is typically stored using a slow freezing method of the tissue to −20° C., with or without cryopreservatives. Stored adipose tissue can typically be stored for at least 6 months.

Aspects of the present specification provide, in part, a composition comprising a compound having the structure of formula I, a pharmaceutically acceptable salt thereof, or a pharmaceutically acceptable amine salt thereof,

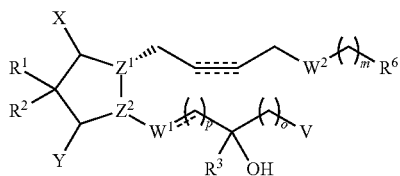

I wherein each dashed line represents the presence or absence of a bond; $R^1$, $R^2$ and $R^3$ are each independently selected from H or $C_{1-6}$ alkyl; $R^6$ is $CO_2H$, $CO_2R^7$, $CON(R^7)_2$, $CONHCH_2CH_2OH$, $CON(CH_2CH_2OH)_2$, $CH_2OR^7$, $P(O)(OR^7)_2$, or

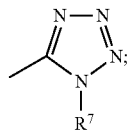

$R^7$ is H or $C_{1-6}$ hydrocarbyl; X and Y are each independently selected from H, OH, =O, Cl, Br, I, or $CF_3$; $Z^1$ and $Z^2$ are each independently selected from CH or N; $W^1$ and $W^2$ are each independently selected from CH, $CH_2$, optionally substituted aryl, or optionally substituted heteroaryl; m is 0, 1, 2, 3, 4, 5, or 6; o is 0, 1, 2, 3, 4; p is 0 or 1; and V is $C_{1-6}$ alkyl, optionally substituted aryl, or optionally substituted heteroaryl.

The method of preparing the compounds represented by formula I can be found in, e.g., Donde, et el., 10,10-Dialkyl Prostanoic Acid Derivatives as Agents for Lowering Intraocular Pressure, U.S. Pat. No. 6,875,787; Donde, et el., 10,10-Dialkyl Prostanoic Acid Derivatives as Agents for Lowering Intraocular Pressure, U.S. Patent Publication 2004/0235958; Donde, et al., Treatment of Inflammatory Bowel Disease, U.S. Patent Publication 2005/0164992, each of which is hereby incorporated by reference in its entirety. See also companion applications Jiang, et al., Compositions and Methods for Skin Repair, U.S. Provisional Patent Application 61/374,439; and Jiang, et al., Compositions and Methods for Treating Corneal Haze, U.S. Provisional Patent Application 61/369,232; each of which is incorporated by reference in its entirety.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

Unless stereochemistry is unambiguously depicted, any structure or name for a compound used herein may refer to any stereoisomer or any mixture of stereoisomers.

Unless otherwise indicated, when a compound or chemical structural feature such as aryl is referred to as being "optionally substituted," it includes a feature that has no substituents (i.e. "unsubstituted"), or a feature that is "substituted," meaning that the feature has one or more substituents. The term "substituent" has the ordinary meaning known to one of ordinary skill in the art, and includes a moiety that replaces one or more hydrogen atoms attached to a parent compound or structural feature. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. In some embodiments, a substituent may consist of 1, 2, 3, 4, 5, 6, 7, 8, 9, 10, 11, or 12 non-hydrogen atoms and any necessary hydrogen atoms. Some non-hydrogen atoms may include C, N, O, S, Si, F, Cl, Br, I, P, etc.

Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, carboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc., or a combination thereof. The term "combination thereof" in the previous list indicates that substituents may also be a combination of any of the above substituents, wherein a hydrogen atom of one substituent is replaced by another substituent. For example, substituents may be a combination of alkyl and aryl (e.g. $CH_2$-phenyl, $C_2H_4$-heteraryl, etc.), alkyl and alkoxy (e.g. $CH_2OCH_2$), alkyl and halo (e.g. $C_2H_4Cl$, $C_3H_6F$, etc.), acyl and hydroxyl (e.g. —$COCH_2OH$), etc.

In some embodiments, a substituent may be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc.

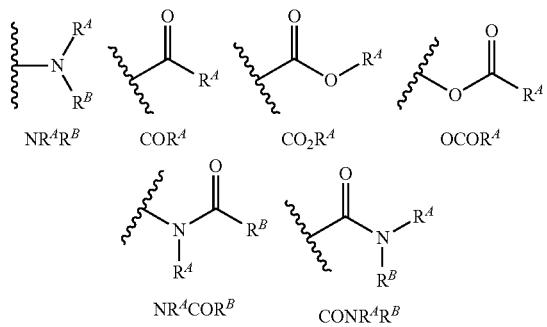

Each $R^A$ may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

Each $R^B$ may independently be H, or $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

For convenience, the term "molecular weight" is used with respect to a moiety or part of a molecule to indicate the sum of the atomic masses of the atoms in the moiety or part of a molecule, even though it may not be a complete molecule.

Structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

attachment may occur at any position normally occupied by a hydrogen atom.

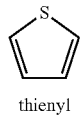
thienyl

As used herein, the term "hydrocarbyl" has the broadest meaning generally understood in the art, and may include a moiety composed of carbon and hydrogen. Some examples may include alkyl, alkenyl, alkynyl, aryl, etc., and combinations thereof, and may be linear, branched, cyclic, or a combination thereof. Hydrocarbyl may be bonded to any other number of moieties (e.g. be bonded to 1 other group, such as —$CH_3$, —$CH$=$CH_2$, etc.; 2 other groups, such as -phenyl-, —$C$≡$C$—, etc.; or any number of other groups) that the structure may bear, and in some embodiments, may contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein, the term "heterocyclyl" has the broadest meaning generally understood in the art, and may include a heterocyclic ring, or a ring containing one or more heteroatom as ring atoms.

As used herein the term "aryl" has the broadest meaning generally understood in the art, and may include an aromatic ring or aromatic ring system such as phenyl, naphthyl, etc. Any aryl identified herein may be $C_{6-10}$ aryl. The term "heteroaryl" also has the meaning understood by a person of ordinary skill in the art, and may refer to an "aryl" which has one or more heteroatoms in the ring or ring system. Examples of "heteroaryl" may include, but are not limited to, pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc. Any heteroaryl identified herein may be $C_{3-9}$ heteroaryl.

As used herein, the term "haloalkyl" refers to alkyl having one or more halo substituents.

In another embodiment, the compound has the structure of formula II,

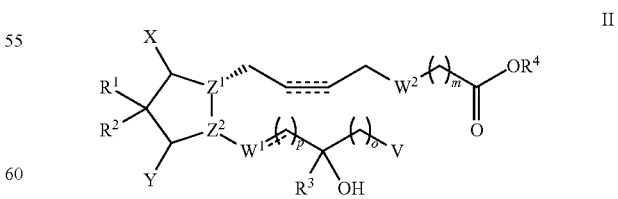

II wherein each dashed line represents the presence or absence of a bond; $R^1$, $R^2$ and $R^3$ are each independently selected from H or $C_{1-6}$ alkyl; $R^4$ is H or $C_{1-6}$ hydrocarbyl; X and Y are each independently selected from H, OH, =O, Cl, Br, I, or $CF_3$; $Z^1$ and $Z^2$ are each independently selected from CH or N; $W^1$ and $W^2$ are each independently selected from CH, $CH_2$, optionally substituted aryl, or optionally substituted heteroaryl; m is 0, 1, 2, 3, or 4; o is 0, 1, 2, 3, or 4; p is 0 or 1; and V is $CH_3$, aryl, optionally substituted aryl, or optionally substituted heteroaryl.

In an aspect of this embodiment, V is

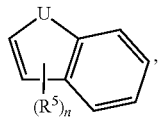

wherein U is N, O, or S; $R^5$ is F, Cl, Br, I, $C_{1-6}$ hydrocarbyl; and n is 0, 1, 2, 3, 4, 5, 6, or 7; and. In another aspect of this embodiment, U is S; $R^5$ is F, Cl, Br, or I; and n is 1, 2, or 3. In yet another aspect of this embodiment $W^2$ is thienyl.

In another embodiment, the compound has the structure of formula III

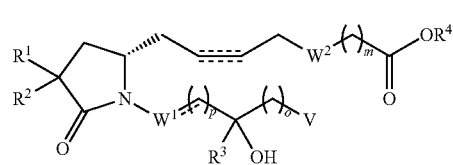

III wherein each dashed line represents the presence or absence of a bond; $R^1$, $R^2$ and $R^3$ are each independently selected from H or $C_{1-6}$ alkyl; $R^4$ is H or $C_1$-$C_6$ hydrocarbyl; $W^1$ and $W^2$ are each independently selected from CH, $CH_2$, optionally substituted aryl, or optionally substituted heteroaryl; m is 0, 1, 2, 3, or 4; o is 0, 1, 2, 3, or 4; p is 0 or 1; and V is $CH_3$, optionally substituted aryl or optionally substituted heteroaryl.

In yet another embodiment, the compound has the structure of formula IV:

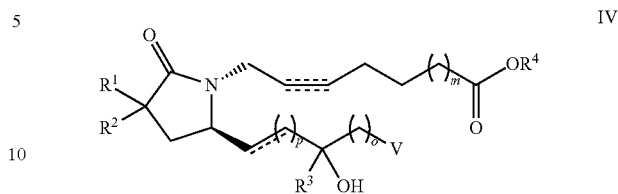

IV wherein each dashed line represents the presence or absence of a bond; $R^1$, $R^2$ and $R^3$ are each independently selected from H or $C_{1-6}$ linear alkyl; $R^4$ is H, $C_{1-6}$ hydrocarbyl; m is 0, 1, 2, 3, or 4; o is 0, 1, 2, 3, or 4; p is 0 or 1; and V is $CH_3$, optionally substituted aryl or optionally substituted heteroaryl.

In still another embodiment, the compound has the structure of formula V:

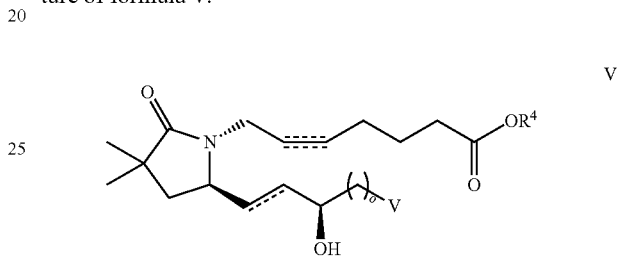

V wherein each dashed line represents the presence or absence of a bond; $R^4$ is H, $C_{1-6}$ hydrocarbyl; o is 0, 1, 2, 3, or 4; and V is $CH_3$, optionally substituted aryl or optionally substituted heteroaryl.

In a further embodiment, the compound has a structure of one of the following compounds listed in Table 1.

TABLE 1

| Structure | Low Rf diastereomer | High Rf diastereomer |
|---|---|---|
| 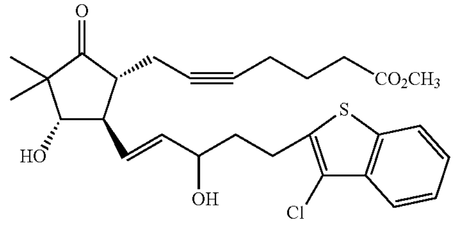 [SMILES: COC(=O)CCCC#CC[C@H]1C(=O)C(C)(C)[C@@H](O)[C@@H]1/C=C/C(O)CCc1sc2ccccc2c1Cl] | 34 | 35 |
| 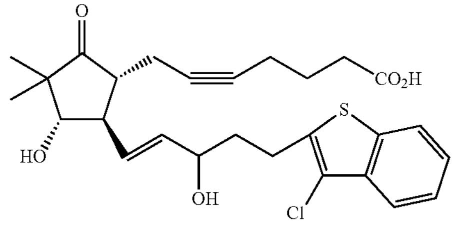 [SMILES: CC1(C)C(=O)[C@H](CC#CCCCC(=O)O)[C@@H](/C=C/C(O)CCc2sc3ccccc3c2Cl)[C@@H]1O] | 36 | 37 |

TABLE 1-continued

| Structure | Low Rf diastereomer | High Rf diastereomer |
| --- | --- | --- |
| (structure) | 38 | 39 |
| (structure) | 40 | 41 |
| (structure) | 42 | |
| (structure) | 43 | |
| (structure) | 44 | |
| (structure) | 45 | |
| (structure) | 46 | 47 |

TABLE 1-continued

| Structure | Low Rf diastereomer | High Rf diastereomer |
|---|---|---|
| (structure) | 48 | 49 |
| (structure) | 50 | 51 |
| (structure) | 52 | 53 |
| (structure) | 54 | 55 |
| (structure) | 56 | 57 |
| (structure) | 58 | 59 |

TABLE 1-continued

| Structure | Low Rf diastereomer | High Rf diastereomer |
|---|---|---|
| 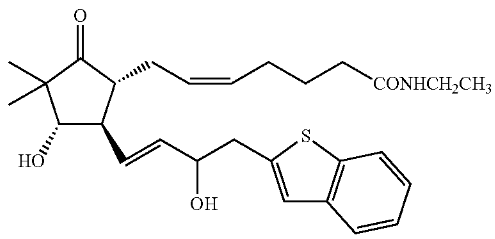 | 60 | 61 |
| 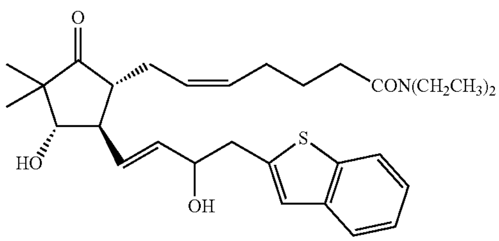 | 62 | 63 |
| 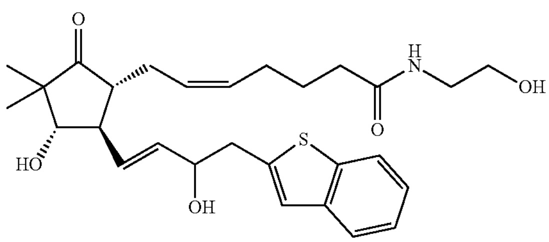 [SMILES: CC1(C)C(=O)[C@H](C/C=C\CCCC(=O)NCCO)[C@@H](/C=C/C(O)Cc2cc3ccccc3s2)[C@@H]1O] | 64 | 65 |
| 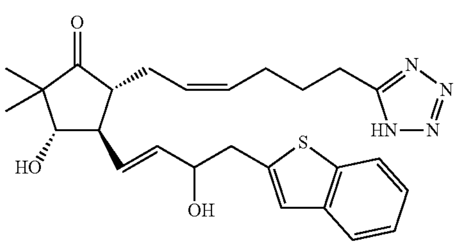 [SMILES: CC1(C)C(=O)[C@H](C/C=C\CCCc2nnn[nH]2)[C@@H](/C=C/C(O)Cc2cc3ccccc3s2)[C@@H]1O] | 66 | 67 |
| 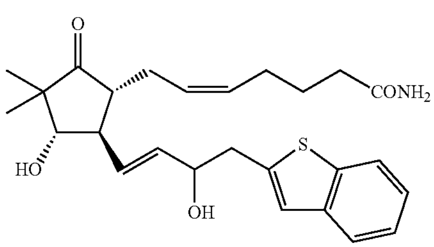 [SMILES: CC1(C)C(=O)[C@H](C/C=C\CCCC(N)=O)[C@@H](/C=C/C(O)Cc2cc3ccccc3s2)[C@@H]1O] | 68 | 69 |
| 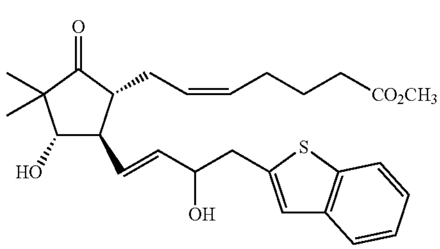 [SMILES: COC(=O)CCC/C=C\C[C@H]1C(=O)C(C)(C)[C@@H](O)[C@@H]1/C=C/C(O)Cc1cc2ccccc2s1] | 70 | 71 |

TABLE 1-continued

| Structure | Low Rf diastereomer | High Rf diastereomer |
|---|---|---|
| (structure with cyclopentanone, HO, OH, benzothiophene, CO₂CH₃) | 72 | 73 |
| (structure with cyclopentanone, HO, OH, benzothiophene, CO₂H) | 74 | 75 |

In a further embodiment, the compound has a structure of compound 1, 2, 3, 4, or 5.

Compound 1

Compound 2

Compound 3

Compound 4

Compound 5

In a yet further embodiment, the compound has a structure of compound 6.

Compound 6

Other aspects of the present specification provide, in part, a composition comprising a compound having the structure of formula VI

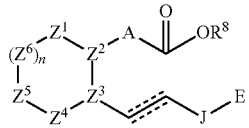

VI wherein each dashed line represents the presence or absence of a bond; $Z^2$ and $Z^3$ are independently CH or N; $Z^1$, $Z^4$, $Z^5$, and $Z^6$ are each independently $CR^9$, $CHR^9$, NH, O, or S; A is —$(CH_2)_6$—, or cis —$CH_2CH=CH$—$(CH_2)_3$—, wherein 1 or 2 carbons may be substituted with S or O; or A is —$(CH_2)_m$—Ar—$(CH_2)_o$— wherein Ar is optionally substituted aryl or optionally substituted heteroaryl, the sum of m and o is from 1, 2, 3, or 4, and wherein one $CH_2$ may be substituted with S or O; $R^8$ is H, hydrocarbyl, or hydrocarbyl-OH; $R^9$ is independently H, $C_{1-6}$ alkyl, OH, F, Cl, Br, I, or O; J is $C_{1-6}$ alkyl, $C_{1-6}$—O-alkyl, C=O, or CHOH; E is $C_{1-12}$ alkyl, $R^{10}$, or —Y—$R^{10}$ wherein Y is $CH_2$, S, or O, and $R^{10}$ is optionally substituted aryl or optionally substituted heteroaryl; and n is 0 or 1.

Methods of preparing the compounds represented by formula VI can be found in, e.g., Maruyama and Ohuchida, 5-Thia-ω-Substituted Phenyl-Prostaglandin E Derivatives, Process for Producing the Same and Drugs Containing the Same as the Active Ingredient, U.S. Pat. No. 6,462,081; Cameron and Lefker, EP4 Receptor Selective Agonists in the Treatment of Osteoporosis, U.S. Pat. No. 6,552,067; Maruyama, et al., Pharmaceutical Composition for Treatment of Diseases Associated with Decrease in Bone Mass Comprising EP4 Agonist as the Active Ingredient, U.S. Pat. No. 7,608,637; Ogidigben, et al., Method for Treating Ocular Hypertension, U.S. Patent Publication 2004/0254230; Kuwahara, et al., Preventive and/or Remedy for Hyperkalemia Containing EP4 Agonist, U.S. Patent Publication 2008/0234337; Takigawa, et al., Cytotoxic T Cell Activator Comprising EP4 Agonist, U.S. Patent Publication 2010/0216689; and Ono, et al., Prostaglandin Derivative, WO 2006/137472; each of which is incorporated by reference in its entirety.

In another embodiment, the compound has the structure of formula VII,

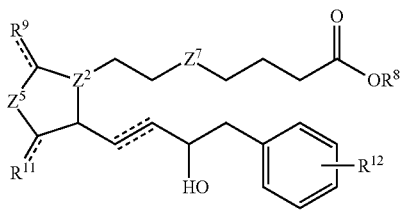

VII wherein each dashed line represents the presence or absence of a bond; $Z^2$ is CH or N; $Z^5$ is $CH_2$, NH, O, or S; $Z^7$ is $CH_2$, O, or S; $R^8$ is H, $C_{1-6}$ hydrocarbyl, or $C_{1-6}$ hydrocarbyl-OH; $R^9$ and $R^{11}$ are independently $C_{1-6}$ alkyl, OH, F, Cl, Br, I, or O; and $R^{12}$ is H, OH, O, F, Cl, Br, I, $C_{1-4}$—O-alkyl, $C_{1-4}$ haloalkyl, or aryl.

In another embodiment, the compound has the structure of formula VIII,

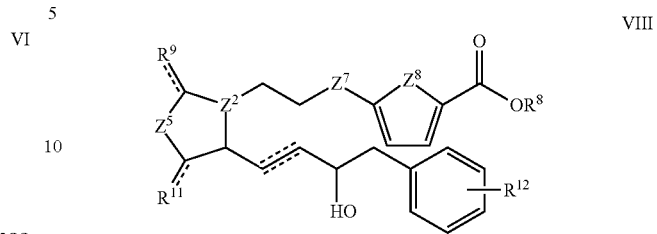

VIII wherein each dashed line represents the presence or absence of a bond; $Z^2$ is CH or N; and $Z^5$ is $CH_2$, NH, O, or S; $Z^7$ and $Z^8$ are independently $CH_2$, O, or S; $R^8$ is H, $C_{1-6}$ hydrocarbyl, or $C_{1-6}$ alkyl-OH; $R^9$ and $R^{11}$ are independently $C_{1-6}$ alkyl, OH, F, Cl, Br, I, or O; and $R^{12}$ is H, OH, O, F, Cl, Br, I, $C_{1-4}$—O-alkyl, $C_{1-4}$ haloalkyl, or aryl.

In an aspect of this embodiment, the compound has a structure of compound 6, 7, 8, 9, 10, 11, 12, or 13.

Compound 6

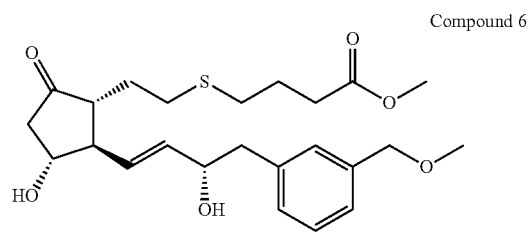

Compound 7

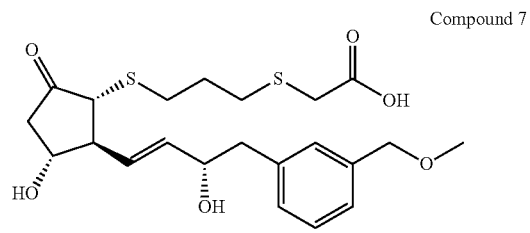

Compound 8

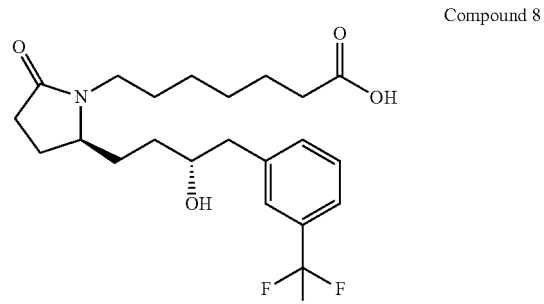

Compound 9

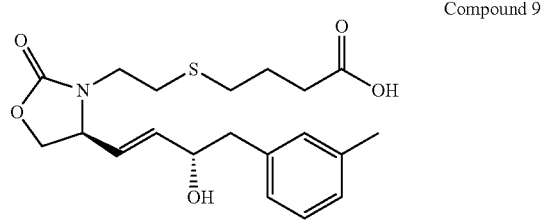

-continued

Compound 10

Compound 11

Compound 12

Compound 13

Other aspects of the present specification provide, in part, a composition comprising a compound having the structure of formula IX

IX wherein $X^1$ and $X^5$ are independently CH or N; $X^7$ is NH, O, or S; $X^8$ and $X^9$ are independently CH or N; $R^{13}$ is optionally substituted aryl or optionally substituted heteroaryl; and $R^{14}$ is $C_{1-6}$ alkyl, optionally substituted aryl, or optionally substituted heteroaryl.

Methods of preparing the compounds represented by formula IX can be found in, e.g., Linders, et al., Bicyclic Derivatives as EP4 Agonists, WO 2008/092860; Linders, et al., Bicyclic Derivatives as EP4 Agonists, WO 2008/092861; and Linders, et al., Bicyclic Derivatives as EP4 Agonists, WO 2008/092862; each of which is incorporated by reference in its entirety.

In another embodiment, the compound has the structure of formula X,

X wherein $X^{10}$, $X^{12}$, $X^{13}$, $X^{14}$, and $X^{15}$ are each independently $CR^{19}$ or N; $R^{16}$ is independently H, OH, O, F, Cl, Br, I, $C_{1-6}$ alkyl, $C_{1-6}$—O-alkyl, CN, or $C_{1-6}$ alkyl-CN; and $R^{19}$ is independently H, OH, O, F, Cl, Br, I, $C_{1-10}$ alkyl, $C_{1-10}$—O-alkyl, or $C_{4-10}$—O-alkyl-heterocyclyl. In an aspect of this embodiment, the $C_{4-10}$ O-alkyl-heterocyclyl is In another embodiment, the compound has the structure of formula XI,

XI wherein $X^{14}$ is $CR^{19}$ or N; $R^{16}$, $R^{17}$, and $R^{18}$ are each independently H, OH, O, F, Cl, Br, I, $C_{1-6}$ alkyl, $C_{1-6}$—O-alkyl, CN, or $C_{1-6}$ alkyl-CN; $R^{19}$ is H, OH, O, or F, Cl, Br, I, $C_{1-10}$ alkyl, $C_{1-10}$—O-alkyl, or and
$R^{20}$ is H, F, Cl, Br, or I.

In another embodiment, the compound has a structure of compound 14, 15, 16, 17, 18, 19, 20, 21, 22, or 23, a pharmaceutically acceptable salt thereof, or a pharmaceutically acceptable amine salt thereof.

Compound 14
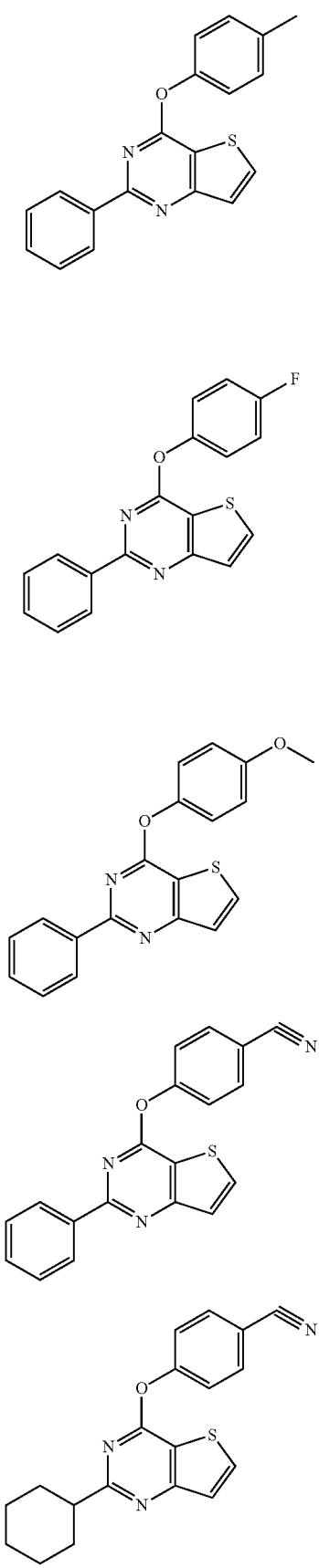
Compound 15
Compound 16
Compound 17
Compound 18
Compound 19
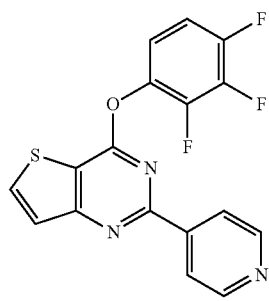
Compound 20
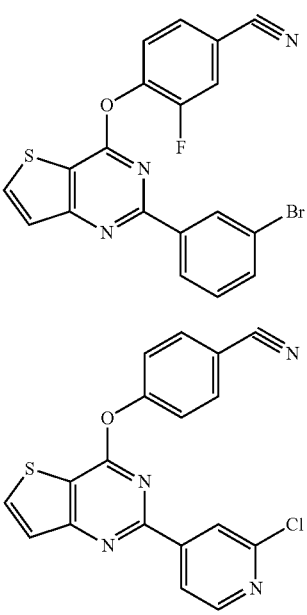
Compound 21
Compound 22
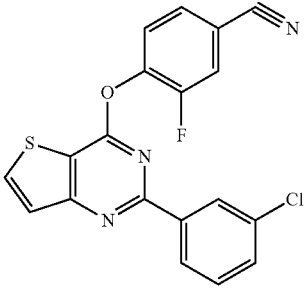
Compound 23
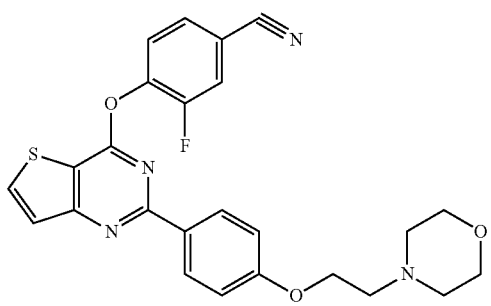
Other aspects of the present specification provide, in part, a composition comprising a compound having the structure of compound 24, a pharmaceutically acceptable salt thereof, or a pharmaceutically acceptable amine salt thereof. In aspects of this embodiment, a pharmaceutically acceptable salt is a sodium salt and a potassium salt. In other aspects of this embodiment, a pharmaceutically acceptable amine salt is an aminoglycoside salt and a triethanolamine salt.

Compound 24

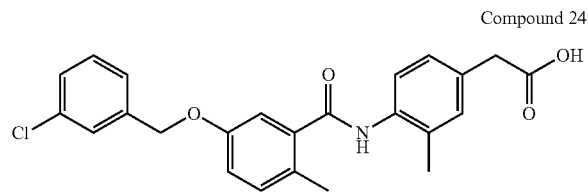 [SMILES: Cc1cc(CC(=O)O)ccc1NC(=O)c1cc(OCc2cccc(Cl)c2)ccc1C]

Methods of preparing the compounds represented by compound 24 can be found in, e.g., Keel and Vallance, Novel Salts of (4-{[(5-{[(3-Chlorophenyl)Methyl]Oxy}-2-Methylphenyl)Carbonyl]Amino}-3-Methylphenyl)Acetic Acid, U.S. patent application Ser. No. 12/997,062 filed Dec. 9, 2010 is a national phase application of WO 2009/150118 (PCT/EP09/57007) filed on Jun. 8, 2009; which is incorporated by reference in its entirety.

The compositions disclosed herein may optionally comprise any number and combination of compounds disclosed herein. For instance, a composition can comprise, e.g., two or more compounds, three or more compounds, four or more compounds or five or more compounds.

Aspects of the present specification provide, in part, a hydrogel material comprising a glycosaminoglycan polymer. The hydrogel material disclosed herein can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan polymer is useful in the hydrogel materials disclosed herein with the proviso that the glycosaminoglycan polymer improves a condition of the skin. Non-limiting examples of glycosaminoglycans include chondroitin sulfate, dermatan sulfate, keratan sulfate, hyaluronan. Non-limiting examples of an acceptable salt of a glycosaminoglycans includes sodium salts, potassium salts, magnesium salts, calcium salts, and combinations thereof. Glycosaminoglycan and their resulting polymers useful in the hydrogel materials and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety. GAGs useful in the hydrogel materials and methods disclosed herein are commercially available, such as, e.g., hyaluronan-based dermal fillers JUVEDERM®, JUVEDERM® 30, JUVEDERM® Ultra, JUVEDERM® Ultra Plus, JUVEDERM® Ultra XC, and JUVEDERM® Ultra Plus XC (Allergan Inc, Irvine, Calif.). Table 2 lists representative GAGs.

TABLE 2

Examples of GAGs

| Name | Hexuronic acid/Hexose | Hexosamine | Glycosidic linkage geometry | Unique features |
| --- | --- | --- | --- | --- |
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |

TABLE 2-continued

Examples of GAGs

| Name | Hexuronic acid/Hexose | Hexosamine | Glycosidic linkage geometry | Unique features |
|---|---|---|---|---|
| Hyaluronan | GlcUA | GlcNAc | -4GlcUAβ1-3GlcNAcβ1- | The only GAG that is exclusively non-sulfated |

GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate Aspects of the present specification provide, in part, a hydrogel material comprising a chondroitin sulfate polymer. As used herein, the term "chondroitin sulfate polymer" refers to an unbranched, sulfated polymer of variable length comprising disaccharides of two alternating monosaccharides of D-glucuronic acid (GlcA) and N-acetyl-D-galactosamine (GalNAc) and pharmaceutically acceptable salts thereof. A chondroitin sulfate polymer may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate polymers are an important structural component of cartilage and provide much of its resistance to compression. Any chondroitin sulfate polymer is useful in the hydrogel materials disclosed herein with the proviso that the chondroitin sulfate polymer improves a condition of the skin. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a hydrogel material comprising a keratan sulfate polymer. As used herein, the term "keratan sulfate polymer" refers to a polymer of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-Acetylneuraminic acid caps the end of the chains. Any keratan sulfate polymer is useful in the hydrogel materials disclosed herein with the proviso that the keratan sulfate polymer improves a condition of the skin. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a hydrogel material comprising a hyaluronan polymer. As used herein, the term "hyaluronic acid polymer" is synonymous with "HA polymer", "hyaluronic acid polymer", and "hyaluronate polymer" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Any hyaluronan polymer is useful in the hydrogel materials disclosed herein with the proviso that the hyaluronan improves a condition of the skin. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a hydrogel material comprising a crosslinked glycosaminoglycan polymer. As used herein, the term "crosslinked" refers to the intermolecular bonds joining the individual polymer molecules, or monomer chains, into a more stable structure like a gel. As such, a crosslinked glycosaminoglycan polymer has at least one intermolecular bond joining at least one individual polymer molecule to another one. The crosslinking of glycosaminoglycan polymers typically result in the formation of a hydrogel. Such hydrogels have high viscosity and require considerable force to extrude through a fine needle. Glycosaminoglycan polymers disclosed herein may be crosslinked using dialdehydes and disulfides crosslinking agents including, without limitation, multifunctional PEG-based crosslinking agents, divinyl sulfones, diglycidyl ethers, and bis-epoxides. Non-limiting examples of hyaluronan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), biscarbodiimide (BCD), adipic dihydrazide (ADH), bis(sulfosuccinimidyl) suberate (BS), hexamethylenediamine (NMDA), 1-(2,3-epoxypropyl)-2,3-epoxycyclohexane, or combinations thereof. Other useful cross-linking agents are disclosed in Stroumpoulis and Tezel, Tunably Crosslinked Polysaccharide Compositions, U.S. patent application Ser. No. 12/910,466, filed Oct. 22, 2010, which is incorporated by reference in its entirety. Non-limiting examples of methods of crosslinking glycosaminoglycan polymers are described in, e.g., Glycosaminoglycan polymers useful in the hydrogel materials and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels and Polysaccharides and Hydrogels thus Obtained, U.S. Patent Publication 2006/0194758; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Di Napoli, Composition and Method for Intradermal Soft Tissue Augmentation, International Patent Publication WO 2004/073759, each of which is hereby incorporated by reference in its entirety.

In an embodiment, a hydrogel material comprises a crosslinked glycosaminoglycan polymer where the crosslinked glycosaminoglycan polymer is present in an amount sufficient to improve a skin condition as disclosed herein. In aspect of this embodiment, a hydrogel material comprises a crosslinked chondroitin sulfate polymer, a crosslinked dermatan sulfate polymer, a crosslinked keratan sulfate polymer, a crosslinked heparan polymer, a crosslinked heparan sulfate polymer, or a crosslinked hyaluronan polymer. In other aspects of this embodiment, a hydrogel material comprises a crosslinked glycosaminoglycan where the crosslinked glycosaminoglycan represents, e.g., about 1% by weight, about 2% by weight, about 3% by weight, about 4% by weight, about 5% by weight, about 6% by weight, about 7% by weight, about 8% by weight, or about 9%, or about 10% by weight, of the total glycosaminoglycan present in the hydrogel material. In yet other aspects of this embodiment, a hydrogel material comprises a crosslinked glycosaminoglycan where the crosslinked glycosaminoglycan represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total glycosaminoglycan present in the hydrogel material. In still other aspects of this embodiment, a hydrogel material comprises a crosslinked glycosaminoglycan where the crosslinked glycosaminoglycan represents, e.g., about 0% to about 10% by weight, about 1% to about 10% by weight, about 3% to about 10% by weight, or about 5% to about 10% by weight, of the total glycosaminoglycan present in the hydrogel material.

In aspects of this embodiment, a hydrogel material comprises a crosslinked glycosaminoglycan where the crosslinked glycosaminoglycan is present at a concentration of, e.g., about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, or about 20 mg/mL. In other aspects of this embodiment, a hydrogel material comprises a crosslinked glycosaminoglycan where the crosslinked glycosaminoglycan is present at a concentration of, e.g., at least 1 mg/mL, at least 2 mg/mL, at least 3 mg/mL, at least 4 mg/mL, at least 5 mg/mL, at least 10 mg/mL, at least 15 mg/mL, at least 20 mg/mL, or at least 25 mg/mL. In yet other aspects of this embodiment, a hydrogel material comprises a crosslinked glycosaminoglycan where the crosslinked glycosaminoglycan is present at a concentration of, e.g., at most 1 mg/mL, at most 2 mg/mL, at most 3 mg/mL, at most 4 mg/mL, at most 5 mg/mL, at most 10 mg/mL, at most 15 mg/mL, at most 20 mg/mL, or at most 25 mg/mL. In still other aspects of this embodiment, a hydrogel material comprises a crosslinked glycosaminoglycan where the crosslinked glycosaminoglycan is present at a concentration of, e.g., about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

Aspects of the present specification provide, in part, a hydrogel material comprising hyaluronan polymers of low molecular weight, hyaluronan polymers of high molecular weight, or hyaluronan polymers of both low and high molecular weight. As used herein, the term "high molecular weight" when referring to "hyaluronan" refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. As used herein, the term "low molecular weight" when referring to "hyaluronan" refers to hyaluronan polymers having a mean molecular weight of less than 1,000,000 Da. Non-limiting examples of a low molecular weight hyaluronan polymers include hyaluronan polymers of about 200,000 Da, about 300,000 Da, about 400,000 Da, about 500,000 Da, about 600,000 Da, about 700,000 Da, of about 800,000 Da, and about 900,000 Da.

In an embodiment, a hydrogel material comprises crosslinked hyaluronan polymers of low molecular weight. In aspects of this embodiment, a hydrogel material comprises crosslinked hyaluronan polymers having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a hydrogel material comprises crosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000. In still other aspects of this embodiment, a hydrogel material comprises crosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a hydrogel material comprises crosslinked hyaluronan polymers of high molecular weight. In aspects of this embodiment, a hydrogel material comprises a crosslinked hyaluronan polymers having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a hydrogel material comprises a crosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a hydrogel material comprises a crosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

In yet another embodiment, a hydrogel material comprises a crosslinked hyaluronan polymers where the crosslinked hyaluronan polymers comprise a combination of both high molecular weight hyaluronan polymers and low molecular weight hyaluronan polymers, in various ratios. In aspects of this embodiment, a hydrogel material comprises a crosslinked hyaluronan polymers where the crosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel material comprising a crosslinked glycosaminoglycan polymer having a degree of crosslinking. As used herein, the term "degree of crosslinking" refers to the percentage of glycosaminoglycan polymer monomeric units, such as, e.g., the disaccharide monomer units of hyaluronan that are bound to a cross-linking agent. The degree of crosslinking is expressed as the percent weight ratio of the crosslinking agent to glycosaminoglycan monomeric unit within the crosslinked portion of the hydrogel material. It is measured by the weight ratio of glycosaminoglycan monomers to crosslinker. Thus, a hydrogel material that that has a crosslinked glycosaminoglycan polymer with a 4% degree of crosslinking means that on average there are four crosslinking molecules for every 100 glycosaminoglycan monomeric units. Every other parameter being equal, the greater the degree of crosslinking, the harder the hydrogel becomes. Non-limiting examples of a degree of crosslinking useful to make the hydrogel materials disclosed herein include about 1% to about 15%.

In aspects of this embodiment, a hydrogel material comprises a crosslinked glycosaminoglycan where the degree of crosslinking is about 1%, about 2%, about 3%, about 4%, about 5%, about 6%, about 7%, about 8%, about 9%, about 10%, about 11%, about 12%, about 13%, about 14%, or about 15%. In yet other aspects of this embodiment, a hydrogel material comprises a crosslinked glycosaminoglycan where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In still other aspects of this embodiment, a hydrogel material comprises a crosslinked glycosaminoglycan where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%.

Aspects of the present specification provide, in part, a hydrogel material comprising an uncrosslinked glycosaminoglycan polymer. As used herein, the term "uncrosslinked" refers to a lack of intermolecular bonds joining the individual glycosaminoglycan polymer molecules, or monomer chains. As such, an uncrosslinked glycosaminoglycan polymer is not linked to any other glycosaminoglycan polymer by an intermolecular bond. In aspects of this embodiment, a hydrogel material comprises an uncrosslinked chondroitin sulfate polymer, an uncrosslinked dermatan sulfate polymer, an uncrosslinked keratan sulfate polymer, an uncrosslinked heparan polymer, an uncrosslinked heparan sulfate polymer, or an uncrosslinked hyaluronan polymer. Uncrosslinked glycosaminoglycan polymers are water soluble and generally remain fluid in nature. As such, uncross-linked glycosaminoglycan polymers are often mixed with a glycosaminoglycan polymer-based hydrogel material as a lubricant to facilitate the extrusion process of the hydrogel material through a fine needle.

In an embodiment, a hydrogel material comprises an uncrosslinked glycosaminoglycan polymer where the uncrosslinked glycosaminoglycan polymer is present in an amount sufficient to improve a skin condition as disclosed herein. In aspects of this embodiment, a hydrogel material comprises an uncrosslinked glycosaminoglycan where the uncrosslinked glycosaminoglycan is present at a concentration of, e.g., about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 13.5 mg/mL, about 14 mg/mL, about 15 mg/mL, about 16 mg/mL, about 17 mg/mL, about 18 mg/mL, about 19 mg/mL, about 20 mg/mL, about 40 mg/mL, or about 60 mg/mL. In other aspects of this embodiment, a hydrogel material comprises an uncrosslinked glycosaminoglycan where the uncrosslinked glycosaminoglycan is present at a concentration of, e.g., at least 1 mg/mL, at least 2 mg/mL, at least 3 mg/mL, at least 4 mg/mL, at least 5 mg/mL, at least 10 mg/mL, at least 15 mg/mL, at least 20 mg/mL, at least 25 mg/mL at least 35 mg/mL, or at least 40 mg/mL. In yet other aspects of this embodiment, a hydrogel material comprises an uncrosslinked glycosaminoglycan where the uncrosslinked glycosaminoglycan is present at a concentration of, e.g., at most 1 mg/mL, at most 2 mg/mL, at most 3 mg/mL, at most 4 mg/mL, at most 5 mg/mL, at most 10 mg/mL, at most 15 mg/mL, at most 20 mg/mL, or at most 25 mg/mL. In still other aspects of this embodiment, a hydrogel material comprises an uncrosslinked glycosaminoglycan where the uncrosslinked glycosaminoglycan is present at a concentration of, e.g., about 1 mg/mL to about 60 mg/mL, about 10 mg/mL to about 40 mg/mL, about 7.5 mg/mL to about 19.5 mg/mL, about 8.5 mg/mL to about 18.5 mg/mL, about 9.5 mg/mL to about 17.5 mg/mL, about 10.5 mg/mL to about 16.5 mg/mL, about 11.5 mg/mL to about 15.5 mg/mL, or about 12.5 mg/mL to about 14.5 mg/mL.

In an embodiment, a hydrogel material comprises uncrosslinked hyaluronan polymers of low molecular weight. In aspects of this embodiment, a hydrogel material comprises a uncrosslinked hyaluronan having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a hydrogel material comprises uncrosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000. In still other aspects of this embodiment, a hydrogel material comprises uncrosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a hydrogel material comprises uncrosslinked hyaluronan polymers of high molecular weight. In aspects of this embodiment, a hydrogel material comprises an uncrosslinked hyaluronan having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In other aspects of this embodiment, a hydrogel material comprises an uncrosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In yet other aspects of this embodiment, a hydrogel material comprises an uncrosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In still other aspects, a hydrogel material comprises an uncrosslinked hyaluronan polymers having a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

In another embodiment, a hydrogel material comprises uncrosslinked hyaluronan polymers where the uncrosslinked hyaluronan comprises a combination of both high molecular weight hyaluronan polymers and low molecular weight hyaluronan polymers, in various ratios. In aspects of this embodiment, a hydrogel material comprises an uncrosslinked hyaluronan polymers where the uncrosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel material comprising a substantially uncrosslinked glycosaminoglycan polymer. As sued herein, the term "substantially uncrosslinked" refers to the presence of uncrosslinked glycosaminoglycan polymers in a hydrogel material disclosed herein at a level of at least 90% by weight of the hydrogel material, with the remaining at most 10% by weight of the hydrogel material being comprised of other components including crosslinked glycosaminoglycan polymers. In aspects of this embodiment, a hydrogel material comprises a substantially uncrosslinked chondroitin sulfate polymer, a substantially uncrosslinked dermatan sulfate polymer, a substantially uncrosslinked keratan sulfate polymer, a substantially uncrosslinked heparan polymer, a substantially uncrosslinked heparan sulfate polymer, or a substantially uncrosslinked hyaluronan polymer. In other aspects of this embodiment, a hydrogel material comprises an uncrosslinked glycosaminoglycan where the uncrosslinked glycosaminoglycan represents, e.g., about 90% or more by weight, about 91% or more by weight, about 92% or more by weight, about 93% or more by weight, about 94% or more by weight, about 95% or more by weight, about 96% or more by weight, about 97% or more by weight, about 98% or more by weight, or about 99% or more, or about 100% by weight, of the total glycosaminoglycan present in the hydrogel material. In yet other aspects of this embodiment, a hydrogel material comprises an uncrosslinked glycosaminoglycan where the uncrosslinked glycosaminoglycan represents, e.g., about 90% to about 100% by weight, about 93% to about 100% by weight, about 95% to about 100% by weight, or about 97% to about 100% by weight, of the total glycosaminoglycan present in the hydrogel material.

Aspects of the present specification provide, in part, a hydrogel material that is essentially free of a crosslinked glycosaminoglycan polymer. As used herein, the term "essentially free" (or "consisting essentially of") refers to a hydrogel material where only trace amounts of cross-linked matrix polymers can be detected. In an aspect of this embodiment, a hydrogel material comprises a chondroitin sulfate that is essentially free of a crosslinked chondroitin sulfate polymer, a dermatan sulfate essentially free of a crosslinked dermatan sulfate polymer, a keratan sulfate essentially free of a crosslinked keratan sulfate polymer, a heparan essentially free of a crosslinked heparan polymer, a heparan sulfate essentially free of a crosslinked heparan sulfate polymer, or a hyaluronan sulfate essentially free of a crosslinked hyaluronan polymer.

Aspects of the present specification provide, in part, a hydrogel material that is entirely free of a crosslinked glycosaminoglycan polymer. As used herein, the term "entirely free" refers to a hydrogel material that within the detection range of the instrument or process being used, crosslinked glycosaminoglycan polymers cannot be detected or its presence cannot be confirmed. In an aspect of this embodiment, a hydrogel material comprises a chondroitin sulfate that is entirely free of a crosslinked chondroitin sulfate polymer, a dermatan sulfate entirely free of a crosslinked dermatan sulfate polymer, a keratan sulfate entirely free of a crosslinked keratan sulfate polymer, a heparan entirely free of a crosslinked heparan polymer, a heparan sulfate entirely free of a crosslinked heparan sulfate polymer, or a hyaluronan sulfate entirely free of a crosslinked hyaluronan polymer.

Aspects of the present specification provide, in part, a hydrogel material comprising a ratio of crosslinked glycosaminoglycan polymer and uncrosslinked glycosaminoglycan polymer. This ratio of crosslinked and uncrosslinked glycosaminoglycan polymer is also known as the gel:fluid ratio. Any gel:fluid ratio is useful in making the hydrogel materials disclosed herein with the proviso that such ratio produces a hydrogel material disclosed herein that improves a skin condition as disclosed herein. Non-limiting examples of gel:fluid ratios include 100:0, 98:2, 90:10, 75:25, 70:30, 60:40, 50:50, 40:60, 30:70, 25:75, 10:90; 2:98, and 0:100.

In aspects of this embodiment, a hydrogel material comprises a crosslinked glycosaminoglycan polymer and an uncrosslinked glycosaminoglycan polymer where the gel:fluid ratio is, e.g., about 0:100, about 1:99, about 2:98, about 3:97, about 4:96, about 5:95, about 6:94, about 7:93, about 8:92, about 9:91, or about 10:90. In other aspects of this embodiment, a hydrogel material comprises a crosslinked glycosaminoglycan polymer and an uncrosslinked glycosaminoglycan polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In yet other aspects of this embodiment, a hydrogel material comprises a crosslinked glycosaminoglycan polymer and an uncrosslinked glycosaminoglycan polymer where the gel:fluid ratio is, e.g., about 0:100 to about 3:97, about 0:100 to about 5:95, or about 0:100 to about 10:90.

In other aspects of this embodiment, a hydrogel material comprises a crosslinked glycosaminoglycan polymer and an uncrosslinked glycosaminoglycan polymer where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a hydrogel material comprises a crosslinked glycosaminoglycan polymer and an uncrosslinked glycosaminoglycan polymer where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a hydrogel material comprises a crosslinked glycosaminoglycan polymer and an uncrosslinked glycosaminoglycan polymer where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

A hydrogel material disclosed herein may be formed into a porous material like a sponge. The porous material can serve both as a bulking agent to fill the tissue space as well as a substrate to support tissue growth. A hydrogel material disclosed herein may be processed into a porous material using standard methods known in the art, including, e.g., freeze-drying, gas foaming, and/or negative templating using porogens. The pore size of a porous material can be controlled, e.g., by adjusting the concentration of GAG and the particle size of the porogen. After formation of the porous material, the excess porogen is then extracted, for example, by immersing in water or other suitable solvent. The resultant porous material can then be dried and used. Such methods are described in, e.g., Kaplin, et al., Concentrated Aqueous Silk Fibroin Solution and Use Thereof, U.S. Pat. No. 7,635,755; Ratner and Marshall, Novel Porous Materials, U.S. Patent Publication 2008/0075752; Ma and Chen, Porous Materials having Multi-Sized Geometries, U.S. Patent Publication 2007/0036844; Ma, Reverse Fabrication of Porous Materials, U.S. Patent Publication 2002/0005600; Liu, et al., Porous Materials, Methods of Making and Uses, U.S. Patent Application 61/333,613; and Liu, et al., Porous Materials, Methods of Making and Uses, U.S. Patent Application 61/333,120, LeBreton et al., Dermal Fillers Comprising Silk Fibroin Hydrogels Uses Thereof, U.S. patent application Ser. No. 12/883,139; and, Guang-Liang et al., Drug Delivery Platforms Comprising Silk Fibroin Hydrogels and Uses Thereof, U.S. patent application Ser. No. 12/873,563, each of which is hereby incorporated by reference in its entirety.

A hydrogel material disclosed herein may be formed into solid particles. The hydrogel particles can serve both as a bulking agent to fill the tissue space as well as a substrate to support tissue growth. A hydrogel material is processed into particles simply by manually or mechanically pulverizing the material and optionally mixed with a carrier phase such as, e.g., water or a saline solution to form an injectable or topical substance like a solution, oil, lotion, gel, ointment, cream, slurry, salve, or paste. As such, the disclosed hydrogel materials may be monophasic or multiphasic compositions. A hydrogel may be milled to a particle size from about 10 µm to about 1000 µm in diameter. In aspects of this embodiment, a particle size may be about 15 µm to about 30 µm, about 25 µm to about 50 µm, about 45 µm to about 75 µm, about 70 µm to about 100 µm, about 50 µm to about 200 µm, about 150 µm to about 300 µm, about 250 µm to about 400 µm, about 350 µm to about 500 µm, about 450 µm to about 600 µm, about 550 µm to about 700 µm, about 650 µm to about 800 µm, about 750 µm to about 900 µm, or about 850 µm to about 1000 µm. Saline is then added as a carrier phase by first determining the bulk volume of a hydrogel material, then vigorously pulverizing the hydrogel into particles while incorporating an appropriate volume of saline to achieve a desired carrier to hydrogel particle ratio. For example, hydrogel milling may be accomplished by means of a forced sieving of bulk hydrogel through a series of stainless steel cloth sieves of decreasing pore sizes.

Aspects of the present specification provide, in part, a hydrogel material disclosed herein that exhibits a complex modulus, an elastic modulus, a viscous modulus and/or a tan δ. The compositions as disclosed herein are viscoelastic in that the composition has an elastic component (solid-like such as, e.g., crosslinked glycosaminoglycan polymers) and a viscous component (liquid-like such as, e.g., uncrosslinked glycosaminoglycan polymers or a carrier phase) when a force is applied (stress, deformation). The rheological attribute that described this property is the complex modulus ($G^*$), which defines a composition's total resistance to deformation. The complex modulus is a complex number with a real and imaginary part: $G^*=G'+iG''$. The absolute value of $G^*$ is $\text{Abs}(G^*)=\text{Sqrt}(G'^2+G''^2)$. The complex modulus can be defined as the sum of the elastic modulus ($G'$) and the viscous modulus ($G''$). Falcone, et al., *Temporary Polysaccharide Dermal Fillers: A Model for Persistence Based on Physical Properties*, Dermatol Surg. 35(8): 1238-1243 (2009); Tezel, supra, 2008; Kablik, supra, 2009; Beasley, supra, 2009; each of which is hereby incorporated by reference in its entirety.

Elastic modulus, or modulus of elasticity, refers to the ability of a hydrogel material to resists deformation, or, conversely, an object's tendency to be non-permanently deformed when a force is applied to it. Elastic modulus characterizes the firmness of a composition and is also known as the storage modulus because it describes the storage of energy from the motion of the composition. The elastic modulus describes the interaction between elasticity and strength ($G'$=stress/strain) and, as such, provides a quantitative measurement of a composition's hardness or softness. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Although depending on the speed at which the force is applied, a stiffer composition will have a higher elastic modulus and it will take a greater force to deform the material a given distance, such as, e.g., an injection. Specifying how stresses are to be measured, including directions, allows for many types of elastic moduli to be defined. The three primary elastic moduli are tensile modulus, shear modulus, and bulk modulus.

Viscous modulus is also known as the loss modulus because it describes the energy that is lost as viscous dissipation. Tan δ is the ratio of the viscous modulus and the elastic modulus, tan $\delta=G''/G'$. Falcone, supra, 2009. For tan δ values disclosed in the present specification, a tan δ is obtained from the dynamic modulus at a frequency of 0.628 rad/s. A lower tan δ corresponds to a stiffer, harder, or more elastic composition.

Thus, in an embodiment, a hydrogel material disclosed herein exhibits a complex modulus. In aspects of this embodiment, a hydrogel material exhibits a complex modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, or about 800 Pa. In other aspects of this embodiment, a hydrogel material exhibits a complex modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, or at most 800 Pa. In yet other aspects of this embodiment, a hydrogel material exhibits a complex modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, or about 125 Pa to about 800 Pa.

In another embodiment, a hydrogel material disclosed herein exhibits an elastic modulus. In aspects of this embodiment, a hydrogel material exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, about 1,000 Pa, about 1,200 Pa, about 1,300 Pa, about 1,400 Pa, about 1,500 Pa, about 1,600 Pa, about 1700 Pa, about 1800 Pa, about 1900 Pa, about 2,000 Pa, about 2,100 Pa, about 2,200 Pa, about 2,300 Pa, about 2,400 Pa, or about 2,500 Pa. In other aspects of this embodiment, a hydrogel material exhibits an elastic modulus of, e.g., at least 25 Pa, at least 50 Pa, at least 75 Pa, at least 100 Pa, at least 125 Pa, at least 150 Pa, at least 175 Pa, at least 200 Pa, at least 250 Pa, at least 300 Pa, at least 350 Pa, at least 400 Pa, at least 450 Pa, at least 500 Pa, at least 550 Pa, at least 600 Pa, at least 650 Pa, at least 700 Pa, at least 750 Pa, at least 800 Pa, at least 850 Pa, at least 900 Pa, at least 950 Pa, at least 1,000 Pa, at least 1,200 Pa, at least 1,300 Pa, at least 1,400 Pa, at least 1,500 Pa, at least 1,600 Pa, at least 1700 Pa, at least 1800 Pa, at least 1900 Pa, at least 2,000 Pa, at least 2,100 Pa, at least 2,200 Pa, at least 2,300 Pa, at least 2,400 Pa, or at least 2,500 Pa. In yet other aspects of this embodiment, a hydrogel material exhibits an elastic modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, at most 800 Pa, at most 850 Pa, at most 900 Pa, at most 950 Pa, at most 1,000 Pa, at most 1,200 Pa, at most 1,300 Pa, at most 1,400 Pa, at most 1,500 Pa, or at most 1,600 Pa. In still other aspects of this embodiment, a hydrogel material exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, about 125 Pa to about 800 Pa, about 500 Pa to about 1,600 Pa, about 600 Pa to about 1,600 Pa, about 700 Pa to about 1,600 Pa, about 800 Pa to about 1,600 Pa, about 900 Pa to about 1,600 Pa, about 1,000 Pa to about 1,600 Pa, about 1,100 Pa to about 1,600 Pa, about 1,200 Pa to about 1,600 Pa, about 500 Pa to about 2,500 Pa, about 1,000 Pa to about 2,500 Pa, about 1,500 Pa to about 2,500 Pa, about 2,000 Pa to about 2,500 Pa, about 1,300 Pa to about 1,600 Pa, about 1,400 Pa to about 1,700 Pa, about 1,500 Pa to about 1,800 Pa, about 1,600 Pa to about 1,900 Pa, about 1,700 Pa to about 2,000 Pa, about 1,800 Pa to about 2,100 Pa, about 1,900 Pa to about 2,200 Pa, about 2,000 Pa to about 2,300 Pa, about 2,100 Pa to about 2,400 Pa, or about 2,200 Pa to about 2,500 Pa.

In another embodiment, a hydrogel material disclosed herein exhibits a tensile modulus. In aspects of this embodiment, a hydrogel material exhibits a tensile modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a hydrogel material exhibits a tensile modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a hydrogel material exhibits a tensile modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a hydrogel material disclosed herein exhibits shear modulus. In aspects of this embodiment, a hydrogel material exhibits a shear modulus of, e.g., about 1 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 750 MPa, about 1 GPa, about 5 GPa, about 10 GPa, about 15 GPa, about 20 GPa, about 25 GPa, or about 30 GPa. In other aspects of this embodiment, a hydrogel material exhibits a shear modulus of, e.g., at least 1 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 750 MPa, at least 1 GPa, at least 5 GPa, at least 10 GPa, at least 15 GPa, at least 20 GPa, at least 25 GPa, or at least 30 GPa In yet other aspects of this embodiment, a hydrogel material exhibits a shear modulus of, e.g., about 1 MPa to about 30 MPa, about 10 MPa to about 50 MPa, about 25 MPa to about 75 MPa, about 50 MPa to about 100 MPa, about 100 MPa to about 300 MPa, about 200 MPa to about 400 MPa, about 300 MPa to about 500 MPa, about 100 MPa to about 500 MPa, about 250 MPa to about 750 MPa, about 500 MPa to about 1 GPa, about 1 GPa to about 30 GPa, about 10 GPa to about 30 GPa.

In another embodiment, a hydrogel material disclosed herein exhibits a bulk modulus. In aspects of this embodiment, a hydrogel material exhibits a bulk modulus of, e.g., about 5 GPa, about 6 GPa, about 7 GPa, about 8 GPa, about 9 GPa, about 10 GPa, about 15 GPa, about 20 GPa, about 25 GPa, about 30 GPa, about 35 GPa, about 40 GPa, about 45 GPa, about 50 GPa, about 60 GPa, about 70 GPa, about 80 GPa, about 90 GPa, about 100 GPa. In other aspects of this embodiment, a hydrogel material exhibits a bulk modulus of, e.g., at least 5 GPa, at least 6 GPa, at least 7 GPa, at least 8 GPa, at least 9 GPa, at least 10 GPa, at least 15 GPa, at least 20 GPa, at least 25 GPa, at least 30 GPa, at least 35 GPa, at least 40 GPa, at least 45 GPa, at least 50 GPa, at least 60 GPa, at least 70 GPa, at least 80 GPa, at least 90 GPa, at least 100 GPa. In yet other aspects of this embodiment, a hydrogel material exhibits a bulk modulus of, e.g., about 5 GPa to about 50 GPa, about 5 GPa to about 100 GPa, about 10 GPa to about 50 GPa, about 10 GPa to about 100 GPa, or about 50 GPa to about 100 GPa.

In another embodiment, a hydrogel material disclosed herein exhibits a viscous modulus. In aspects of this embodiment, a hydrogel material exhibits a viscous modulus of, e.g., about 10 Pa, about 20 Pa, about 30 Pa, about 40 Pa, about 50

Pa, about 60 Pa, about 70 Pa, about 80 Pa, about 90 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, or about 700 Pa. In other aspects of this embodiment, a hydrogel material exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, at most 150 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, or at most 700 Pa. In yet other aspects of this embodiment, a hydrogel material exhibits a viscous modulus of, e.g., about 10 Pa to about 30 Pa, about 10 Pa to about 50 Pa, about 10 Pa to about 100 Pa, about 10 Pa to about 150 Pa, about 70 Pa to about 100 Pa, about 50 Pa to about 350 Pa, about 150 Pa to about 450 Pa, about 250 Pa to about 550 Pa, about 350 Pa to about 700 Pa, about 50 Pa to about 150 Pa, about 100 Pa to about 200 Pa, about 150 Pa to about 250 Pa, about 200 Pa to about 300 Pa, about 250 Pa to about 350 Pa, about 300 Pa to about 400 Pa, about 350 Pa to about 450 Pa, about 400 Pa to about 500 Pa, about 450 Pa to about 550 Pa, about 500 Pa to about 600 Pa, about 550 Pa to about 650 Pa, or about 600 Pa to about 700 Pa.

In another embodiment, a hydrogel material disclosed herein exhibits a tan δ. In aspects of this embodiment, a hydrogel material exhibits a tan δ of, e.g., about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In other aspects of this embodiment, a hydrogel material exhibits a tan δ of, e.g., at most 0.1, at most 0.2, at most 0.3, at most 0.4, at most 0.5, at most 0.6, at most 0.7, at most 0.8, at most 0.9, at most 1.0, at most 1.1, at most 1.2, at most 1.3, at most 1.4, at most 1.5, at most 1.6, at most 1.7, at most 1.8, at most 1.9, at most 2.0, at most 2.1, at most 2.2, at most 2.3, at most 2.4, or at most 2.5. In yet other aspects of this embodiment, a hydrogel material exhibits a tan δ of, e.g., about 0.1 to about 0.3, about 0.3 to about 0.5, about 0.5 to about 0.8, about 1.1 to about 1.4, about 1.4 to about 1.7, about 0.3 to about 0.6, about 0.1 to about 0.5, about 0.5 to about 0.9, about 0.1 to about 0.6, about 0.1 to about 1.0, about 0.5 to about 1.5, about 1.0 to about 2.0, or about 1.5 to about 2.5.

Aspects of the present specification provide, in part, a hydrogel material disclosed herein having hardness. Hardness refers to various properties of an object in the solid phase that gives it high resistance to various kinds of shape change when force is applied. Hardness is measured using a durometer and is a unitless value that ranges from zero to 100. The ability or inability of a hydrogel to be easily compressed will affect its suitability for application in different tissue replacement roles, i.e., mechanical compliance as bone, fat, connective tissue. Hardness will also affect the ability of a hydrogel to be effectively comminuted, the reason being that a hard material may be more easily and consistently comminuted. Hardness will also affect extrudability, as a soft material may be more readily able to be slightly compressed during injection to pack with other particles or change shape to pass through a syringe barrel or needle.

In an embodiment, a hydrogel material disclosed herein exhibits low hardness. In aspects of this embodiment, a hydrogel material exhibits a hardness of, e.g., about 5, about 10, about 15, about 20, about 25, about 30, or about 35. In other aspects of this embodiment, a hydrogel material exhibits a hardness of, e.g., at most 5, at most 10, at most 15, at most 20, at most 25, at most 30, or at most 35. In yet other aspects of this embodiment, a hydrogel material exhibits a hardness of, e.g., about 5 to about 35, about 10 to about 35, about 15 to about 35, about 20 to about 35, or about 25 to about 35, about 5 to about 40, about 10 to about 40, about 15 to about 40, about 20 to about 40, about 25 to about 40, or about 30 to about 40.

In an embodiment, a hydrogel material disclosed herein exhibits medium hardness. In aspects of this embodiment, a hydrogel material exhibits a hardness of, e.g., about 40, about 45, about 50, about 55, or about 60. In other aspects of this embodiment, a hydrogel material exhibits a hardness of, e.g., at least 40, at least 45, at least 50, at least 55, or at least 60. In yet other aspects of this embodiment, a hydrogel material exhibits a hardness of, e.g., at most 40, at most 45, at most 50, at most 55, or at most 60. In still other aspects of this embodiment, a hydrogel material exhibits a hardness of, e.g., about 35 to about 60, about 35 to about 55, about 35 to about 50, about 35 to about 45, about 40 to about 60, about 45 to about 60, about 50 to about 60, about 55 to about 60, about 40 to about 65, about 45 to about 65, about 50 to about 65, about 55 to about 65.

In another embodiment, a hydrogel material disclosed herein exhibits high hardness. In aspects of this embodiment, a hydrogel material exhibits a hardness of, e.g., about 65, about 70, about 75, about 80, about 85, about 90, about 95, or about 100. In other aspects of this embodiment, a hydrogel material exhibits a hardness of, e.g., at least 65, at least 70, at least 75, at least 80, at least 85, at least 90, at least 95, or at least 100. In yet other aspects of this embodiment, a hydrogel material exhibits a hardness of, e.g., about 65 to about 100, about 70 to about 100, about 75 to about 100, about 80 to about 100, about 85 to about 100, about 90 to about 100, about 65 to about 75, about 65 to about 80, about 65 to about 85, about 65 to about 90, about 65 to about 95, about 60 to about 75, about 60 to about 80, about 60 to about 85, about 60 to about 90, or about 60 to about 95.

In an embodiment, a hydrogel material disclosed herein exhibits high resistant to deformation. In aspects of this embodiment, a hydrogel material exhibits resistant to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a hydrogel material exhibits resistant to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a hydrogel material exhibits resistant to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a hydrogel material exhibits resistant to deformation of, e.g., about 85% to about 100%, about 87% to about 100%, about 90% to about 100%, about 93% to about 100%, about 95% to about 100%, or about 97% to about 100%.

A hydrogel material disclosed herein exhibits high tensile strength. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a hydrogel material disclosed herein exhibits high yield strength relative to other polymer classes. In aspects of this embodiment, a silk fibroin material exhibits a yield strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a hydrogel material exhibits a yield strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a hydrogel material exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a hydrogel material exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a hydrogel material disclosed herein exhibits high ultimate strength. In aspects of this embodiment, a hydrogel material exhibits an ultimate strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a hydrogel material exhibits an ultimate strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a hydrogel material exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a hydrogel material exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

In another embodiment, a hydrogel material disclosed herein exhibits high breaking strength. In aspects of this embodiment, a hydrogel material exhibits a breaking strength of, e.g., about 0.1 MPa, about 0.5 MPa, about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa. In other aspects of this embodiment, a hydrogel material exhibits a breaking strength of, e.g., at least 0.1 MPa, at least 0.5 MPa, at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa. In yet other aspects of this embodiment, a hydrogel material exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a hydrogel material exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 10 MPa to about 200 MPa, about 10 MPa to about 300 MPa, or about 100 MPa to about 300 MPa.

Aspects of the present specification provide, in part, a hydrogel material disclosed herein having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, polymer concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a hydrogel material disclosed herein is optically transparent. In aspects of this embodiment, a hydrogel material transmits, e.g., about 75% of the light, about 80% of the light, about 85% of the light, about 90% of the light, about 95% of the light, or about 100% of the light. In other aspects of this embodiment, a hydrogel material transmits, e.g., at least 75% of the light, at least 80% of the light, at least 85% of the light, at least 90% of the light, or at least 95% of the light. In yet other aspects of this embodiment, a hydrogel material transmits, e.g., about 75% to about 100% of the light, about 80% to about 100% of the light, about 85% to about 100% of the light, about 90% to about 100% of the light, or about 95% to about 100% of the light.

In another embodiment, a hydrogel material disclosed herein is optically opaque. In aspects of this embodiment, a hydrogel material transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a hydrogel material transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a hydrogel material transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In an embodiment, a hydrogel material disclosed herein is optically translucent. In aspects of this embodiment, a hydrogel material diffusely transmits, e.g., about 75% of the light, about 80% of the light, about 85% of the light, about 90% of the light, about 95% of the light, or about 100% of the light. In other aspects of this embodiment, a hydrogel material diffusely transmits, e.g., at least 75% of the light, at least 80% of the light, at least 85% of the light, at least 90% of the light, or at least 95% of the light. In yet other aspects of this embodiment, a hydrogel material diffusely transmits, e.g., about 75% to about 100% of the light, about 80% to about 100% of the light, about 85% to about 100% of the light, about 90% to about 100% of the light, or about 95% to about 100% of the light.

Aspects of the present specification provide, in part, a hydrogel material disclosed herein that exhibits a dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity ($\mu$, although $\eta$ is sometimes used) or kinematic viscosity ($v$). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pa·s), which is identical to N·m−2·s. Dynamic viscosity can be expressed as $\tau=\mu dvx/dz$, where $\tau$=shearing stress, $\mu$=dynamic viscosity, and dvx/dz is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Dynamic viscosity symbolize by is also used, is measured with various types of rheometers, devices used to measure the way in which a liquid, suspension or slurry flows in response to applied forces.

Kinematic viscosity ($v$) is the ratio of dynamic viscosity to density, a quantity in which no force is involved and is defined as follows: $v=\mu/\rho$, where $\mu$ is the dynamic viscosity $\rho$ is density with the SI unit of $kg/m^3$. Kinematic viscosity is usually measured by a glass capillary viscometer as has an SI unit of $m^2/s$.

The viscosity of a material is highly temperature dependent and for either dynamic or kinematic viscosity to be meaningful, the reference temperature must be quoted. For the viscosity values disclosed herein, a dynamic viscosity is measured at 1 Pa with a cone/plane geometry 2°/40 cm and a temperature of 20° C. Examples of the dynamic viscosity of various fluids at 20° C. is as follows: water is about $1.0 \times 10^{-3}$ Pa·s, blood is about $3-4 \times 10^{-3}$ Pa·s, vegetable oil is about $60-85 \times 10^{-3}$ Pa·s, motor oil SE 30 is about 0.2 Pa·s, glycerin is about 1.4 Pa·s, maple syrup is about 2-3 Pa·s, honey is about 10 Pa·s, chocolate syrup is about 10-25 Pa·s, peanut butter is about 150-250 Pa·s, lard is about 1,000 Pa·s, vegetable shortening is about 1,200 Pa·s, and tar is about 30,000 Pa·s.

In aspects of this embodiment, a hydrogel material disclosed herein exhibits a dynamic viscosity of, e.g., about 10 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 125 Pa·s, about 150 Pa·s, about 175 Pa·s, about 200 Pa·s, about 225 Pa·s, about 250 Pa·s, about 275 Pa·s, about 300 Pa·s, about 400 Pa·s, about 500 Pa·s, about 600 Pa·s, about 700 Pa·s, about 750 Pa·s, about 800 Pa·s, about 900 Pa·s, about 1,000 Pa·s, about 1,100 Pa·s, or about 1,200 Pa·s. In other aspects of this embodiment, a hydrogel material disclosed herein exhibits a dynamic viscosity of, e.g., at most 10 Pa·s, at most 20 Pa·s, at most 30 Pa·s, at most 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, at most 175 Pa·s, at most 200 Pa·s, at most 225 Pa·s, at most 250 Pa·s, at most 275 Pa·s, at most 300 Pa·s, at most 400 Pa·s, at most 500 Pa·s, at most 600 Pa·s, at most 700 Pa·s, at most 750 Pa·s, at most 800 Pa·s, at most 900 Pa·s, or at most 1000 Pa·s. In yet other aspects of this embodiment, a hydrogel material disclosed herein exhibits a dynamic viscosity of, e.g., about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

Aspects of the present specification provide, in part, a hydrogel material disclosed herein that exhibits cohesivity. Cohesivity, also referred to as cohesion cohesive attraction, cohesive force, or compression force is a physical property of a material, caused by the intermolecular attraction between like-molecules within the material that acts to unite the molecules. Cohesivity is expressed in terms of grams-force (gmf). Cohesiveness is affected by, among other factors, the molecular weight ratio of the initial free glycosaminoglycan polymer, the degree of crosslinking of glycosaminoglycan polymers, the amount of residual free glycosaminoglycan polymers following crosslinking, and the pH of the hydrogel material. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a hydrogel material disclosed herein exhibits cohesivity, on par with water. In yet another embodiment, a hydrogel material disclosed herein exhibits sufficient cohesivity to remain localized to a site of administration. In still another embodiment, a hydrogel material disclosed herein exhibits sufficient cohesivity to retain its shape. In a further embodiment, a hydrogel material disclosed herein exhibits sufficient cohesivity to retain its shape and functionality.

In aspects of this embodiment, a hydrogel material disclosed herein has a cohesivity of, e.g., about 10 gmf, about 20 gmf, about 30 gmf, about 40 gmf, about 50 gmf, about 60 gmf, about 70 gmf, about 80 gmf, about 90 gmf, about 100 gmf, about 150 gmf, or about 200 gmf. In other aspects of this embodiment, a hydrogel material disclosed herein has a cohesivity of, e.g., at least 10 gmf, at least 20 gmf, at least 30 gmf, at least 40 gmf, at least 50 gmf, at least 60 gmf, at least 70 gmf, at least 80 gmf, at least 90 gmf, at least 100 gmf, at least 150 gmf, or at least 200 gmf. In yet other aspects of this embodiment, a hydrogel material disclosed herein has a cohesivity of, e.g., at most 10 gmf, at most 20 gmf, at most 30 gmf, at most 40 gmf, at most 50 gmf, at most 60 gmf, at most 70 gmf, at most 80 gmf, at most 90 gmf, at most 100 gmf, at most 150 gmf, or at most 200 gmf. In yet other aspects of this embodiment, a hydrogel material disclosed herein has a cohesivity of, e.g., about 50 gmf to about 150 gmf, about 60 gmf to about 140 gmf, about 70 gmf to about 130 gmf, about 80 gmf to about 120 gmf, or about 90 gmf to about 110 gmf.

In yet other aspects of this embodiment, a hydrogel material disclosed herein has a cohesivity of, e.g., about 10 gmf to about 50 gmf, about 25 gmf to about 75 gmf, about 50 gmf to about 150 gmf, about 100 gmf to about 200 gmf, about 100 gmf to about 300 gmf, about 100 gmf to about 400 gmf, about 100 gmf to about 500 gmf, about 200 gmf to about 300 gmf, about 200 gmf to about 400 gmf, about 200 gmf to about 500 gmf, about 200 gmf to about 600 gmf, about 200 gmf to about 700 gmf, about 300 gmf to about 400 gmf, about 300 gmf to about 500 gmf, about 300 gmf to about 600 gmf, about 300 gmf to about 700 gmf, about 300 gmf to about 800 gmf, about 400 gmf to about 500, about 400 gmf to about 600, about 400 gmf to about 700, about 400 gmf to about 800, about 500 gmf to about 600 gmf, about 500 gmf to about 700 gmf, about 500 gmf to about 800 gmf, about 600 gmf to about 700 gmf, about 600 gmf to about 800 gmf, about 700 gmf to about 800 gmf, about 1000 gmf to about 2000 gmf, about 1000 gmf to about 3000 gmf, or about 2000 gmf to about 3000 gmf.

Aspects of the present specification provide, in part, a hydrogel material disclosed herein that exhibits a physiologically-acceptable osmolarity. As used herein, the term "osmolarity" refers to the concentration of osmotically active solutes in solution. As used herein, the term "a physiologically-acceptable osmolarity" refers to an osmolarity in accord with, or characteristic of, the normal functioning of a living organism. As such, administration of a hydrogel material as disclosed herein exhibits an osmolarity that has substantially no long term or permanent detrimental effect when administered to a mammal. Osmolarity is expressed in terms of osmoles of osmotically active solute per liter of solvent (Osmol/L or Osm/L). Osmolarity is distinct from molarity because it measures moles of osmotically active solute particles rather than moles of solute. The distinction arises because some compounds can dissociate in solution, whereas others cannot. The osmolarity of a solution can be calculated from the following expression: Osmol/L=$\Sigma \phi_i \eta_i C_i$, where $\phi$ is the osmotic coefficient, which accounts for the degree of non-ideality of the solution; $\rho$ is the number of particles (e.g. ions) into which a molecule dissociates; and C is the molar concentration of the solute; and i is the index representing the identity of a particular solute. The osmolarity of a hydrogel material disclosed herein can be measured using a conventional method that measures solutions.

In an embodiment, a hydrogel material disclosed herein exhibits a physiologically-acceptable osmolarity. In aspects of this embodiment, a hydrogel material exhibits an osmolarity of, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, or about 500 mOsm/L. In other aspects of this embodiment, a hydrogel material exhibits an osmolarity of, e.g., at least 100 mOsm/L, at least 150 mOsm/L, at least 200 mOsm/L, at least 250 mOsm/L, at least 300 mOsm/L, at least 350 mOsm/L, at least 400 mOsm/L, at least 450 mOsm/L, or at least 500 mOsm/L. In yet other aspects of this embodiment, a hydrogel material exhibits an osmolarity of, e.g., at most 100 mOsm/L, at most 150 mOsm/L, at most 200 mOsm/L, at most 250 mOsm/L, at most 300 mOsm/L, at most 350 mOsm/L, at most 400 mOsm/L, at most 450 mOsm/L, or at most 500 mOsm/L. In still other aspects of this embodiment, a hydrogel material exhibits an osmolarity of, e.g., about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L.

Aspects of the present specification provide, in part, a hydrogel material disclosed herein that exhibits a physiologically-acceptable osmolality. As used herein, the term "osmolality" refers to the concentration of osmotically active solutes per kilo of solvent in the body. As used herein, the term "a physiologically-acceptable osmolality" refers to an osmolality in accord with, or characteristic of, the normal functioning of a living organism. As such, administration of a hydrogel material disclosed herein exhibits an osmolality that has substantially no long term or permanent detrimental effect when administered to a mammal. Osmolality is expressed in terms of osmoles of osmotically active solute per kilogram of solvent (osmol/kg or Osm/kg) and is equal to the sum of the molalities of all the solutes present in that solution. The osmolality of a solution can be measured using an osmometer. The most commonly used instrument in modern laboratories is a freezing point depression osmometer. This instruments measure the change in freezing point that occurs in a solution with increasing osmolality (freezing point depression osmometer) or the change in vapor pressure that occurs in a solution with increasing osmolality (vapor pressure depression osmometer).

In an embodiment, a hydrogel material disclosed herein exhibits a physiologically-acceptable osmolality. In aspects of this embodiment, a hydrogel material exhibits an osmolality of, e.g., about 100 mOsm/kg, about 150 mOsm/kg, about 200 mOsm/kg, about 250 mOsm/kg, about 300 mOsm/kg, about 350 mOsm/kg, about 400 mOsm/kg, about 450 mOsm/kg, or about 500 mOsm/kg. In other aspects of this embodiment, a hydrogel material exhibits an osmolality of, e.g., at least 100 mOsm/kg, at least 150 mOsm/kg, at least 200 mOsm/kg, at least 250 mOsm/kg, at least 300 mOsm/kg, at least 350 mOsm/kg, at least 400 mOsm/kg, at least 450 mOsm/kg, or at least 500 mOsm/kg. In yet other aspects of this embodiment, a hydrogel material exhibits an osmolality of, e.g., at most 100 mOsm/kg, at most 150 mOsm/kg, at most 200 mOsm/kg, at most 250 mOsm/kg, at most 300 mOsm/kg, at most 350 mOsm/kg, at most 400 mOsm/kg, at most 450 mOsm/kg, or at most 500 mOsm/kg. In still other aspects of this embodiment, a hydrogel material exhibits an osmolality of, e.g., about 100 mOsm/kg to about 500 mOsm/kg, about 200 mOsm/kg to about 500 mOsm/kg, about 200 mOsm/kg to about 400 mOsm/kg, about 300 mOsm/kg to about 400 mOsm/kg, about 270 mOsm/kg to about 390 mOsm/kg, about 225 mOsm/kg to about 350 mOsm/kg, about 250 mOsm/kg to about 325 mOsm/kg, about 275 mOsm/kg to about 300 mOsm/kg, or about 285 mOsm/kg to about 290 mOsm/kg.

A hydrogel material disclosed herein is typically resistant to biodegradation upon administration to an individual. As used herein, the term "resistant to biodegradation" is synonymous with "resistant to bioerosion", "resistant to bioresorption", "non-biodegradable", "non-bioerodable" and "non-bioresorbable" and refers to a hydrogel material disclosed herein that is not prone to degrading, eroding, resorbing, decomposing, or breaking down to any substantial or significant degree while implanted in an individual. This resistance to biodegradation enables the hydrogel to retain and maintain the tissue space in order to promote new tissue growth into the space. Non-limiting examples of substantial non-degradation or resistance to biodegradation include less than 10% degradation of a hydrogel material over a time period measured, less than 5% degradation of a hydrogel material over a time period measured, less than 3% degradation of a hydrogel material over a time period measured, less than 1% degradation of a hydrogel material over a time period measured. In an embodiment, a hydrogel material disclosed herein is substantially non-biodegradable or resistant to biodegradation upon administration to an individual.

However, it is anticipated that as the space becomes filled with regenerated tissue which will replace the space being occupied by the hydrogel material. As such, the hydrogel material should be degradable or time. The rate of degradation imparted on the gel will be determined by the speed of replacement with fat and maintenance of volume. In one example, hydrogel material will be resistant to degradation early on with degradation occurring over several months.

In aspects of this embodiment, a hydrogel material is substantially non-biodegradable or resistance to biodegradation for, e.g., about 10 days, about 20 days, about 30 days, about 40 days, about 50 days, about 60 days, about 70 days, about 80 days, or about 90 days, before biodegradation occurs. In other aspects of this embodiment, a hydrogel material is substantially non-biodegradable or resistant to biodegradation for, e.g., at least 10 days, at least 20 days, at least 30 days, at least 40 days, at least 50 days, at least 60 days, at least 70 days, at least 80 days, or at least 90 days, before biodegradation occurs. In yet other aspects of this embodiment, a hydrogel material is substantially non-biodegradable or resistant to biodegradation for, e.g., at most 10 days, at most 20 days, at most 30 days, at most 40 days, at most 50 days, at most 60 days, at most 70 days, at most 80 days, or at most 90 days, before biodegradation occurs. In still other aspects of this embodiment, a hydrogel material is substantially non-biodegradable or resistant to biodegradation for, e.g., about 10 days to about 30 days, about 20 days to about 50 days, about 40 days to about 60 days, about 50 days to about 80 days, or about 60 days to about 90 days, before biodegradation occurs.

In aspects of this embodiment, biodegradation of a hydrogel material disclosed herein occurs with substantially first order release kinetics over a period of, e.g., about 7 days after, about 15 days, about 30 days, about 45 days, about 60 days, about 75 days, or about 90 days after degradation begins. In other aspects of this embodiment, biodegradation of a hydrogel material disclosed herein occurs with substantially first order release kinetics over a period of e.g., at least 7 days, at least 15 days, at least 30 days, at least 45 days, at least 60 days, at least 75 days, or at least 90 days after degradation begins. In yet other aspects of this embodiment, biodegradation of a hydrogel material disclosed herein occurs with substantially first order release kinetics over a period of, e.g., about 10 days to about 30 days, about 20 days to about 50 days, about 40 days to about 60 days, about 50 days to about 80 days, or about 60 days to about 90 days, after degradation begins.

The addition of a compound and hydrogel material to an adipose tissue may be accomplished by any method that ensures sufficient distribution of the compound throughout the adipose tissue so as to promote formation of a blood supply sufficient to support the transplanted tissue. For example, mixing may occur through automated means, such as, e.g., device-controlled agitation or centrifugation, or through manual methods, such as, e.g., luer-locked syringes or vortexing.

The compositions disclosed herein may optionally comprise one or more additional materials useful as a filler for tissue space. Exemplary filler materials suitable with the compositions and methods disclosed herein include, without limitation, fillers comprising a polypeptide such as, e.g., a silk protein, (like silk fibroin), a resilin, a resilin-like polypeptide, an elastin, an elastin-like polypeptide, a silk protein-elastin-like polypeptide, an abductin, a byssus, a gliadin, a glutenin, abductin, keratin, gelatin, or collagen; fillers comprising a polysaccharide such as, e.g., cellulose, agarose, chitosan, or chitin; and fillers comprising a polyester such as, e.g., D-lactic acid, L-lactic acid, racemic lactic acid, glycolic acid, caprolactone. These additional tissue space fillers may be administered as a separate component, or may be complexed with a hydrogel material disclosed herein.

The compositions disclosed herein may optionally comprise one or more immunosuppressive agents that reduce, and preferably prevent, rejection of the transplanted tissue. As used herein, the term "immunosuppressive agent" is synonymous with "immunosuppressive drug" and refers to a compound that inhibits or interferes with normal immune function. Exemplary immunosuppressive agents suitable with the compositions and methods disclosed herein include, without limitation, agents that inhibit T-cell/B-cell costimulation pathways like agents that interfere with the coupling of T-cells and B-cells via the CTLA4 and B7 pathways, including cyclosporine A, myophenylate mofetil, rapamicin, and anti-thymocyte globulin. An immunosuppressive drug is administered in a formulation that is compatible with the route of administration and is administered to an individual at a dosage sufficient to achieve the desired therapeutic effect.

The compositions disclosed herein may further and optionally comprise another agent or combination of agents that provide a beneficial effect when the composition is administered to an individual. Such beneficial agents include, without limitation, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent. Such agents are known in the art and described in, e.g., Gousse, et al., Heat Stable Hyaluronic Acid Compositions For Dermatological Use, U.S. patent application Ser. No. 12/714,337; Gousse, et al., Hydrogel Compositions Comprising Vasoconstricting and Anti-Hemorrhagic Agents for Dermatological Use, each of which is hereby incorporated by reference in its entirety.

In aspects of this embodiment, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In other aspects, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In yet other aspects, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anti-inflammatory agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In other aspects of this embodiment, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent at a concentration of, e.g., about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5.0 mg/mL, about 6.0 mg/mL, about 7.0 mg/mL, about 8.0 mg/mL, about 9.0 mg/mL, or about 10 mg/mL. In yet other aspects of this embodiment, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent at a concentration of, e.g., at least 0.01 mg/mL, at least 0.02 mg/mL, at least 0.03 mg/mL, at least 0.04 mg/mL, at least 0.05 mg/mL, at least 0.06 mg/mL, at least 0.07 mg/mL, at least 0.08 mg/mL, at least 0.09 mg/mL, at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 6.0 mg/mL, at least 7.0 mg/mL, at least 8.0 mg/mL, at least 9.0 mg/mL, or at least 10 mg/mL. In still other aspects of this embodiment, a composition disclosed herein comprises an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent at a concentration of, e.g., at most 0.01 mg/mL, at most 0.02 mg/mL, at most 0.03 mg/mL, at most 0.04 mg/mL, at most 0.05 mg/mL, at most 0.06 mg/mL, at most 0.07 mg/mL, at most 0.08 mg/mL, at most 0.09 mg/mL, at most 0.1 mg/mL, at most 0.2 mg/mL, at most 0.3 mg/mL, at most 0.4 mg/mL, at most 0.5 mg/mL, at most 0.6 mg/mL, at most 0.7 mg/mL, at most 0.8 mg/mL, at most 0.9 mg/mL, at most 1.0 mg/mL, at most 2.0 mg/mL, at most 3.0 mg/mL, at most 4.0 mg/mL, at most 5.0 mg/mL, at most 6.0 mg/mL, at most 7.0 mg/mL, at most 8.0 mg/mL, at most 9.0 mg/mL, or at most 10 mg/mL. In further aspects, a composition disclosed herein comprises an anti-inflammatory agent at a concentration of, e.g., about 0.01 mg/mL to about 0.7 mg/mL, about 0.06 mg/mL to about 0.7 mg/mL, about 0.01 mg/mL to about 1.0 mg/mL, about 0.05 mg/mL to about 1.0 mg/mL, about 0.06 mg/mL to about 1.0 mg/mL, about 0.1 mg/mL to about 1.0 mg/mL, about 0.1 mg/mL to about 2.0 mg/mL, about 0.1 mg/mL to about 3.0 mg/mL, about 0.1 mg/mL to about 4.0 mg/mL, about 0.1 mg/mL to about 5.0 mg/mL, about 0.2 mg/mL to about 0.9 mg/mL, about 0.2 mg/mL to about 1.0 mg/mL, about 0.2 mg/mL to about 2.0 mg/mL, about 0.5 mg/mL to about 1.0 mg/mL, or about 0.5 mg/mL to about 2.0 mg/mL.

In another embodiment, a composition disclosed herein does not comprise an immunosuppressive agent, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, and/or a moisturizing agent.

A compound disclosed herein, or a composition comprising such a compound is generally administered to an individual as a pharmaceutical composition. Pharmaceutical compositions may be prepared by combining a therapeutically effective amount of at least one compound according to the present specification, or a pharmaceutically acceptable acid addition salt thereof, as an active ingredient, with conventional acceptable pharmaceutical excipients, and by preparation of unit dosage forms suitable for topical ocular use. The therapeutically efficient amount typically is between about 0.0001% (w/v) and about 5% (w/v), preferably about 0.001% (w/v) to about 1.0% (w/v) in liquid formulations. As used herein, the term "pharmaceutical composition" refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

The compounds disclosed herein may also be incorporated into a drug delivery platform in order to achieve a controlled compound release profile over time. Such a drug delivery platform comprises a compound disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as, e.g., random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers for use in a drug delivery platform include, without limitation, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in, e.g., Drost, et. al., Controlled Release Formulation, U.S. Pat. No. 4,756,911; Smith, et. al., Sustained Release Drug Delivery Devices, U.S. Pat. No. 5,378,475; Wong and Kochinke, Formulation for Controlled Release of Drugs by Combining Hyrophilic and Hydrophobic Agents, U.S. Pat. No. 7,048,946; Hughes, et. Al., Compositions and Methods for Localized Therapy of the Eye, U.S. Patent Publication 2005/0181017; Hughes, Hypotensive Lipid-Containing Biodegradable Intraocular Implants and Related Methods, U.S. Patent Publication 2005/0244464; Altman, et al., Silk Fibroin Hydrogels and Uses Thereof, U.S. patent application Ser. No. 12/764,039, filed on Apr. 20, 2010; each of which is incorporated by reference in its entirety.

In aspects of this embodiment, a polymer composing the matrix is a polypeptide such as, e.g., silk fibroin, keratin, or collagen. In other aspects of this embodiment, a polymer composing the matrix is a polysaccharide such as, e.g., cellulose, agarose, elastin, chitosan, chitin, or a glycosaminoglycan like chondroitin sulfate, dermatan sulfate, keratan sulfate, or hyaluronic acid (as discussed supra). In yet other aspects of this embodiment, a polymer composing the matrix is a polyester such as, e.g., D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with a drug, desired release kinetics of a drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform includes both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform releases a compound disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a compound disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of, e.g., at most 1 day after administration, at most 2 days after administration, at most 3 days after administration, at most 4 days after administration, at most 5 days after administration, or at most 6 days after administration.

A pharmaceutical composition disclosed herein can optionally include a pharmaceutically acceptable carrier that facilitates processing of an active compound into pharmaceutically acceptable compositions. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

Aspects of the present specification provide, in part, a method of treating a soft tissue condition of an individual by administering a composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a compound disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A composition or compound is administered to an individual. An individual is typically a human being. Typically, any individual who is a candidate for a conventional soft tissue replacement procedure is a candidate for a soft tissue replacement procedure disclosed herein. In addition, the presently disclosed compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, Parry-Romberg syndrome, lupus erythematosus profundus, dermal divots, sunken cheeks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

The amount of adipose tissue and/or hydrogel material used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of adipose tissue and/or hydrogel material administration may be manifested by one or more of the following clinical and/or cosmetic measures: altered and/or improved soft tissue shape, altered and/or improved soft tissue size, altered and/or improved soft tissue contour, altered and/or improved tissue function, improved transplant tissue survival, improved patient satisfaction and/or quality of life, and decreased use of implantable foreign material.

For example, for breast augmentation procedures, effectiveness of adipose tissue and/or hydrogel material administration may be manifested by one or more of the following clinical and/or cosmetic measures: increased breast size, altered breast shape, altered breast contour, sustained engraftment, decreased rate of liponecrotic cyst formation, improved patient satisfaction and/or quality of life, and decreased use of breast implant.

As another example, effectiveness of adipose tissue and/or hydrogel material administration in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of adipose tissue and/or hydrogel material administration for sphincter support may be manifested by one or more of the following clinical measures: decreased frequency of incontinence, sustained engraftment, improved patient satisfaction and/or quality of life, and decreased use of implantable foreign filler.

The amount of a compound used with any of the methods disclosed herein will typically be a therapeutically effective amount. As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As a non-limiting example, an effective amount is an amount sufficient to promote formation of a blood supply sufficient to support the transplanted tissue.

As another non-limiting example, an effective amount is an amount sufficient to promote formation of new blood vessels and associated vasculature (angiogenesis) and/or an amount sufficient to promote repair or remodeling of existing blood vessels and associated vasculature. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

In aspects of this embodiment, the amount of a compound added is, e.g., 0.01 mg, 0.05 mg, 0.1 mg, 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 500 mg, 750 mg, or 1000 mg. In other aspects of this embodiment, the amount of a compound added is, e.g., 0.01 mg/mL, 0.05 mg/mL, 0.1 mg/mL, 0.5 mg/mL, 1 mg/mL, 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 500 mg/mL, 750 mg/mL, or 1000 mg/mL. In yet other aspects of this embodiment, the amount of a compound added is, e.g., 0.01 mg/10 mL of tissue, 0.05 mg/10 mL of tissue, 0.1 mg/10 mL of tissue, 0.5 mg/10 mL of tissue, 1 mg/10 mL of tissue, 5 mg/10 mL of tissue, 10 mg/10 mL of tissue, 20 mg/10 mL of tissue, 30 mg/10 mL of tissue, 40 mg/10 mL of tissue, 50 mg/10 mL of tissue, 60 mg/10 mL of tissue, 70 mg/10 mL of tissue, 80 mg/10 mL of tissue, 90 mg/10 mL of tissue, 100 mg/10 mL of tissue, 150 mg/10 mL of tissue, 200 mg/10 mL of tissue, 250 mg/10 mL of tissue, 500 mg/10 mL of tissue, 750 mg/10 mL of tissue, or 1000 mg/10 mL of tissue.

In aspects of this embodiment, the amount of a compound added is, e.g., about 0.01 mg to about 0.1 mg, about 0.1 mg to about 1 mg, about 1 mg to about 10 mg, about 10 mg to about 100 mg, or about 100 mg to about 1000 mg. In other aspects of this embodiment, the amount of a compound added is, e.g., about 0.01 mg/mL to about 0.1 mg/mL, about 0.1 mg/mL to about 1 mg/mL, about 1 mg/mL to about 10 mg/mL, about 10 mg/mL to about 100 mg/mL, or about 100 mg/mL to about 1000 mg/mL. In yet other aspects of this embodiment, the amount of a compound added is, e.g., about 0.01 mg/10 mL of tissue to about 0.1 mg/10 mL of tissue, about 0.1 mg/10 mL of tissue to about 1 mg/10 mL of tissue, about 1 mg/10 mL of tissue to about 10 mg/10 mL of tissue, about 10 mg/10 mL of tissue to about 100 mg/10 mL of tissue, or about 100 mg/10 mL of tissue to about 1000 mg/10 mL of tissue.

In aspects of this embodiment, the amount of a compound added is, e.g., about 0.0001% (w/v) to about 5% (w/v), about 0.001% (w/v) to about 5% (w/v), about 0.01% (w/v) to about 5% (w/v), about 0.1% (w/v) to about 5% (w/v), or about 1% (w/v) to about 5% (w/v). In other aspects of this embodiment, the amount of a compound added is, e.g., about 0.001% (w/v) to about 1.0% (w/v), about 0.01% (w/v) to about 1.0% (w/v), or about 0.1% (w/v) to about 1.0% (w/v).

A composition disclosed herein can be mixed with the harvested adipose tissue and, as such, be administered simultaneously with the adipose tissue. Additionally, or alternatively, a composition disclosed herein can be administered after administration of the adipose tissue. In aspects of this embodiment, a composition disclosed herein is administered to the individual additionally, or alternatively, e.g., about 1 day after adipose tissue implantation, about 2 days after adipose tissue implantation, about 3 days after adipose tissue implantation, or about 4 days after adipose tissue implantation. In other aspects, a composition disclosed herein is administered to the individual additionally, or alternatively, e.g., about once a day for about 3 to about 10 consecutive days, about once a day for about 7 to about 14 consecutive days, about once a day for about 10 to about 21 consecutive days, or about once a day for about 14 to about 28 consecutive days. In other aspects, the daily dose can be, e.g., twice a day, three times a day, or four times a day.

The route of administration of composition administered to an individual patient will typically be determined based on the cosmetic and/or clinical effect desired by the individual and/or physician and the body part or region being treated. Compositions or adipose tissue may be administered by any means known to persons of ordinary skill in the art including, without limitation, syringe with needle, catheter, or by direct surgical implantation. In addition, the disclosed composition or adipose tissue can be administered once, or over a plurality of times. Ultimately, the timing used will follow quality care standards.

For a breast soft tissue replacement procedure, the route of administration may include axillary, periareolar, and/or inframammary routes. For a facial soft tissue replacement procedure, the route of administration can be frontal, temporal, zygomatic, periocular, amdibula, perioral or chin routes. In urinary incontinence procedures, the route of administration may include transurethral or periurethral routes. Alternatively or in addition, the transplant may be delivered via an antegrade route. The routes discussed herein do not exclude the use of multiple routes to achieve the desired clinical effect, or umbilical incision. Alternatively or in addition, cell-enhanced tissue may be delivered through a transaxillary endoscopic subpectoral approach.

A composition or compound administered to an individual to treat a soft tissue condition promotes formation of a blood supply sufficient to support the transplanted tissue. Blood supply formation includes, without limitation, formation of new blood vessels and associated vasculature (angiogenesis) and repair or remodel of existing blood vessels and associated vasculature.

Aspects of the present specification disclose, in part, a method of treating a soft tissue condition of an individual, the method comprising the steps of a) administering the adipose tissue to a site of the soft tissue condition; and b) administering a composition comprising a compound as disclosed herein to the site of the soft tissue condition. The adipose tissue and compound(s) administered include the adipose tissue disclosed herein. In these methods, the adipose tissue is administered separately from a composition comprising the compound. Thus, in one aspect of this embodiment, adipose tissue is administered first, followed by administration of a composition comprising the compound. In another aspect of this embodiment, a composition comprising a compound is administered first, followed by administration of adipose tissue. In certain embodiments, the composition comprising a compound further comprises an HA. In other embodiments, a second composition comprising HA is administered at the same time, before, or after the administration of the first composition that comprises one or more of the compounds disclosed herein.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compositions and methods of soft tissue replacement disclosed herein.

Example 1

Synthesis of Compounds of Formula I

This example illustrates the synthesis scheme for the compounds of formula I.

The methods of preparing the compounds disclosed herein are further illustrated by the following non-limiting examples, which are summarized in the reaction schemes of FIGS. 1-9 wherein the compounds are identified by the same designator in both the Examples and the Figures.

2-Alkyl-cyclopentane-1,3-dione (1a, FIG. 1). A mixture of 1,3-cyclopentanedione (89.4 mmol, Aldrich), I-$R^2$ (96.4 mmol, Aldrich), and KOH (5.097 g, 90.8 mmol) in water (25 mL)/dioxane (75 mL) was heated at reflux. After 5 hours, a solution of KOH (2 g) and I-$R^2$ (2 mmol) in water (5 mL)/dioxane (15 mL) was added and after another 3 hours at reflux, the solution was stirred at room temperature overnight. A solution of KOH (2 g) and I-$R^2$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until boiling was observed (ca. 15 minutes). The mixture was cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2-Alkyl-2-methyl-cyclopentane-1,3-dione (2a, FIG. 1). A mixture of 2-methyl-1,3-cyclopentanedione (10.025 g, 89.4 mmol, Aldrich), I-$R^2$ (96.4 mmol, Aldrich), and KOH (5.097 g, 90.8 mmol) in water (25 mL)/dioxane (75 mL) was heated at reflux. After 5 hours, a solution of KOH (2 g) and I-$R^2$ (2 mmol) in water (5 mL)/dioxane (15 mL) was added and after another 3 hours at reflux, the solution was stirred overnight at room temperature. A solution of KOH (2 g) and I-$R^2$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2,2-Dialkyl-methyl-cyclopentane-1,3-dione (2b, FIG. 1). A mixture of 2-alkyl-1,3-cyclopentanedione 1a (89.4 mmol, Aldrich), I-$R^3$ (96.4 mmol, Aldrich), and KOH (5.097 g, 90.8 mmol) in water (25 mL)/dioxane (75 mL) was heated at reflux. After 5 hours, a solution of KOH (2 g) and I-$R^3$ (2 mmol) in water (5 mL)/dioxane (15 mL) was added and after another 3 hours at reflux, the solution was stirred at room temperature overnight. A solution of KOH (2 g) and I-$R^3$ (2.4 mmol) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was then cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

Spiro[2.4]heptane-4,7-dione (2c, FIG. 1). A mixture of 2-alkyl-1,3-cyclopentanedione 1a (89.4 mmol, Aldrich), 1,2-dibromoethane (120 mmol, Aldrich), and KOH (5.097 g, 90.8 mmol) in water (25 mL)/dioxane (75 mL) was heated at reflux for 24 hours. The mixture was cooled, and the product extracted with ether (1×100 mL, 3×75 mL). The combined ether extracts were evaporated, the residue combined with 10% HCl (50 mL), and the resulting mixture placed in a 120° C. oil bath until boiling was observed (ca. 15 minutes). The mixture was then cooled to room temperature, neutralized by addition of NaHCO$_3$ solution (150 mL, saturated) and the resulting mixture extracted with CH$_2$Cl$_2$ (4×75 mL). The combined CH$_2$Cl$_2$ solution was dried (MgSO$_4$), filtered and evaporated to leave a brown oil which was used directly in the next step.

2,2-Dimethyl-cyclopentane-1,3-dione (2, FIG. 1). Synthesized according to Agosta and Smith, *J. Org. Chem.*, 35: 3856 (1970). A mixture of 2-methyl-1,3-cyclopentanedione (10.025 g, 89.4 mmol, Aldrich), methyl iodide (6.0 mL, 96.4 mmol, Aldrich), and KOH (5.097 g, 90.8 mmol) in water (25 mL)/dioxane (75 mL) was heated at reflux. After 5 hours, a solution of KOH (2 g) and MeI (2.4 mL) in water (5 mL)/dioxane (15 mL) was added and after another 3 hours at reflux, the solution was stirred at room temperature overnight. A solution of KOH (2 g) and MeI (2.4 mL) in water (5 mL)/dioxane (15 mL) was added to the overnight reaction and heating at reflux. After 4 hours, the mixture was cooled to room temperature and extracted with ether (1×100 mL, 3×75 mL). The combined ether extracts were evaporated, the residue combined with 10% HCl (50 mL), and the resulting mixture placed in a 120° C. oil bath until it began boiling (ca. 15 minutes). The mixture was cooled to room temperature, neutralized by addition of saturated NaHCO$_3$ solution (150 mL) and the resulting mixture extracted with CH$_2$Cl$_2$ (4×75 mL). The combined CH$_2$Cl$_2$ solution was dried (MgSO$_4$), filtered and evaporated to leave a brown oil (10.474 g, 83 mmol, 93%) which was used directly in the next step.

Figure 2:
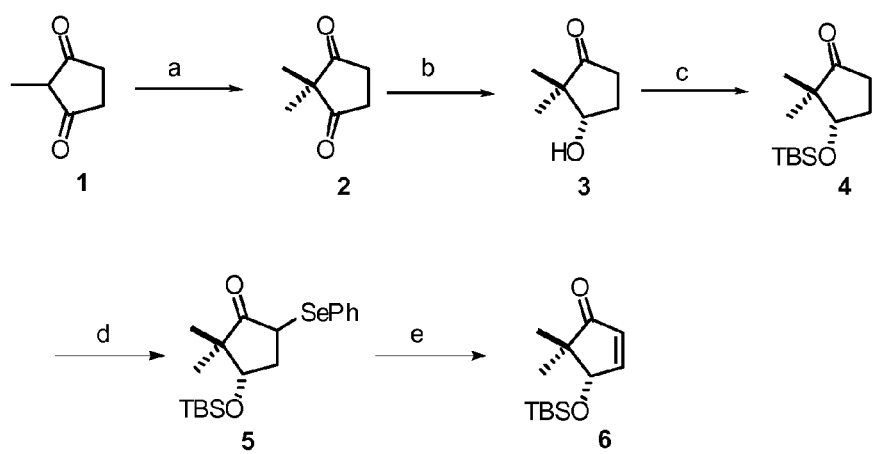

(S)-3-Hydroxy-2,2-dimethyl-cyclopentanone (3, FIG. 2). Synthesized according to Brooks, et al., *J. Org. Chem.*, 52: 3223 (1987). A 35° C. (internal temperature) solution of D-glucose (106.73 g, 592 mmol, Aldrich) in water (690 mL) in a 4 L Erlenmeyer was treated with baker's yeast (71.065 g, Fleischmann's). The mixture was fermented for 2 hours, and 2,2-dimethyl-cyclopentane-1,3-dione (2) (7.316 g, 58 mmol) was added. The mixture was stirred for 48 hours and filtered through celite, washing with about 1 L CH$_2$Cl$_2$. About 100 mL of brine was added to the filtrate and the layers separated using a separatory funnel. Brine (400 mL) was added to the aqueous layer and the resulting solution extracted further with CH$_2$Cl$_2$ (3×500 mL). The combined CH$_2$Cl$_2$ solution was dried (MgSO$_4$), filtered and evaporated to leave a yellow oil. Flash chromatography (11×5 cm, 20% EtOAc/hexs→25%→30%→40%→50%) gave alcohol 3 (2.435 g, 19 mmol, 33%).

The enantiomeric excess of 3 was assayed by $^1$H NMR of the corresponding Mosher's ester which was prepared by treatment of alcohol 3 (11 mg, 0.09 mmol) in dichloroethane (0.3 mL, Aldrich) with pyridine (27 µL, 0.33 mmol, Aldrich) and (R)-α-methoxy-α-trifluoromethyphenylacetic acid chloride (58 µL, 0.31 mmol, Fluka). The mixture was stirred overnight and then partitioned between water (10 mL) and ether (10 mL). The ether layer was washed with 1 M HCl (10 mL) and saturated NaHCO$_3$ solution and then dried (MgSO$_4$), filtered and evaporated. $^1$H NMR analysis was done on the crude ester.

(S)-3-(tert)-Butyl-dimethyl-silanyloxy-2,2-dimethyl-cyclopentanone (4, FIG. 2). A solution of alcohol (3) (520 mg, 4.1 mmol) and 2,6-lutidine (0.56 mL, 4.8 mmol, Aldrich) in CH$_2$Cl$_2$ (8.0 mL, Aldrich) was treated with TBSOTf (1.0 mL, 4.3 mmol, Aldrich). After 5.5 hours, saturated NaHCO$_3$ solution (20 mL) was added and the mixture extracted with CH$_2$Cl$_2$ (20 mL). The CH$_2$Cl$_2$ solution was washed with 20 mL each of 1 M HCl, saturated NaHCO$_3$ solution, and brine and then dried (MgSO$_4$), filtered and evaporated. Flash chromatography (5×5 cm, 10% Et$_2$O/pentane) gave TBS ether (4) (698 mg, 2.9 mmol, 70%).

(S)-3-(tert)-Butyl-dimethyl-silanyloxy-2,2-dimethyl-5-phenylselanyl-cyclopentanone (5, FIG. 2). A solution of TBS ether (4) (1.496 g, 6.2 mmol) in THF (2 mL, Aldrich) was added dropwise to a −78° C. solution of LDA (4.9 mL, 7.3 mmol, 1.5 M/cyclohexane, Aldrich) in THF (22 mL, Aldrich), rinsing with 2 mL THF. After 15 minutes, a solution of PhSeCl (1.424 g, 7.4 mmol, Aldrich) in THF (2 mL) was quickly added by cannula, rinsing with 2 mL THF. The solution was stirred for 10 minutes and then partitioned between 50 mL 0.5 M HCl and 75 mL ether. The ether layer was washed with 30 mL each of water, saturated NaHCO$_3$ solution, and brine and then dried (MgSO$_4$), filtered and evaporated. Flash chromatography (2% EtOAc/hexs→4%) gave phenylselenide (5) (1.641 g, 4.1 mmol, 67%) along with 476 mg of mixed fractions containing a lower R$_f$ impurity.

(S)-4-(tert)-Butyl-dimethyl-silanyloxy-5,5-dimethyl-cyclopent-2-enone (6, FIG. 2). A solution of selenide (5) (1.641 g, 4.1 mmol) and pyridine (0.62 mL, 7.7 mmol, Aldrich) in CH$_2$Cl$_2$ (13 mL, Aldrich) was treated with water (1 mL) and 30% H$_2$O$_2$ (1.1 mL, Aldrich). The mixture was stirred for 30 minutes and then partitioned between 25 mL CH$_2$Cl$_2$ and 25 mL saturated NaHCO$_3$ solution. The aqueous layer was extracted with 25 mL CH$_2$Cl$_2$ and the combined CH$_2$Cl$_2$ solution washed with 1 M HCl (2×25 mL) and brine (50 mL). The solution was dried (MgSO$_4$), filtered and evaporated to leave an orange oil. Flash chromatography (6×4 cm, 10% ether/pentane) gave enone (6) (572 mg, 2.4 mmol, 59%).

Figure 3:
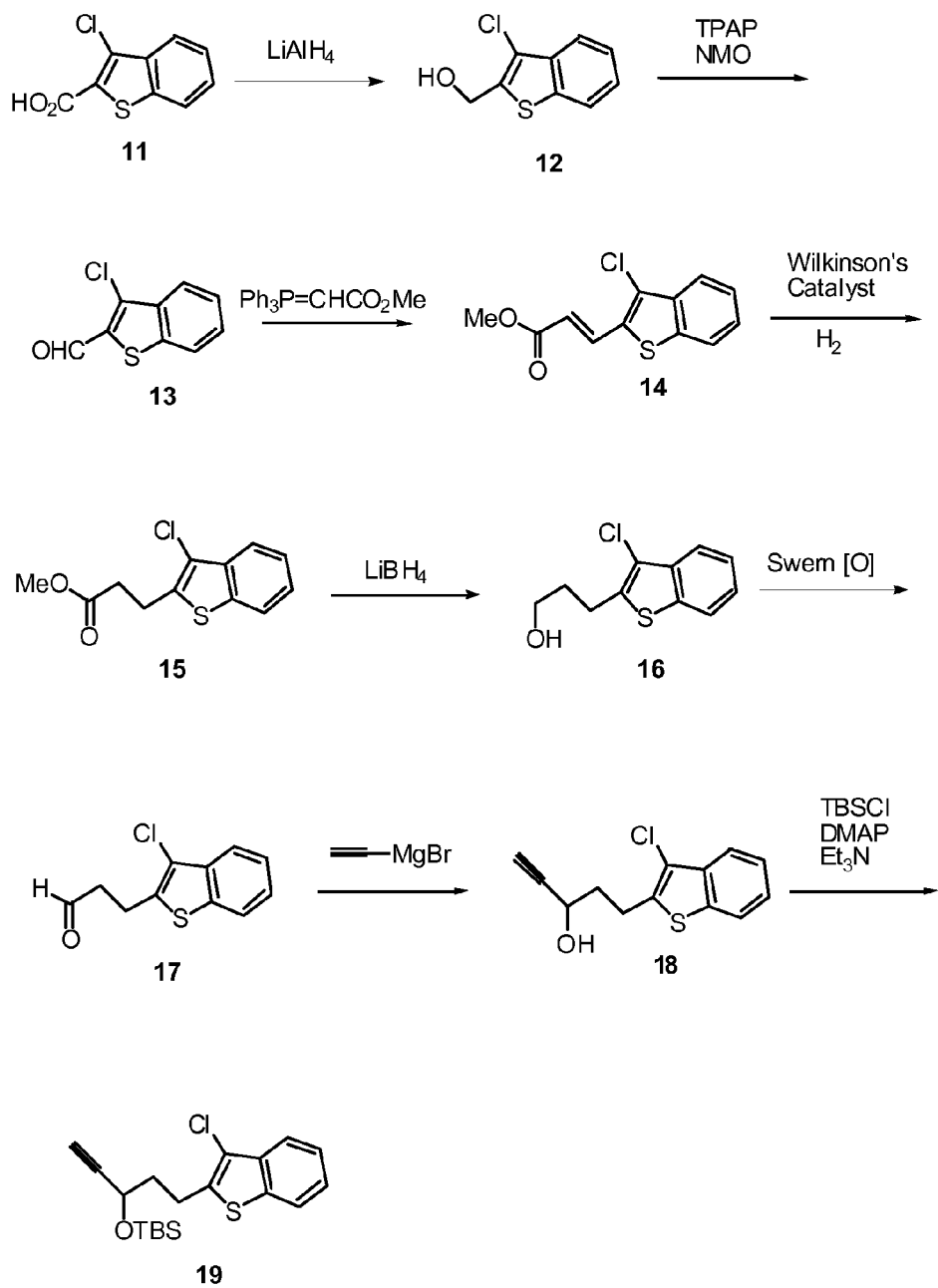

(3-Chloro-benzo[b]thiophen-2-yl)-methanol (12, FIG. 3). To an ice cold solution of 10.0 g (47.0 mmol) of 3-chloro-benzo[b]thiophene-2-carboxylic acid (11) in 200 mL of THF was added 47 mL of LiAlH$_4$ (47 mmol, 1 M/THF). After 3 hours, the reaction was quenched by adding methanol (ca. 40 mL). The volatiles were evaporated and the residue treated with 50 mL 1 M HCl. After stirring for 10 minutes, the mixture was extracted with CH$_2$Cl$_2$ (3×150 mL). The combined CH$_2$Cl$_2$ solution was dried (MgSO$_4$), filtered and evaporated. Purification by flash chromatography on silica gel (10-20% ethyl acetate/hexane) gave 4.32 g (21.6 mmol, 46%) of the alcohol (12).

3-Chloro-benzo[b]thiophene-2-carbaldehyde (13, FIG. 3). A solution of alcohol 12 (4.32 g, 21.6 mmol) in 40 mL of CH$_2$Cl$_2$ was treated with 4 A molecular sieves, NMO (3.81 g, 32.5 mmol), and TPAP (381 mg, 1.08 mmol). The reaction was stirred for 10 minutes and then dried by evaporated. Purification by flash chromatography on silica gel (2% ethyl acetate/hexane) gave 3.52 g (18.3 mmol, 84%) of the aldehyde (13).

(E)-3-(3-Chloro-benzo[b]thiophen-2-yl)-acrylic acid methyl ester (14, FIG. 3). A solution of 3.52 g (18.3 mmol) of (13) in 50 mL toluene was treated with methyl(triphenylphosphoranylidene)acetate (7.48 g, 21.9 mmol). After 4 hours, saturated NaHCO$_3$ solution (50 mL) was added and the mixture extracted with ethyl acetate (2×75 mL). The combined ethyl acetate solution was washed with brine (50 mL), dried (Na$_2$SO$_4$), filtered and evaporated. Purification by flash chromatography on silica gel (5% ethyl acetate/hexane) provided 3.60 g (14.6 mmol, 80%) of the enoate (14).

3-(3-Chloro-benzo[b]thiophen-2-yl)-propionic acid methyl ester (15, FIG. 3). A solution of 3.60 g (14.6 mmol) of (14) in 50 mL THF was treated with Wilkinson's catalyst (3.35 g, 3.62 mmol). The mixture was stirred under 1 atm H$_2$ for 18 hours and then was filtered through celite. The solvent was evaporated and the residue purified by flash chromatography on silica gel (0-2% ethyl acetate/hexane) to give 3.63 g (14.3 mmol, 99%) of the saturated ester (15).

3-(3-Chloro-benzo[b]thiophen-2-yl)-propan-1-ol (16, FIG. 3). An ice cold solution of 3.63 g (14.3 mmol) of (15) in 60 mL of ether was treated with LiBH$_4$ (621 mg, 28.5 mmol) and methanol (2 mL). After 30 minutes, 30 mL of 0.5 M NaOH solution was added. The mixture was extracted with ethyl acetate (2×25 mL) and the combined ethyl acetate solution was washed with brine (50 mL), dried (MgSO$_4$), filtered and evaporated. The residue was purified by flash chromatography on silica gel (5-20% ethyl acetate/hexane) to give 2.57 g (11.3 mmol, 79%) of the alcohol (16).

3-(3-Chloro-benzo[b]thiophen-2-yl)-propionaldehyde (17, FIG. 3). A −78° C. solution of oxalyl chloride (1.73 g, 13.6 mmol) in dichloromethane (20 mL) was treated with DMSO (20 mL). After 5 minutes, a solution of alcohol (16) (2.57 g, 11.3 mmol) in dichloromethane (20 mL) was added. After another 15 minutes, triethylamine (7.1 mL, 50.6 mmol) was added. The reaction was stirred at −78° C. for 5 minutes, and warmed to room temperature. After 30 minutes, 100 mL water was added and the mixture extracted with dichloromethane (3×60 mL). The combined dichloromethane solution was dried (Na$_2$SO$_4$), filtered and evaporated. Purification by flash chromatography on silica gel (10% ethyl acetate/hexane) gave 2.11 g (9.4 mmol, 83%) of the aldehyde (17).

Figure 4:
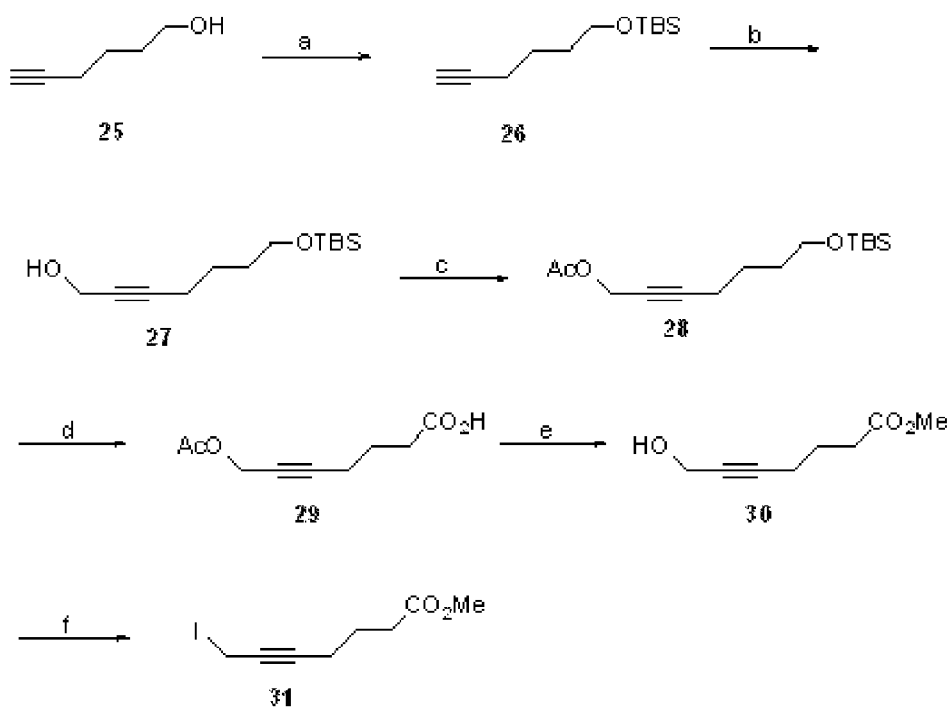

5-(3-Chloro-benzo[b]thiophen-2-yl)-pent-1-yn-3-ol (18, FIG. 3). A solution of aldehyde (17) (2.11 g, 9.4 mmol) in 15 mL THF was added to a solution of ethynylmagnesium bromide (28.2 mL, 14.1 mmol, 0.5 M THF) at 0° C. After 1.5 hours, saturated NH$_4$Cl solution (75 mL) was added and the mixture was extracted with ethyl acetate (3×50 mL). The combined ethyl acetate solution was washed with brine (50 mL) and then dried (Na$_2$SO$_4$), filtered and evaporated. Purification by flash chromatography (5-20% ethyl acetate/hexane) gave 2.20 g (8.78 mmol, 93%) of the alcohol (18).

tert-Butyl-{1-[2-(3-chloro-benzo[b]thiophen-2-yl)-ethyl]-prop-2-ynyloxy}-dimethyl-silane (19, FIG. 3). A solution of alcohol (18) (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 hours and then saturated sodium bicarbonate solution (50 mL) was added. The mixture was extracted with dichloromethane (2×50 mL) and the combined dichloromethane solution dried (Na$_2$SO$_4$), filtered and evaporated. Purification by flash chromatography (4% ethyl acetate/hexane) gave 3.06 g (6.4 mmol, 73%) of the protected alcohol (19).

tert-Butyl-hex-5-ynyloxy-dimethyl-silane (26); 7-(tert-Butyl-dimethyl-silanyloxy)-hept-2-yn-1-ol (27); and Acetic acid 7-(tert-butyl-dimethyl-silanyloxy)-hept-2-ynyl ester (28, FIG. 4). A solution of 7-(tert-Butyl-dimethyl-silanyloxy)-hept-2-yn-1-ol (27) (4.507 g, 21 mmol) in pyridine (20 mL) was treated with acetic anhydride (3.0 mL, 31.8 mmol). After 18 hours, the solvent was evaporated and the residue co-evaporated with toluene. The residue was used directly in the next step.

7-Acetoxy-hept-5-ynoic acid (29, FIG. 4). A solution of crude (28) in acetone (100 mL) was treated with Jones Reagent (18.0 mL, 41.4 mmol, 2.3 M) and cooled with an ice bath. After 1 hour at room temperature, 10 mL isopropyl alcohol was added and the mixture stirred for 15 minutes. The mixture still had a brown color so another 10 mL isopropyl alcohol was added. After another 15 minutes, the color had not changed so the mixture was filtered through celite and the filtrate evaporated in vacuo. The residue was partitioned between 100 mL ether and 100 mL saturated ammonium chloride solution. The aqueous layer was extracted with 100 mL ether and the combined ether solution washed with brine and then dried (MgSO$_4$), filtered and evaporated to leave a yellow oil (6.333 g) that was used directly in the next step.

7-Hydroxy-hept-5-ynoic acid methyl ester (30, FIG. 4). The crude acid (29) (6.333 g) was treated with a 1% solution of acetyl chloride in methanol (60 mL). After 16 hours, sodium bicarbonate (1.966 g, 23.4 mmol) was added. The mixture was dried (MgSO$_4$), filtered through celite and evaporated in vacuo. Purification by flash chromatography on silica gel (30-40% ethyl acetate/hexanes) gave 7-Hydroxy-hept-5-ynoic acid methyl ester (30) (3.022 g, 19.3 mmol, 92% from 7-(tert-Butyl-dimethyl-silanyloxy)-hept-2-yn-1-ol (27).

Figure 5:
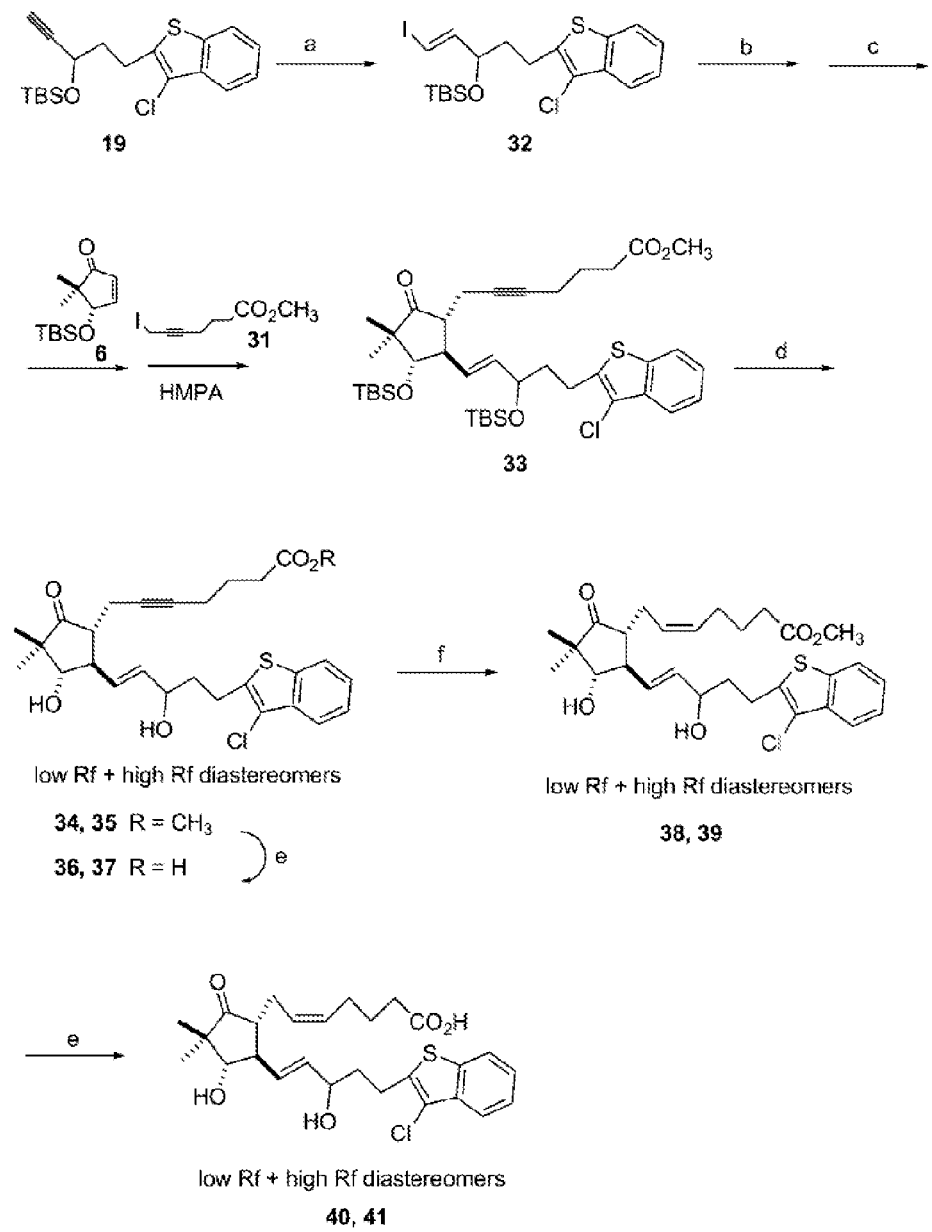

7-Iodo-hept-5-ynoic acid methyl ester (31, FIG. 4). A solution of (30) (1.347 g, 8.6 mmol) in 5 mL dichloromethane was added to a mixture of triphenylphosphine (2.725 g, 10.4 mmol), imidazole (726 mg, 10.7 mmol), and iodine (2.602 g, 10.3 mmol) in 34 mL dichloromethane, rinsing with 5 mL dichloromethane. After 40 minutes, the dichloromethane was evaporated in vacuo to about 2 mL and the resulting mixture filtered through basic alumina, washing with 10% ethyl acetate/hexanes. Purification by flash chromatography on silica gel (10% ethyl acetate/hexanes) gave 1.878 g (7.1 mmol, 83%) of the propargyl iodide.

tert-Butyl-{(E)-1-[2-(3-chloro-benzo[b]thiophen-2-yl)-ethyl]-3-iodo-allyloxy}-dimethyl-silane (32, FIG. 5). A solution of alkyne (19) (5.547 g, 15.2 mmol) in dichloromethane (50 mL) was treated with Cp$_2$ZrHCl (5.794 g, 22.5 mmol). The reaction was stirred for 45 minutes and then N-iodosuccinimide (4.966 g, 22.1 mmol) was added. After 15 minutes, saturated sodium bicarbonate solution (200 mL) was added and the mixture extracted with dichloromethane (2×100 mL). The combined dichloromethane solution was dried (MgSO$_4$), filtered and evaporated. Purification by flash chromatography on silica gel (0-5% ethyl acetate/hexanes) gave 6.608 g (13.1 mmol, 86%) of the vinyl iodide (32).

7-{(1R,4S,5R)-4-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]-3,3-dimethyl-2-oxo-cyclopentyl}-hept-5-ynoic acid methyl ester (33, FIG. 5). A −78° C. solution of iodide (32) (675 mg, 1.34 mmol) in THF (2.0 mL) was treated with tert-butyllithium (1.73 mL, 2.94 mL, 1.7 M/pentane). The dark red mixture was stirred for 25 minutes and then dimethylzinc (0.80 mL, 1.6 mmol, 2 M/toluene) was added. The solution was stirred at 0° C. for 15 minutes and then recooled to −78° C. A solution of enone (6) (208 mg, 0.87 mmol) in THF (1.0 mL) was added over 2 hours by syringe pump, rinsing with 0.5 mL THF. After 30 minutes, HMPA (1.34 mL, distilled from CaH$_2$) was added followed by a solution of propargyl iodide (31) (1.286 g, 4.83 mmol) in THF (1.0 mL). The solution was stirred in a −40° C. bath overnight and then 20 mL saturated ammonium chloride solution and 10 mL water were added. The mixture was extracted with dichloromethane (20 mL) and ethyl acetate (2×20 mL). The combined organic extracts were dried (MgSO$_4$), filtered and evaporated. Purification by flash chromatography on silica gel (5-10% ethyl acetate/hexanes) gave 198 mg (0.27 mmol, 31%) of (33).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-ynoic acid methyl ester (34, 35, FIG. 5). A solution of (33) (198 mg, 0.27 mmol) in CH$_3$CN (6.5 mL) was treated with HF-pyridine (1.2 mL). The solution was stirred for 3 hours and saturated sodium bicarbonate solution (120 mL) was added. The mixture was extracted with dichloromethane (3×50 mL) and the combined dichloromethane solution dried (Na$_2$SO$_4$), filtered and evaporated. Purification by flash chromatography (50% ethyl acetate/hexane) followed by preparative TLC (55% ethyl acetate/hexane) gave 55 mg (0.11 mmol, 41%) of the less polar diastereomer (34) and 51 mg (0.10 mmol, 37%) of the more polar diastereomer (35).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-ynoic acid (low R$_f$ diastereomer, 36, FIG. 5). A solution of (34) (9 mg, 0.017 mmol) and rabbit liver esterase (1 mg) in pH 7.2 phosphate buffer (2 mL)/CH$_3$CN (0.1 mL) was stirred for 17 hours. The mixture was then coevaporated with CH$_3$CN to remove water and the residue purified by flash chromatography on silica gel (3-7% MeOH/CH$_2$Cl$_2$) to give 8 mg (0.016 mmol, 93%) of the acid (36).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-ynoic acid (high R$_f$ diastereomer, 37, FIG. 5). A solution of (35) (12 mg, 0.023 mmol) and rabbit liver esterase (1 mg) in pH 7.2 phosphate buffer (2 mL)/CH$_3$CN (0.1 mL) was stirred for 17 hours. TLC showed the presence of starting material, so another 2 mg of the esterase was added. After stirring for another 24 hours, the reaction was complete. Work up and purification as above for (36) gave 8 mg (0.016 mmol, 69%) of the acid (37).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-enoic acid methyl ester (low R$_f$ diastereomer, 38, FIG. 5). Ethanol (95%, 2.5 mL) was added to NiCl$_2$ (50 mg, 0.39 mmol) and NaBH$_4$ (7 mg, 0.19 mmol). The resulting black mixture was stirred for 5 minutes and then ethylenediamine (41 μL, 0.61 mmol) was added. After 15 minutes, a solution of alkyne (34) (40 mg, 0.077 mmol) in 0.5 mL 95% ethanol was added, rinsing with 0.5 mL ethanol. The flask was purged with H$_2$ and allowed to stir under 1 atm H$_2$ for 22 hours. The mixture was then filtered through celite and purified by flash chromatography on silica gel (55% ethyl acetate/hexanes) to give 17 mg (0.032 mmol, 43%) of the alkene (38).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-enoic acid methyl ester (high R$_f$ diastereomer 39, FIG. 5). The same procedure as for (36) was followed to give 17 mg (0.032 mmol, 41%) of (39).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-enoic acid (low R$_f$ diastereomer, 40, FIG. 5). The same procedure as above for (36) was used to give 9 mg (0.018 mmol, 85%) of acid (40). 300 MHz $^1$H NMR (CDCl$_3$, ppm) δ 7.73 (2H, d, J=8.4 Hz) 7.45-7.30 (2H, m) 5.8-5.6 (2H, m) 5.4-5.3 (2H, m) 4.3-4.1 (1H, m) 3.57 (1H, d, J=9.7 Hz) 3.1-2.9 (2H, m) 2.5-1.9 (10H, m) 1.7-1.6 (2H, m) 1.09 (3H, s) 0.89 (3H, s).

(Z)-7-{(1R,4S,5R)-5-[(E)-5-(3-chloro-benzo[b] thiophene-2-yl)-3-hydroxy-pent-1-enyl]-4-hydroxy-3,3-dimethyl-2-oxo-cyclopentyl}-hept-5-enoic acid (high R$_f$ diastereomer, 41, FIG. 5). The same procedure as above for the (36) was used to give 9 mg (0.018 mmol, 85%) of acid (41). 300 MHz $^1$H NMR (CDCl$_3$, ppm) δ 7.73 (2H, d, J=8.8 Hz) 7.45-7.30 (2H, m) 5.8-5.6 (2H, m) 5.45-5.30 (2H, m) 4.3-4.2 (1H, m) 3.61 (1H, d, J=9.7 Hz) 3.1-3.0 (2H, m) 2.5-1.9 (10H, m) 1.7-1.6 (2H, m) 1.10 (3H, s) 0.90 (3H, s).

2-Benzo[b]thiophen-2-yl-ethanol (54b, FIG. 6). n-BuLi (100 mL, 160 mmol, 1.6M/hexanes) was added to a −78° C. mixture of thianaphthene (54a) (17.31 g, 129 mmol) in THF (70 mL)/ether (30 mL). The mixture was stirred at −78° C. for 2 hours and then a solution of ethylene oxide (42.86 g, 1.071 mmol) in THF (70 mL)/ether (30 mL) was added by cannula over 15 minutes. The resulting mixture was stirred for 2 hours at −78° C. and then at room temperature for 15 hours. The mixture was evaporated, 200 mL water was added, and the resulting mixture was extracted with ethyl acetate (3×150 mL). The combined organic solution was washed with brine and then dried (Na$_2$SO$_4$), filtered, and evaporated. Purification by flash chromatography on silica gel (20% ethyl acetate/hexanes) gave (54b) (13.61 g, 78 mmol, 60%).

Figure 6:
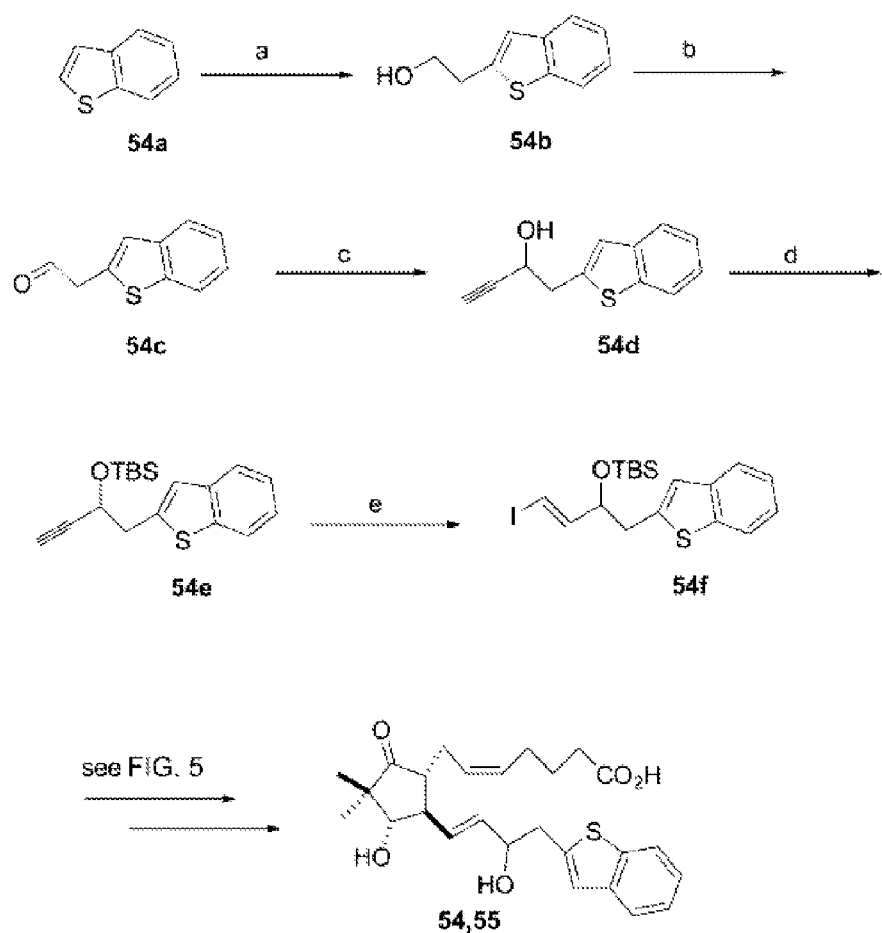

Benzo[b]thiophen-2-yl-acetaldehyde (54c, FIG. 6). A 0° C. mixture of (54b) (8.019 g, 44.9 mmol) in 100 mL dichloromethane was treated with Dess-Martin reagent (20 g, 47.2 mmol). The mixture was stirred at 0° C. for 10 minutes and at room temperature for 40 minutes. Saturated NaHCO$_3$ solution (200 mL) and 0.1 M NaHSO$_3$ solution were added and the resulting mixture was extracted with ethyl acetate (3×300 mL). The combined organic solution was dried (Na$_2$SO$_4$), filtered and evaporated to give (54c) (8.77 g). The aldehyde was taken on crude for the next reaction.

1-Benzo[b]thiophen-2-yl-but-3-yn-2-ol (54d, FIG. 6). A solution of crude (54c) (8.77 g) in THF (100 mL) was added to a solution of ethynylmagnesium bromide (450 mL, 225 mmol, 0.5 M/THF) at 0° C. by cannula. The mixture was stirred for 1 hour at 0° C. and for 1 hour at room temperature. The reaction was then quenched by addition of 200 mL saturated NH$_4$Cl solution. The layers were separated and the aqueous layer extracted with ethyl acetate (3×200 mL). The combined organic solution was washed with brine and then dried (Na$_2$SO$_4$), filtered and evaporated. Purification by flash chromatography on silica gel (10% 20% ethyl acetate/hexanes) gave (54d) (7.67 g, 37.9 mmol, 84% from 5-2).

(1-Benzo[b]thiophen-2-ylmethyl-prop-2-ynyloxy)-tert-butyl-dimethyl-silane (54e, FIG. 6). DMAP (2.306 g, 18.9 mmol), TBSCl (11.502 g, 76.3 mmol) and triethylamine (5.25 mL, 37.7 mmol) were added to a solution of (54d) (7.67 g, 37.9 mmol) in dichloromethane (120 mL). After 17 hours, 150 mL of saturated NH4Cl solution was added and the layers were separated. The aqueous layer was extracted with dichloromethane (3×100 mL) and the combined organic solution was dried (Na$_2$SO$_4$), filtered and evaporated. Purification by flash chromatography on silica gel (4% ethyl acetate/hexanes) gave (54e) (8.38 g, 26.5 mmol, 70%).

((E)-1-Benzo[b]thiophen-2-ylmethyl-3-iodo-allyloxy)-tert-butyl-dimethyl-silane (54f, FIG. 6). Cp$_2$ZrHCl (1.719 g, 6.67 mmol) was added to a solution of (54e) (1.372 g, 4.34 mmol) in dichloromethane (30 mL). The reaction was stirred for 30 minutes at room temperature and N-iodosuccinimide (1.997 g, 8.88 mmol) was added. After 1 hour, the reaction was poured into 100 mL of saturated NaHCO$_3$ solution. The resulting mixture was extracted with dichloromethane (3×75 mL) and the combined organic extracts dried (Na$_2$SO$_4$), filtered and evaporated. Purification by flash chromatography on silica gel (2% ethyl acetate/hexanes) gave (54f) (1.7484 g, 91%).

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (54, 55, FIG. 6). A solution of (54f) was treated in a manner similar to the scheme outlined in FIG. 5 to produce (54) and (55).

Figure 7:
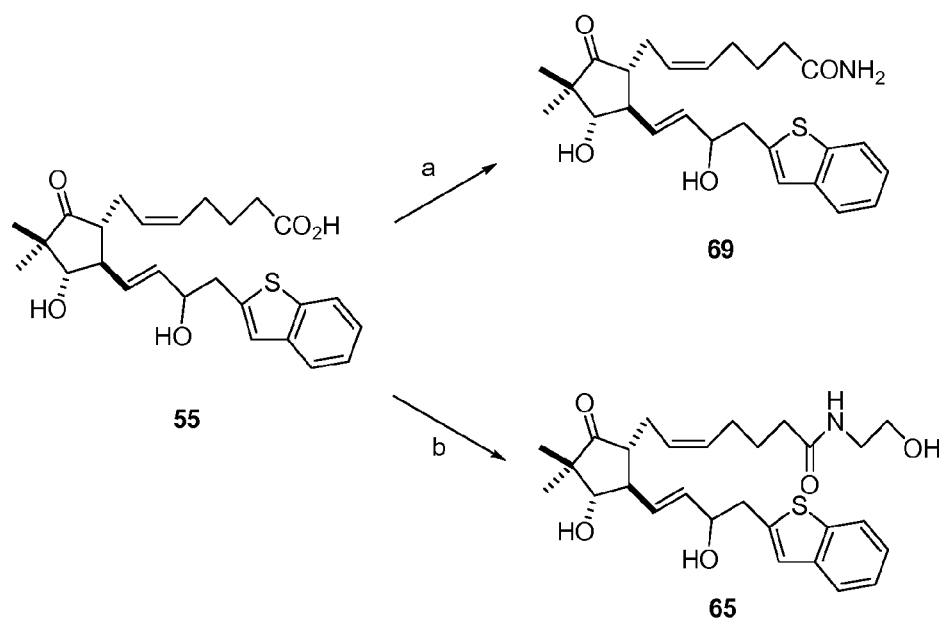

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid (2-hydroxy-ethyl)-amide (60-63, 65, FIG. 7). A solution of acid (55) (7 mg, 0.015 mmol) in DMF (0.5 mL) was treated with N-hydroxysuccinimide (6.9 mg, 0.056 mmol). The mixture was stirred for 5 minutes and 1-[3-(dimethylamino)propyl]-3-ethylcarbodiimide hydrochloride (EDCl, 20.7 mg, 0.11 mmol) was added. After stirring for 7 hours, 2-aminoethanol (5 µL, 0.083 mmol) was added and the mixture stirred further for 16 hours. Ethyl acetate (50 mL) was added and the mixture washed with water (3×50 mL) and brine (50 mL). The organic layer was dried ($Na_2SO_4$), filtered and evaporated. Purification by flash chromatography on silica gel (5% methanol/dichloromethane) followed by preparative thin layer chromatography (10% methanol/dichloromethane) gave amide (65) (5 mg, 0.010 mmol, 65%). Amides (60-63) were prepared in a similar manner.

(Z)-7-[(1R,4S,5R)-5-((E)-4-Benzo[b]thiophen-2-yl-3-hydroxy-but-1-enyl)-4-hydroxy-3,3-dimethyl-2-oxo-cyclopentyl]-hept-5-enoic acid amide (69, FIG. 7). A solution of acid (55) (9 mg, 0.02 mmol) in dichloromethane (0.2 mL) was treated with triethylamine (15 µL, 0.11 mmol). The solution was cooled to 0° C. and after 10 minutes, ethyl chloroformate (7 µL, 0.073 mmol) was added. The solution was stirred further for 1 hour at 0° C. and then concentrated aqueous ammonium hydroxide solution was added (10 µL, 0.26 mmol). The reaction was stirred at room temperature overnight and then quenched by addition of 0.5 M HCl (7 mL). The mixture was extracted with ethyl acetate (3×30 mL), the combined ethyl acetate solution washed with saturated $NaHCO_3$ solution (20 mL) and brine (20 mL), and then dried ($Na_2SO_4$), filtered and evaporated. Purification by flash chromatography on silica gel (2%-6% methanol/dichloromethane) gave the title amide (2.6 mg, 28%).

Example 2

Compounds of Formula I Promote Synthesis of TGF-β and VEGF

This example illustrates that compounds of formula I promote formation of blood vessels.

To test whether the compounds of Formula I promote the formation of blood vessels, and incisional wound model was employed over a 14-day period. Sprague-Dawley rats (180-200 g) were anesthetized, the backs shaved, and a 2-cm long incision was made on the back skin of rats under sterile conditions, reaching the deep fascia. The wound was immediately closed with 4-0 sutures. The animals were topically treated with vehicle or Compound 1 at 0.004% twice daily. The vehicle contains ethanol 30%, propylene glycol 12%, dipropylene glycol 5%, benzyl alcohol 5%, glycerol 3% and normal saline 45%. Biopsy samples of skin wound tissues were analyzed with Western blots day-7 and day-14 post-surgery. Tissue samples about 1 mm thick were taken from both sides of the wound. Protein was extracted, and FGF-2/VEGF expression was monitored, with Western blot analysis.

Compound 1 treatment significantly enhanced the expression of FGF-2 by 60%, as normalized with β-actin (a housekeeping gene) by day-7 of the experiment (P=0.004). This significantly different increase in FGF-2 synthesis persisted for the whole study period (P=0.04). VEGF expression increased 25% as normalized with β-actin, by Compound 1 treatment on day-7 (P=0.039). This significantly different increase in synthesis returned to the baseline by day-14. Such an increase in FGF-2 and VEGF is consistent with their role in new blood vessel formation. The up-regulation of FGF-2 and VEGF by Compound 1 treatment was also observed in studies using an oral ulcer wound model.

Example 3

Adipose Tissue Transplant for Breast Defect Correction

This example illustrates the use of compositions and methods disclosed herein for a breast defect correction.

A 32-year-old woman presented with complaints that the medial portions of her breast implants were visible, which accentuated the "bony" appearance of her sternum. In addition she felt her breast were too far apart. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. The harvested area is injected subcutaneously with a standard tumescent fluid solution containing a saline solution, 0.5% lidocaine, and about 0.001% epinephrine. Using an 11-blade scalpel, a small puncture wound is made in order to transverse the dermis. The blade is turned 360 degrees to complete the wound. A two-holed blunt harvesting cannula (3 mm inner diameter) connected to a vacuum pump at low negative pressure (0.5 atm) is then inserted into the subcutaneous adipose tissue plane. The cannula is then moved throughout the plane to disrupt the connective tissue architecture. The volume of aspirate obtained is about 300 mL. The harvest adipose tissue is processed by centrifugation at 3,000 g for 3 minutes to separate healthy adipocytes and regenerative cells from blood, infiltration fluid and cell debris.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 3 mL syringes. One-holed blunt infiltration cannulas (3 mm inner diameter) are used to place the adipose tissue subcutaneously over the lateral sternum and medial breast bilaterally, 70 mL on the right and 50 mL on the left. The adipose tissue is administered in a tear like fashion to increase the surface area to volume ratio.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately one month after the procedure, the woman indicates that her quality of life has improved.

Example 4

Adipose Tissue Transplant for Breast Augmentation

This example illustrates the use of compositions and methods disclosed herein for a breast augmentation.

A 28-year-old woman presented micromastia or breast hypoplasia. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the lateral and medial thigh regions. Using a 10-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 600 mL. The harvest adipose tissue is processed by centrifugation at 2,700 g for 5 minutes to separate healthy adipocytes and regenerative cells from blood, infiltration fluid and cell debris. The centrifuged adipose tissue is then washed once is a Ringer's saline solution with lactone.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously using axillary, periareolar, and inframammary routes bilaterally, 190 mL on the right and 245 mL on the left. The adipose tissue is administered in a tear like fashion to increase the surface area to volume ratio.

Alternatively, the adipose tissue is first administered into the individual, and then a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted. As another alternative, a compound of formula I, such as, e.g., Compound 1, Compound 2, Compound 3, Compound 4, and/or Compound 5 is first administered into the individual, and then adiposes tissue and a composition comprising HA are subsequently administered (either at the same time, or sequentially i.e., adipose tissue first and then HA or HA first and then adipose tissue) into the same, or in the vicinity of, the region where the compound was administered. As yet another alternative, composition comprising HA is first administered into the individual, and then adiposes tissue and a compound of formula I, such as, e.g., Compound 1, Compound 2, Compound 3, Compound 4, and/or Compound 5 are subsequently administered (either at the same time, or sequentially i.e., adipose tissue first and then compound or compound first and then adipose tissue) into the same, or in the vicinity of, the region where the HA was administered.

The individual is monitored for approximately 7 days. The physician evaluates the engrafted tissue and determines that the engraftment was successful. Both the woman and her physician are satisfied with the results of the procedure. Approximately one month after the procedure, the woman indicates that her quality of life has improved.

Example 5

Adipose Tissue Transplant for Breast Disorder

This example illustrates the use of compositions and methods disclosed herein for a breast disorder.

A 29-year-old woman presented with bilaterial tiberous breast deformity. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdomen, buttock, lateral and medial thigh, and trochanter regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 1,400 mL.

The harvested adipose tissue is divided into two, approximately equal portions. One portion is processed by gravity sedimentation to separate healthy adipocytes and regenerative cells from blood, infiltration fluid and cell debris. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the sediment purified adipose tissue.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place the adipose tissue subcutaneously in multiple planes axillary, periareolar, and inframammary routes bilaterally, 380 mL on the right and 370 mL on the left. The adipose tissue is administered in a tear like fashion to increase the surface area to volume ratio.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure. Approximately one month after the procedure, the woman indicates that her quality of life has improved.

Example 6

Adipose Tissue Transplant for Facial Defects of Cheek

This example illustrates the use of compositions and methods disclosed herein for a facial disorder.

A 28-year-old woman presented with a lean face. She felt her face looked old, sad and bitter because of the less fullness of her cheek contour. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, adipose tissue is harvested from the woman. The procedure is performed at the individual's bedside. The physician examines the individual's habitus for a suitable site or sites to harvest adipose tissue and selects the abdominal region. The harvested area is injected subcutaneously with a standard tumescent fluid solution containing a saline solution, 0.08% lidocaine, and about 0.001% epinephrine. Using an 11-blade scalpel, a small puncture wound is made in order to transverse the dermis. The blade is turned 360 degrees to complete the wound. A two-holed blunt harvesting cannula (2.5 mm inner diameter) connected to a 60 mL syringe is then inserted into the subcutaneous adipose tissue plane. The cannula is then moved throughout the plane to disrupt the connective tissue architecture. The volume of aspirate obtained is about 50 mL. The harvest adipose tissue is processed by washing the harvested tissue with saline to remove lidocaine, oil and residual blood. The washed tissue is then centrifugation at 100 g for 2 minutes to separate healthy adipocytes and regenerative cells from any remaining blood, infiltration fluid and cell debris.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 20 mL syringes. One-holed blunt infiltration cannulas (3 mm inner diameter) are used to place about 15 mL of adipose tissue subcutaneously and under superficial musculoaponeurotix system into the left and right cheeks.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 7

Adipose Tissue Transplant for Facial Defects of Eyelids

This example illustrates the use of compositions and methods disclosed herein for a facial disorder.

A 37-year-old woman presented with sunken eyes and this appearance made her look old and fierce. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To adipose tissue is harvested from the woman as described in Example 6.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 20 mL syringes. One-holed blunt infiltration cannulas (3 mm inner diameter) are used to place about 2.5 mL of adipose tissue subcutaneously and under superficial musculoaponeurotix system into the upper eyelid regions.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 8

Adipose Tissue Transplant for Facial Defects

This example illustrates the use of compositions and methods disclosed herein for a breast disorder.

A 33-year-old woman presented with depressed bilateral temporal and cheek areas. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To adipose tissue is harvested from the woman as described in Example 6, except that 200 mL of adipose tissue is collected.

The harvested adipose tissue is divided into two, approximately equal portions. One portion is processed by saline washing and centrifugation as described in Example 6. The other portion is used to isolate regenerative cells. This portion is digested with 0.075% collagenase in buffered saline for 30 minutes on a shaker at 37° C. Regenerative cells are then separated from mature adipocytes and connective tissue by centrifuging at 800 g for 10 minutes. The pellet containing the regenerative cells is then washed three times with buffered saline. The washed regenerative cells are then added back to the purified adipose tissue.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 10 mL syringes. One-holed blunt infiltration cannulas (3 mm inner diameter) are used to place about 16 mL of adipose tissue subcutaneously and under superficial musculoaponeurotix system into the left and right temporal and cheeks regions.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored for approximately 7 days. The physician evaluates the engrafted tissue and determines that the engraftment was successful. Both the woman and her physician are satisfied with the results of the procedure because she looked younger. Approximately one month after the procedure, the woman indicates that her quality of life has improved.

Example 9

Adipose Tissue Transplant to Treat Stress Urinary Incontinence

This example illustrates the use of compositions and methods disclosed herein for treating stress urinary incontinence.

A 55 year old man presents with urinary incontinence. Pre-operative evaluation of the patient includes routine history and physical examination in addition to thorough informed consent disclosing all relevant risks and benefits of the procedure. The physician evaluating the individual determines that he is a candidate for a soft tissue replacement method using the compositions and methods disclosed herein.

To begin the procedure, adipose tissue is harvested from the man. The procedure is performed at the individual's bedside. The physician examines the individual's habitus for a suitable site or sites to harvest adipose tissue and selects the abdomen, and lateral and medial thigh regions. Using a 12-blade scalpel, a small puncture wound is made in order to transverse the dermis. The blade is turned 360 degrees to complete the wound. A two-holed blunt harvesting cannula (3 mm inner diameter) connected to a syringe is then inserted into the subcutaneous adipose tissue plane. The cannula is then moved throughout the plane to disrupt the connective tissue architecture. The volume of aspirate obtained is about 900 mL.

A compound of formula I, such as, e.g., Compound 1, Compound 2, Compound 3, Compound 4, and/or Compound 5, is mixed with an effective amount of HA and the processed adipose tissue. The amount of compound added is an amount sufficient to promote formation of a blood supply sufficient to support the transplanted tissue. This composition is then transferred to 20 mL syringes. One-holed blunt infiltration cannulas (14-gauge) are used to place about 800 mL of adipose tissue transdermally into the bladder neck and proximal urethra regions.

Alternatively, the adipose tissue is first administered into the individual, and a composition comprising compound of formula I, such as, e.g., Compound 1, Compound 2, Compound 3, Compound 4, and/or Compound 5 and HA is subsequently administered into the same, or in the vicinity of, the region where the adipose tissue was implanted. Alternatively, the adipose tissue is first administered into the individual, and a compound of formula I, such as, e.g., Compound 1, Compound 2, Compound 3, Compound 4, and/or Compound 5 and a composition comprising HA are subsequently administered (either at the same time, or sequentially i.e., compound of formula I first and then HA or HA first and then compound of formula I) into the same, or in the vicinity of, the region where the adipose tissue was implanted.

The individual is monitored after the procedure. Approximately three days after the transplant, the man indicates that he experiences a decreased frequency of incontinence. Approximately one month after the procedure, the individual indicates that his quality of life has improved. The physician evaluates the engrafted tissue and determines that the long-term engraftment was successful.

Example 10

Adipose Tissue Transplant for Breast Defect Correction

This example illustrates the use of compositions and methods disclosed herein for a breast defect correction.

A 56-year-old woman presents with a surgically removed breast due to cancer. Pre-operative evaluation of the person includes routine history and physical examination in addition to thorough informed consent disclosing all relevant risks and benefits of the procedure. The physician evaluating the individual determines that she is a candidate for a soft tissue replacement method using the compositions and methods disclosed herein.

To begin the procedure, a breast mound is formed using a TRAM-flap procedure. In this procedure, a portion of abdomen tissue, including skin, adipose tissue, minor muscles and connective tissues, is taken from the patient's abdomen and transplanted onto the breast site. This tissue is then used to create a breast mound.

A composition comprising a compound of formula I, such as, e.g., Compound 1, Compound 2, Compound 3, Compound 4, and/or Compound 5 and an effective amount of HA is then administered into the breast mound region. The amount of compound administered is an amount sufficient to promote formation of a blood supply sufficient to support the transplanted tissue.

The individual is monitored for approximately 7 days. The physician evaluates the engrafted tissue and determines that the engraftment was successful. Both the woman and her physician are satisfied with the results of the procedure. Approximately one month after the procedure, the woman indicates that her quality of life has improved. Subsequent surgery is performed to create a nipple and areola.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A composition comprising:
   a) an adipose tissue;
   b) a hydrogel material comprising a glycosaminoglycan polymer;
   c) a compound having the structure of compound 24,

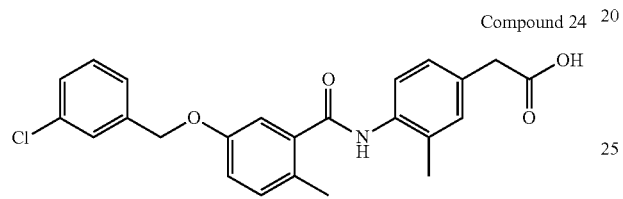

Compound 24 a pharmaceutically acceptable salt thereof, or a pharmaceutically acceptable amine salt thereof.

2. The composition of claim 1, wherein the compound is incorporated into a drug delivery platform comprising a biodegradable polymer matrix.

3. The composition of claim 1, wherein the hydrogel material is a porous material or solid particles.

4. The composition of claim 1, wherein glycosaminoglycan polymer is a hyaluronan polymer.

5. A method of treating a soft tissue condition of an individual, the method comprising the step of administering to a site of the soft tissue condition a composition comprising adipose tissue, a hydrogel material comprising a glycosaminoglycan polymer, and a compound, the compound having the structure of compound 24,

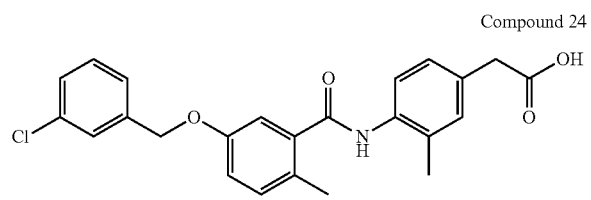 [SMILES: Cc1cc(CC(=O)O)ccc1NC(=O)c1cc(OCc2cccc(Cl)c2)ccc1C]

Compound 24 a pharmaceutically acceptable salt thereof, or a pharmaceutically acceptable amine salt thereof;
wherein administration of the composition promotes formation of a blood supply sufficient to support the transplanted tissue, thereby treating the soft tissue site.

6. The method of claim 5, wherein the soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, or a genital condition.

7. The method of claim 6, wherein the breast tissue condition is a breast imperfection, a breast defect, a breast augmentation, or a breast reconstruction.

8. The method of claim 6, wherein the facial tissue condition is a facial imperfection, a facial defect, a facial augmentation, or a facial reconstruction.

9. The method of claim 6, wherein the facial soft tissue condition is a dermal divot, a sunken cheek, a thin lip, a nasal imperfection or defect, a retro-orbital imperfection or defect, a facial fold, a facial line, a facial wrinkle, or other size, shape or contour imperfection or defect of the face.

10. The method of claim 5, wherein the soft tissue condition is urinary incontinence, fecal incontinence, or gastroesophageal reflux disease (GERD).

11. A method of treating a soft tissue condition of an individual, the method comprising the steps of
   a) administering adipose tissue to a site of the soft tissue condition;
   b) administering an effective amount of a hydrogel material comprising a glycosaminoglycan polymer to the site of the soft tissue condition; and
   c) administering a compound to the site of the soft tissue condition, the compound having the structure of compound 24,

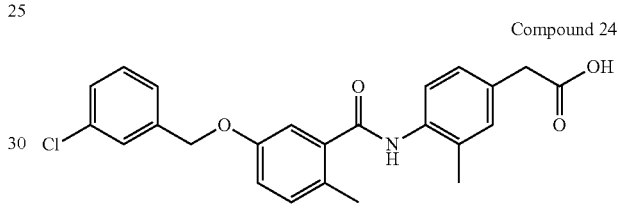

Compound 24 a pharmaceutically acceptable salt thereof, or a pharmaceutically acceptable amine salt thereof;
wherein administration of the compound promotes formation of a blood supply sufficient to support the transplanted tissue, thereby treating the soft tissue site.

12. The method of claim 11, wherein the glycosaminoglycan polymer is a hyaluronan polymer.

13. The method of claim 11, wherein the hydrogel material is administered at the same time as, before, or after the compound is administered.

14. The method of claim 11, wherein the soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, or a genital condition.

15. The method of claim 14, wherein the breast tissue condition is a breast imperfection, a breast defect, a breast augmentation, or a breast reconstruction.

16. The method of claim 14, wherein the facial tissue condition is a facial imperfection, a facial defect, a facial augmentation, or a facial reconstruction.

17. The method of claim 14, wherein the facial soft tissue condition is a dermal divot, a sunken cheek, a thin lip, a nasal imperfection or defect, a retro-orbital imperfection or defect, a facial fold, a facial line, a facial wrinkle, or other size, shape or contour imperfection or defect of the face.

18. The method of claim 11, wherein the soft tissue condition is urinary incontinence, fecal incontinence, or gastroesophageal reflux disease (GERD).

* * * * *